(12) United States Patent
Bossart et al.

(10) Patent No.: US 10,538,567 B2
(45) Date of Patent: Jan. 21, 2020

(54) COMPOUNDS AS PEPTIDIC TRIGONAL GLP1/GLUCAGON/GIP RECEPTOR AGONISTS

(71) Applicant: SANOFI, Paris (FR)

(72) Inventors: Martin Bossart, Frankfurt am Main (DE); Andreas Evers, Frankfurt am Main (DE); Torsten Haack, Frankfurt am Main (DE); Dieter Kadereit, Frankfurt am Main (DE); Katrin Lorenz, Frankfurt am Main (DE); Michael Wagner, Frankfurt am Main (DE); Stefania Pfeiffer-Marek, Frankfurt am Main (DE); Martin Lorenz, Frankfurt am Main (DE)

(73) Assignee: SANOFI, Paris (FR)

(*) Notice: Subject to any disclaimer, the term of this patent is extended or adjusted under 35 U.S.C. 154(b) by 62 days.

(21) Appl. No.: 15/829,680

(22) Filed: Dec. 1, 2017

(65) Prior Publication Data

US 2018/0155406 A1 Jun. 7, 2018

(30) Foreign Application Priority Data

Dec. 2, 2016 (EP) ..................................... 16306604

(51) Int. Cl.
| | | |
|---|---|---|
| *A61K 38/00* | (2006.01) | |
| *C07K 14/575* | (2006.01) | |
| *C07K 14/605* | (2006.01) | |
| *A61K 38/22* | (2006.01) | |
| *A61K 45/06* | (2006.01) | |

(52) U.S. Cl.
CPC .... *C07K 14/57563* (2013.01); *A61K 38/2278* (2013.01); *A61K 45/06* (2013.01); *C07K 14/575* (2013.01); *C07K 14/605* (2013.01); *A61K 38/00* (2013.01)

(58) Field of Classification Search
None
See application file for complete search history.

(56) References Cited

U.S. PATENT DOCUMENTS

2008/0019911 A1* 1/2008 Xu ..................... G01N 33/6893
424/9.2

FOREIGN PATENT DOCUMENTS

| EP | 2 387 989 A2 | 11/2011 |
|---|---|---|
| WO | WO 2004/035623 A2 | 4/2004 |
| WO | WO 2006/134340 A9 | 3/2009 |
| WO | WO 2010/011439 A2 | 1/2010 |
| WO | WO 2010/148089 A1 | 12/2010 |
| WO | WO 2012/088116 A2 | 6/2012 |
| WO | WO 2013/192129 A1 | 12/2013 |
| WO | WO 2013/192130 A1 | 12/2013 |
| WO | WO 2014/049610 A2 | 4/2014 |
| WO | WO 2014/056872 A1 | 4/2014 |
| WO | WO 2014/096145 A1 | 6/2014 |
| WO | WO 2014/096148 A1 | 6/2014 |
| WO | WO 2014/096149 A1 | 6/2014 |
| WO | WO 2014/096150 A1 | 6/2014 |
| WO | WO 2015/067716 A1 | 5/2015 |
| WO | WO 2015/086731 A1 | 6/2015 |
| WO | WO 2015/086732 A1 | 6/2015 |
| WO | WO 2015/086733 A1 | 6/2015 |
| WO | WO 2015/155141 A1 | 10/2015 |
| WO | WO 2016/198624 A1 | 12/2016 |
| WO | WO 2018/100134 A1 | 6/2018 |

OTHER PUBLICATIONS

Baggio et al., (2007) "Biology of Incretins: GLP-1 and GIP," Gastroenterology, vol. 132, 2131-2157.

Bhat et al., "A DPP-IV-resistant triple-acting agonist of GIP, GLP-1 and glucagon receptors with potent glucose-lowering and insulinotropic actions in high-fat-fed mice" Diabetologia. Jun. 2013;56(6):1417-24.

Bhat et al., "A novel GIP-oxyntomodulin hybrid peptide acting through GIP, glucagon and GLP-1 receptors exhibits weight reducing and anti-diabetic properties" Biochem Pharmacol. Jun. 1, 2013;85(11):1655-62.

Biancalana et al., (2010) "Molecular mechanism of thioflavin-T binding to amyloid fibrils," Biochimica et Biophysica Acta., 1804(7):1405-1412.

Bis et al., (2014) "Antimicrobial preservatives induce aggregation of interferon alpha-2a: The order in which preservatives induce protein aggregation is independent of the protein," International Journal of Pharmaceutics, vol. 472, pp. 356-361.

Buse et al., (2009) "Liraglutide once a day versus exenatide twice a day for type 2 diabetes: a 26-week randomised, parallel-group, multinational, open-label trial (LEAD-6)," Lancet, vol. 374, pp. 39-47.

Chhabra et al. (1998) "An appraisal of new variants of DDE amine protecting group for solid phase peptide synthesis," Tetrahedron Letters, vol. 39, pp. 1603-1606.

Connolly et al. (2012) "Weak interactions govern the viscosity of concentrated antibody solutions: high-throughput analysis using the diffusion interaction parameter," Biophysical Journal, vol. 103, pp. 69-78.

Druce et al., "Investigation of structure-activity relationships of Oxyntomodulin (Oxm) using Oxm analogs" Endocrinology. Apr. 2009;150(4):1712-22.

Drucker et al. (2010) "Liraglutide," Nature Review, vol. 9, pp. 267-268.

(Continued)

*Primary Examiner* — Jeanette M Lieb
(74) *Attorney, Agent, or Firm* — Lathrop Gage LLP; James H. Velema, Esq.

(57) ABSTRACT

The present invention relates to trigonal GLP-1/glucagon/GIP receptor agonists and their medical use, for example in the treatment of disorders of the metabolic syndrome, including diabetes and obesity, as well as for reduction of excess food intake.

38 Claims, 31 Drawing Sheets

Figure 1:
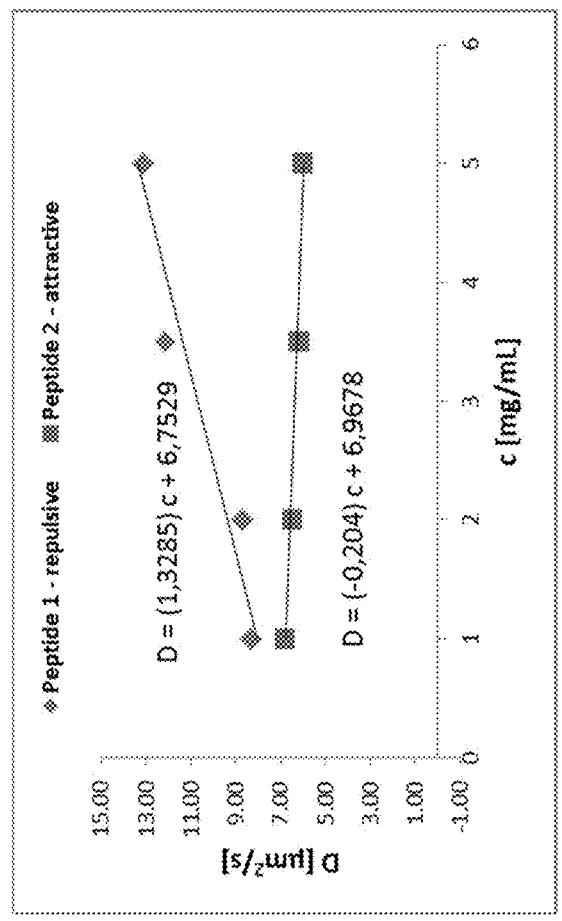

Specification includes a Sequence Listing.

(56) References Cited

OTHER PUBLICATIONS

Eng et al. (1996) "Prolonged effect of exendin-4 on hyperglycemia of db/db mice," Diabetes, 45(Suppl. 2): 152A, Abstract 554.
Finan et al., "A rationally designed monomeric peptide triagonist corrects obesity and diabetes in rodents" Nat Med. Jan. 2015;21(1):27-36.
Gault et al. (2013) "A novel glucagon-like peptide-1 (GLP-1)/Glucagon hybrid peptide with triple-acting agonist activity at glucose-dependent insulinotropic polypeptide, GLP-1, and Glucagon receptors and therapeutic potential in high fat-med mice," The Journal of Biological Chemistry, 288(49):35581-35591.
Harding et al. (1985) "The concentration-dependence of macromolecular parameters," Biochem. J., vol. 231, pp. 543-547.
Hargrove et al., "Biological activity of AC3174, a peptide analog of exendin-4" Regul. Pept. Jun. 7, 2007;141(1-3):113-9.
Heppner et al., "Glucagon regulation of energy metabolism" Physiol Behav. Jul. 14, 2010;100(5):545-8.
International Search Report for PCT/EP2017/081125, dated Feb. 3, 2018.
International Search Report for PCT/EP2017/081126, dated Feb. 3, 2018.
Kamerzell et al. (2011) "Protein-excipient interactions: Mechanisms and biophysical characterization applied to protein formulation development," Advanced Drug Delivery Reviews, vol. 63, pp. 1118-1159.
Kaiser et al. (1970) "Xolor test for detection of free terminal amino groups in the solid-phase synthesis of peptides," Anal. Biochem., 34(2):595-598.
King et al. (1990) "A cleavage method which minimizes side reactions following Fmoc solid phase peptide synthesis," Int. J. Peptide Protein Res., vol. 36, pp. 255-266.
Krstenansky et al., "Importance of the 10-13 region of glucagon for its receptor interactions and activation of adenylate cyclase" Biochemistry. Jul. 1, 1986;25(13):3833-9.
LeVine et al., (1999) "Quantification of β-sheet amyloid fibril structures with thioflavin T," Methods Enzymol, vol. 309, pp. 274-284.
Meir et al., (2004) "Ahterosclerosis in the Apolopoprotein E-deficient mouse," Arterioscler Thromb. Vasc. Biol., vol. 24, pp. 1006-1014.
Naiki et al., (1989) "Fluorometric determination of amyloid fibrils in vitro using the fluorescent dye, thioflavine T," Analytical Biochemistry, vol. 177: 244-249.
Pedersen et al. (2006) "N- and C-Terminal Hydrophobic Patches are Involved in Fibrillation of Glucagon," Biochemistry, vol. 45, pp. 14503-14512.
Pocai, "Action and therapeutic potential of oxyntomodulin", Mol. Metab. Dec. 14, 2013;3(3):241-51.
Rosenfeld et al., (2000) "Advanced Atherosclerotic Lesions in the Innominate Artery of the ApoE Knockout Mouse," Aterioscler Thromb. Vasc. Biol., vol. 20, pp. 2587-2592.
Vojkovsky, T., (1995) "Detection of secondary amines on solid phase," Peptide Research, 8(4):236-237 (abstract).
Yadav et al. (2009) "Specific interactions in high concentration antibody solutions resulting in high viscosity," Journal of Pharmaceutical Sciences, 99(3):1152-1168.

* cited by examiner

SEQUENCE LISTING

<160> NUMBER OF SEQ ID NOS: 29

<210> SEQ ID NO 1
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: liraglutide
<220> FEATURE:
<221> NAME/KEY: MOD_RES
<222> LOCATION: (20)..(20)
<223> OTHER INFORMATION: Lys is derivatized at N6 with
      (S)-4-Carboxy-4-hexadecanoylamino-butyryl-

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
                35

<210> SEQ ID NO 5
<211> LENGTH: 42

```
<212> TYPE: PRT
<213> ORGANISM: Homo sapiens

<400> SEQUENCE: 5

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 6
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 6

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly His Pro
            20                  25                  30

Ser Xaa Lys Pro Pro Pro Lys
        35

<210> SEQ ID NO 7
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
```

<223> OTHER INFORMATION: AMIDATION

<400> SEQUENCE: 7

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Xaa Gly His Pro
            20                  25                  30

Ser Xaa Lys Pro Pro Pro Lys
        35

<210> SEQ ID NO 8
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 8

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly Pro Pro
            20                  25                  30

Ser Xaa Lys Pro Pro Pro Lys
        35

<210> SEQ ID NO 9
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

```
<400> SEQUENCE: 9

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Xaa Gly Pro Pro
            20                  25                  30

Ser Xaa Lys Pro Pro Pro Lys
        35

<210> SEQ ID NO 10
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 10

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly Pro Pro
            20                  25                  30

Ser Xaa Lys Pro Pro Pro Lys
        35

<210> SEQ ID NO 11
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
```

```
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 11

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly Pro Pro
            20                  25                  30

Ser Xaa Lys Pro Pro Pro Lys
        35

<210> SEQ ID NO 12
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 12

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly His Pro
            20                  25                  30

Ser Xaa Lys Pro Pro Pro Lys
        35

<210> SEQ ID NO 13
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-((S)-4-carboxy-4-hexadecanoylamino-butyrylamino)-
      butyryl-
<220> FEATURE:
<221> NAME/KEY: misc_feature
```

<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 13

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly His Pro
            20                  25                  30

Ser Xaa Lys Pro Pro Pro Lys
        35

<210> SEQ ID NO 14
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      [[(4S)-4-carboxy-4-[[(4S)-4-carboxy-4-[[2-[2-[2-(hexadecanoylamin
      o)ethoxy]ethoxy]acetyl]amino]butyrylamino]-butyryl-
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 14

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly His Pro
            20                  25                  30

Ser Xaa Lys Pro Pro Pro Lys
        35

<210> SEQ ID NO 15
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      [[(4S)-4-carboxy-4-[[(4S)-4-carboxy-4-[[2-[2-[2-(hexadecanoylamin

```
                  o)ethoxy]ethoxy]acetyl]amino]butyrylamino]-butyryl-
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 15

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Xaa Gly His Pro
            20                  25                  30

Ser Xaa Lys Pro Pro Pro Lys
        35

<210> SEQ ID NO 16
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-hexadecanoylamino-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 16

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly Pro Pro
            20                  25                  30

Ser Xaa Lys Pro Pro Pro Lys
        35

<210> SEQ ID NO 17
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
```

```
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-octadecanoylamino-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 17

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly Pro Pro
            20                  25                  30

Ser Xaa Lys Pro Pro Pro Lys
        35

<210> SEQ ID NO 18
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-hexadecanoylamino-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 18

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly Pro Pro
            20                  25                  30

Ser Xaa Lys Pro Pro Pro Lys
        35

<210> SEQ ID NO 19
<211> LENGTH: 39
<212> TYPE: PRT
<213> ORGANISM: Artificial Sequence
```

```
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-octadecanoylamino-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 19

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly Pro Pro
            20                  25                  30

Ser Xaa Lys Pro Pro Pro Lys
        35

<210> SEQ ID NO 20
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-hexadecanoylamino-butyryl-
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 20

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly Pro Pro
            20                  25                  30

Ser Xaa Lys Pro Pro Pro Lys
        35

<210> SEQ ID NO 21
<211> LENGTH: 39
<212> TYPE: PRT
<213> ORGANISM: Artificial Sequence
<220> FEATURE:
<223> OTHER INFORMATION: Exendin-4 derivative
<220> FEATURE:
```

```
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-octadecanoylamino-butyryl-
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 21

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly Pro Pro
            20                  25                  30

Ser Xaa Lys Pro Pro Pro Lys
        35

<210> SEQ ID NO 22
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with (4S)-Carboxy-
      [2-(2-
[(4R)-5-carboxy-4-hexadecanoylamino-pentanoylamino]-etho
      xy
-ethoxy)-acetylamino]-butyryl
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 22

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Gly Gly His Pro
            20                  25                  30

Ser Xaa Lys Pro Pro Pro Lys
        35

<210> SEQ ID NO 23
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
```

```
<222> LOCATION: (14)..(14)
<223> OTHER INFORMATION: Lys is derivatized at N6 with (4S)-Carboxy-
      [2-(2-
[(4R)-5-carboxy-4-hexadecanoylamino-pentanoylamino]-etho
      xy
-ethoxy)-acetylamino]-butyryl
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 23

His Xaa His Gly Thr Phe Thr Ser Asp Leu Ser Lys Leu Lys Glu Glu
1               5                   10                  15

Gln Arg Gln Lys Glu Phe Ile Glu Trp Leu Lys Ala Xaa Gly His Pro
            20                  25                  30

Ser Xaa Lys Pro Pro Pro Lys
        35

<210> SEQ ID NO 24
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      [[(4S)-4-carboxy-4-[[(4S)-4-carboxy-4-[[2-[2-[2-(hexadecanoylamin
      o)ethoxy]ethoxy]acetyl]amino]butyrylamino]-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 24

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly Pro Pro
            20                  25                  30

Ser Xaa Lys Pro Pro Pro Lys
        35

<210> SEQ ID NO 25
<211> LENGTH: 39
<212> TYPE: PRT
<213> ORGANISM: Artificial Sequence
```

```
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with (4S)-Carboxy-
      [2-(2-
[(4R)-5-carboxy-4-hexadecanoylamino-pentanoylamino]-etho
      xy
-ethoxy)-acetylamino]-butyryl
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (29)..(29)
<223> OTHER INFORMATION: Xaa = dAla
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 25

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Xaa Gly Pro Pro
            20                  25                  30

Ser Xaa Lys Pro Pro Pro Lys
        35

<210> SEQ ID NO 26
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      [[(4S)-4-carboxy-4-[[(4S)-4-carboxy-4-[[2-[2-[2-(hexadecanoylamin
      o)ethoxy]ethoxy]acetyl]amino]butyrylamino]-butyryl-
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 26

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly Pro Pro
            20                  25                  30
```

Ser Xaa Lys Pro Pro Pro Lys
        35

<210> SEQ ID NO 27
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with (4S)-Carboxy-
      [2-(2-
      [(4R)-5-carboxy-4-hexadecanoylamino-pentanoylamino]-etho
      xy
      -ethoxy)-acetylamino]-butyryl
<220> FEATURE:
<221> NAME/KEY: misc_feature
<222> LOCATION: (20)..(20)
<223> OTHER INFORMATION: Xaa = Aib
<220> FEATURE:
<221> NAME/KEY: misc_feature
<222> LOCATION: (34)..(34)
<223> OTHER INFORMATION: Xaa = Aib
<220> FEATURE:
<221> NAME/KEY: MOD_RES
<222> LOCATION: (39)..(39)
<223> OTHER INFORMATION: AMIDATION

<400> SEQUENCE: 27

His Xaa His Gly Thr Phe Thr Ser Asp Leu Ser Lys Leu Lys Glu Glu
1               5                   10                  15

Gln Arg Gln Xaa Glu Phe Ile Glu Trp Leu Lys Ala Gly Gly Pro Pro
            20                  25                  30

Ser Xaa Lys Pro Pro Pro Lys
        35

<210> SEQ ID NO 28
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-octadecanoylamino-butyryl-
<220> FEATURE:
<221> NAME/KEY: MOD_RES
<222> LOCATION: (39)..(39)
<223> OTHER INFORMATION: AMIDATION

<400> SEQUENCE: 28

His Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ala Gly Gly Pro Ser
            20                  25                  30

Ser Gly Ala Pro Pro Pro Ser
        35

<210> SEQ ID NO 29

```
<211> LENGTH: 39
<212> TYPE: PRT
<213> ORGANISM: Artificial Sequence
<220> FEATURE:
<223> OTHER INFORMATION: Exendin-4 derivative
<220> FEATURE:
<221> NAME/KEY: misc_feature
<222> LOCATION: (2)..(2)
<223> OTHER INFORMATION: Xaa = Aib
<220> FEATURE:
<221> NAME/KEY: MOD_RES
<222> LOCATION: (14)..(14)
<223> OTHER INFORMATION: Lys is derivatized at N6 with
      (S)-4-Carboxy-4-octadecanoylamino-butyryl-
<220> FEATURE:
<221> NAME/KEY: MOD_RES
<222> LOCATION: (39)..(39)
<223> OTHER INFORMATION: AMIDATION

<400> SEQUENCE: 29

Tyr Xaa Gln Gly Thr Phe Thr Ser Asp Leu Ser Lys Gln Lys Asp Glu
1               5                   10                  15

Gln Arg Ala Lys Glu Phe Ile Glu Trp Leu Lys Ser Gly Gly Pro Ser
            20                  25                  30

Ser Gly Ala Pro Pro Pro Ser
        35
```

COMPOUNDS AS PEPTIDIC TRIGONAL GLP1/GLUCAGON/GIP RECEPTOR AGONISTS

RELATED APPLICATION

This application claims priority to European Patent Application No. 16306604.6, filed Dec. 2, 2016, the entire disclosure of which is hereby incorporated herein by reference.

FIELD OF THE INVENTION

The present invention relates to new compounds which are trigonal GLP-1/glucagon/GIP receptor agonists and their medical use, for example in the treatment of disorders of the metabolic syndrome, including diabetes and obesity, as well as for reduction of excess food intake. The compounds of the invention are structurally derived from exendin-4 and show high solubility and stability under acidic conditions in the presence of antimicrobial preservatives like m-cresol or phenol which makes them especially suited for combinations with other antidiabetic compounds.

BACKGROUND OF THE INVENTION

Bhat et al (Diabetologia 2013, 56, 1417-1424), Bhat et al. (Biochem Pharmacol. 2013, 85, 1655-62), Gault et al. (J Biol Chem. 2013, 288, 35581-91) as well as Finan et al. (Nat Med. 2015, 21, 27-36) described trigonal agonists of the glucagon-like peptide-1 (GLP-1), the glucagon and the glucose-dependent insulinotropic polypeptide (GIP) receptors, e.g. by combining the actions of GLP-1, glucagon and GIP in one molecule, which leads to a therapeutic principle with anti-diabetic action and a pronounced weight lowering effect superior to pure GLP-1 agonists, among others due to glucagon-receptor mediated increased satiety and energy expenditure as well as GIP receptor mediated increased insulin secretion.

The amino acid sequence of GLP-1(7-36)-amide is shown as SEQ ID NO: 1.

HAEGTFTSDVSSYLEGQAAKEFIAWLVKGR-NH₂

Liraglutide is a marketed chemically modified GLP-1 analog in which, among other modifications, a fatty acid is linked to a lysine in position 20 leading to a prolonged duration of action (Drucker et al, Nat. Rev. Drug Disc. 2010, 9, 267-268; Buse et al., Lancet 2009, 374, 39-47).

The amino acid sequence of Liraglutide is shown as SEQ ID NO: 2.

HAEGTFTSDVSSYLEGQAAK((S)-4-Carboxy-4-hexadecanoylamino-butyryl) EFIAWLVRGRG-OH

Glucagon is a 29-amino acid peptide which is released into the bloodstream when circulating glucose is low. Glucagon's amino acid sequence is shown as SEQ ID NO: 3.

HSQGTFTSDYSKYLDSRRAQDFVQWLMNT-OH

During hypoglycemia, when blood glucose levels drop below normal, glucagon signals the liver to break down glycogen and release glucose, causing an increase of blood glucose levels to reach a normal level. Recent publications suggest that glucagon has in addition beneficial effects on reduction of body fat mass, reduction of food intake, and increase of energy expenditure (Heppner et al., Physiology & Behavior 2010, 100, 545-548).

GIP (glucose-dependent insulinotropic polypeptide) is a 42 amino acid peptide that is released from intestinal K-cells following food intake. GIP and GLP-1 are the two gut enteroendocrine cell-derived hormones accounting for the incretin effect, which accounts for over 70% of the insulin response to an oral glucose challenge (Baggio et al. Gastroenterology 2007, 132, 2131-2157).

GIP's amino acid sequence is shown as SEQ ID NO: 5.

YAEGTFISDYSIAMDKIHQQDFVNWLLAQKGKKNDWKHNITQ-OH

Peptides which are based on the structures of GLP-1 or glucagon, and bind and activate the GLP-1, the glucagon and the GIP receptor have been described in patent applications WO 2010/011439, WO 2010/148089, WO 2012/088116, WO 2013/192129, WO 2013/192130, WO 2014/049610, and WO 2015/067716. Further trispecific agonists based on exendin-4 have been described in WO 2014/096145, WO 2015/086731, WO 2015/086732, WO 2015/086733, WO 2015/155141 and PCT/EP2016/063332. The compounds described therein have been shown to lead to improved glycemic control, possible islet and beta-cell preservation and enhanced body weight loss.

Peptides which bind and activate both the GIP and the GLP-1 receptor designed as analogues of exendin-4 and substituted with a fatty acid side chain are described in patent applications WO 2014/096145 A1, WO 2014/096150 A1, WO 2014/096149 A1, and WO 2014/096148 A1.

Exendin-4 is a 39 amino acid peptide which is produced by the salivary glands of the Gila monster (Heloderma suspectum). Exendin-4 is an activator of the GLP-1 receptor, whereas it shows low activation of the GIP receptor and does not activate the glucagon receptor (see Table 1).

TABLE 1

Potencies of exendin-4 at human GLP-1, GIP and Glucagon receptors (indicated in pM) at increasing concentrations and measuring the formed cAMP as described in Methods.

| SEQ ID NO: | peptide | EC50 hGLP-1 R [pM] | EC50 hGIP R [pM] | EC50 hGlucagon R [pM] |
|---|---|---|---|---|
| 4 | exendin-4 | 0.4 | 12500.0 | >10000000 |

The amino acid sequence of exendin-4 is shown as SEQ ID NO: 4.

HGEGTFTSDLSKQMEEEAVRLFIEWLKNGGPSSGAPPPS-NH2

Exendin-4 shares many of the glucoregulatory actions observed with GLP-1. Clinical and nonclinical studies have shown that exendin-4 has several beneficial antidiabetic properties including a glucose dependent enhancement in insulin synthesis and secretion, glucose dependent suppression of glucagon secretion, slowing down gastric emptying, reduction of food intake and body weight, and an increase in beta-cell mass and markers of beta cell function.

These effects may be beneficial not only for diabetics but also for patients suffering from obesity. Patients with obesity have a higher risk of getting diabetes, hypertension, hyperlipidemia, cardiovascular and musculoskeletal diseases.

Relative to GLP-1, exendin-4 is resistant to cleavage by dipeptidyl peptidase-4 (DPP4) resulting in a longer half-life and duration of action in vivo (Eng J., Diabetes, 1996, 45 (Suppl 2):152A (abstract 554)).

Exendin-4 was also shown to be much more stable towards degradation by neutral endopeptidase (NEP), when compared to GLP-1, glucagon or oxyntomodulin (Druce et al., Endocrinology, 2009, 150(4), 1712-1722). Nevertheless, exendin-4 is chemically labile due to methionine oxidation in position 14 (Hargrove et al., Regul. Pept., 2007, 141, 113-119) as well as deamidation and isomerization of asparagine in position 28 (WO 2004/035623).

Bloom et al. (WO 2006/134340) disclose that peptides which bind and activate both the glucagon and the GLP-1 receptor can be constructed as hybrid molecules from glucagon and exendin-4, where the N-terminal part (e.g. residues 1-14 or 1-24) originates from glucagon and the C-terminal part (e.g. residues 15-39 or 25-39) originates from exendin-4. Such peptides comprise glucagon's amino acid motif YSKY in position 10-13. Krstenansky et al (Biochemistry, 1986, 25, 3833-3839) show the importance of these residues 10-13 of glucagon for its receptor interactions and activation of adenylate cyclase.

Compared to GLP-1, glucagon and oxyntomodulin, exendin-4 has beneficial physicochemical properties, such as solubility and stability in solution and under physiological conditions (including enzymatic stability towards degradation by enzymes, such as DPP4 or NEP), which results in a longer duration of action in vivo.

Nevertheless, also exendin-4 has been shown to be chemically labile due to methionine oxidation in position 14 as well as deamidation and isomerization of asparagine in position 28. Stability might be further improved by substitution of methionine at position 14 and the avoidance of sequences that are known to be prone to degradation via aspartimide formation, especially Asp-Gly or Asn-Gly at positions 28 and 29.

DESCRIPTION OF THE INVENTION

In the compounds of the present invention, several of the underlying residues are different from glucagon and the peptides described in WO 2006/134340. In particular residues Tyr10 and Tyr13, which are known to contribute to the fibrillation of glucagon (J S Pedersen et al., Biochemistry, 2006, 45, 14503-14512) are replaced by Leu. This replacement, especially in combination with isoleucine in position 23 and glutamate in position 24, leads to exendin-4 derivatives with potentially improved biophysical properties as solubility or aggregation behaviour in solution. The replacement of an aromatic amino acid with an aliphatic amino acid in position 13 of an exendin-4 analogue leads to peptides with high activity on both the glucagon and the GIP receptor, keeping their activity on the GLP-1 receptor.

Native exendin-4 is a pure GLP-1 receptor agonist without activity on the glucagon receptor and low activity on the GIP receptor. The compounds of the invention are based on the structure of native exendin-4 but differing at fourteen or more positions as compared to SEQ ID NO: 4 wherein the differences contribute to the enhancement of the agonistic activity at the glucagon receptor and the GIP receptor. Among other substitutions—methionine at position 14 is replaced by an amino acid carrying an —NH$_2$ group in the side-chain, which is further substituted by a lipophilic residue (e.g. a fatty acid combined with a linker). Further the replacement of the exendin-4 amino acids at positions 13, 19, 20, 32, 34, 35 and 39 with a Leu in position 13, a Gln in position 19, an Aib or Lys amino acid in position 20, an Aib in position 34, Pro at position 32 and Lys at position 35 and 39 leads to high activity on both the glucagon as well as the GIP receptor while keeping the high activity on the GLP-1 receptor. These peptides also show high chemical stability, solubility and physical stability at acidic pH values, such as pH 4.5.

Compounds of the invention have the formula I:

H$_2$N-His-Aib-His-Gly-Thr-Phe-Thr-Ser-Asp-Leu-Ser-
Lys-Leu-X14-Glu-Glu-Gln-Arg-Gln-X20-Glu-
Phe-Ile-Glu-Trp-Leu-Lys-Ala-X29-Gly-X31-
Pro-Ser-Aib-Lys-Pro-Pro-Pro-Lys-R$^1$    I wherein
X14 represents an amino acid residue with a functionalized —NH$_2$ side chain group, selected from the group consisting of Lys, Orn, Dab, or Dap, wherein the —NH$_2$ side chain group is functionalized by —Z—C(O)—R$^5$, wherein
Z represents a linker in all stereoisomeric forms and
R$^5$ is a moiety comprising up to 50 carbon atoms and heteroatoms selected from N and O,
X20 represents an amino acid residue selected from Aib and Lys,
X29 represents an amino acid residue selected from D-Ala and Gly,
X31 represents an amino acid residue selected from His and Pro,
R$^1$ is NH$_2$ or OH,
or a salt or solvate thereof.

The compounds of the invention are GLP-1, glucagon and GIP receptor agonists as determined by the observation that they are capable of stimulating intracellular cAMP formation in the assay system described in Methods.

According to another embodiment the compounds of the invention, particularly with a lysine at position 14 which is further substituted with a lipophilic residue, exhibit at least a relative activity of 0.1% (i.e. EC$_{50}$<700 pM), more preferably of 1% (i.e. EC$_{50}$<70 pM), more preferably of 3.5% (i.e. EC$_{50}$<20 pM) and even more preferably of 7% (i.e. EC$_{50}$<10 pM) compared to that of GLP-1(7-36)amide at the GLP-1 receptor.

Furthermore, the compounds of the invention exhibit at least a relative activity of 0.1% (i.e. EC$_{50}$<500 pM), more preferably of 0.5% (i.e. EC$_{50}$<100 pM), more preferably of 1% (<50 pM) and even more preferably of 5% (i.e. EC$_{50}$<10 pM) compared to that of natural glucagon at the glucagon receptor. Furthermore, the compounds of the invention exhibit at least a relative activity of 0.1% (i.e. EC$_{50}$<400 pM), more preferably of 0.4% (i.e. EC$_{50}$<100 pM), more preferably of 1% (<40 pM) and even more preferably of 4% (i.e. EC$_{50}$<10 pM) compared to that of natural GIP at the GIP receptor.

The term "activity" as used herein preferably refers to the capability of a compound to activate the human GLP-1 receptor, the human glucagon receptor and the human GIP receptor. More preferably the term "activity" as used herein refers to the capability of a compound to stimulate intracellular cAMP formation. The term "relative activity" as used herein is understood to refer to the capability of a compound to activate a receptor in a certain ratio as compared to another receptor agonist or as compared to another receptor. The activation of the receptors by the agonists (e.g. by measuring the cAMP level) is determined as described herein, e.g. as described in the examples.

The compounds of the invention preferably have an EC$_{50}$ for hGLP-1 receptor of 450 pM or less, preferably of 200 pM or less, more preferably of 100 pM or less, more preferably of 50 pM or less, more preferably of 25 pM or less, more preferably of 10 pM or less, more preferably of 8 pM or less, and more preferably of 5 pM or less and an EC$_{50}$ for hGlucagon receptor of 450 pM or less, preferably of 200 pM or less, more preferably of 100 pM or less, more preferably of 50 pM or less, more preferably of 25 pM or less, more preferably of 10 pM or less, more preferably of 8 pM or less, and more preferably of 5 pM or less and an EC$_{50}$ for hGIP receptor of 450 pM or less, preferably of 200 pM or less, more preferably of 100 pM or less, more preferably of 50 pM or less, more preferably of 25 pM or less, more preferably of 10 pM or less, more preferably of 8 pM or less, and more preferably of 5 pM or less. The $EC_{50}$ for the hGLP-1 receptor, the hGlucagon receptor and the hGIP receptor may be determined as described in the Methods herein and as used to generate the results described in examples.

Compounds of the formula I particularly those with a lysine at position 14 which is further substituted with a lipophilic residue, showed increased glucagon receptor activation compared to derivatives having the original methionine (from exendin-4) or leucine at position 14 (see also WO2014/056872). Furthermore, oxidation (in vitro or in vivo) of methionine is not possible anymore.

The compounds of formula I do not only show high activity on the glucagon receptor but as well on the GIP receptor. The additional high activity on the GIP receptor is intended for enhanced efficacy on blood glucose control compared to pure GLP-1 receptor agonism and to reduce the probability of GLP-1 related side effects like gastrointestinal distress as the contribution of the GLP-1 part can be reduced. The additional GIPR activity is also intended to counterbalance a potential glucose increase by glucagon receptor activation therefore allowing higher glucagon receptor activity as observed in compounds of formula I (Finan et al. Nat Med. 2015, 21, 27-36).

In one embodiment the compounds of the invention have a high solubility at acidic and/or physiological pH values in the presence of an antimicrobial preservative like phenol or m-cresol, e.g., at an acidity range from pH 4 to 5, especially pH 4.5 and/or a more physiological range from pH 6 to 8, especially at pH 7.4 at 25° C. or 40° C., in another embodiment at least 1 mg/ml and in a particular embodiment at least 5 mg/ml.

Furthermore, the compounds of the invention preferably have a high stability when stored in solution in the presence of an antimicrobial preservative like phenol or m-cresol. Preferred assay conditions for determining the stability is storage for 28 days at 25° C. or 40° C. in solution at an acidity range from pH 4 to 5, especially pH 4.5. The stability of peptides is determined by chromatographic analyses as described in the Methods. Preferably, after 28 days at 40° C. in solution at pH 4.5 the purity loss is no more than 20%, more preferably no more than 15% and even more preferably no more than 12%.

In one embodiment the compounds of the invention show a hydrodynamic radius $R_h$ of 5 nm or less at concentrations of 1 mg/ml in the presence of an antimicrobial preservative like phenol or m-cresol, e.g., at an acidity range from pH 4 to 5 at 25° C., especially pH 4.5 at 25° C. as assayed by dynamic light scattering as described in Methods.

In one embodiment the compounds of the invention do not show an increase in fluorescence intensity with Thioflavin T as fluorescence probe at concentrations of 3 mg/ml in the presence of an antimicrobial preservative like phenol or m-cresol, e.g., at an acidity range from pH 4 to 5, especially pH 4.5 at 37° C. over 5 hours, more preferably over 10 hours, more preferably over 20 hours, more preferably over 30 hours, more preferably over 40 hours and even more preferably over 45 hours as assayed by the ThT assay as described in Methods.

In one embodiment the compounds of this invention are more resistant to cleavage by neutral endopeptidase (NEP) and dipeptidyl peptidase-4 (DPP4), resulting in a longer half-life and duration of action in vivo, when compared with native GLP-1 and glucagon.

In one embodiment the compounds of the present invention comprise a peptide moiety which is a linear sequence of 39 amino carboxylic acids, particularly α-amino carboxylic acids linked by peptide, i.e. carboxamide bonds.

In one embodiment, $R^1$ is $NH_2$.

Specific preferred examples for —Z—C(O)—$R^5$ groups are listed in the following Table 2, which are selected from (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl, (4S)-Carboxy-[2-(2-{2-[(4R)-5-carboxy-4-hexadecanoylamino-pentanoylamino]-ethoxy}-ethoxy)-acetylamino]-butyryl, (4S)-Carboxy-[2-(2-{2-[(4R)-5-carboxy-4-hexadecanoylamino-pentanoylamino]-ethoxy}-ethoxy)-acetylamino]-butyryl, (2-{2-[2-(2-{2-[(4S)-4-Carboxy-4-hexadecanoylamino-butyrylamino]-ethoxy}-ethoxy)-acetylamino]-ethoxy}-ethoxy)-acetyl, (2-{2-[2-(2-{2-[(4S)-4-Carboxy-4-octadecanoylamino-butyrylamino]-ethoxy}-ethoxy)-acetylamino]-ethoxy}-ethoxy)-acetyl, [2-(2-{2-[2-(2-{2-[2-(2-Octadecanoylamino-ethoxy)-ethoxy]-acetylamino}-ethoxy)-ethoxy]-acetylamino}-ethoxy)-ethoxy]-acetyl-.

Further preferred are stereoisomers, particularly enantiomers of these groups, either S— or R-enantiomers. The term "R" in Table 2 is intended to mean the attachment site of —Z—C(O)—$R^5$ at the peptide back bone, for example the epsilon-amino group of Lys.

TABLE 2

| Structure/IUPAC | name |
|---|---|
| (S)-4-Carboxy-4-octadecanoylamino-butyryl- | gGlu-Stea |

TABLE 2-continued

| Structure/IUPAC | name |
|---|---|
| 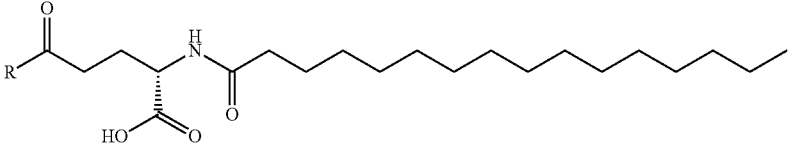<br>(S)-4-Carboxy-4-hexadecanoylamino-butyryl- | gGlu-Palm |
| 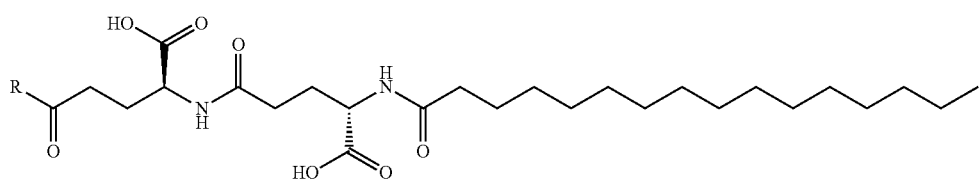<br>(S)-4-Carboxy-4-((S)-4-carboxy-4-hexadecanoylamino-butyrylamino)-butyryl- | gGlu-gGlu-Palm |
| 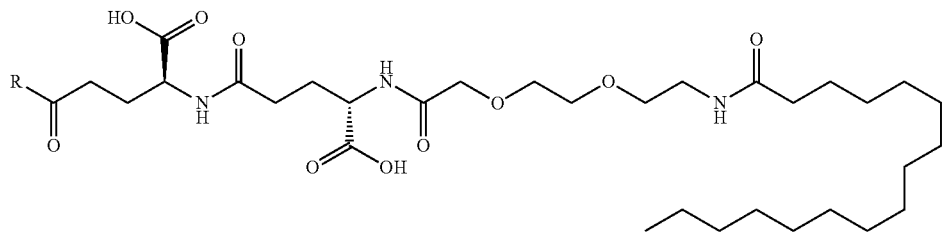<br>[[(4S)-4-carboxy-4-[[(4S)-4-carboxy-4-[[2-[2-[2-(hexadecanoylamino)ethoxy]ethoxy]acetyl]amino]butyrylamino]-butyryl- | gGlu-gGlu-AEEAc-Palm |
| 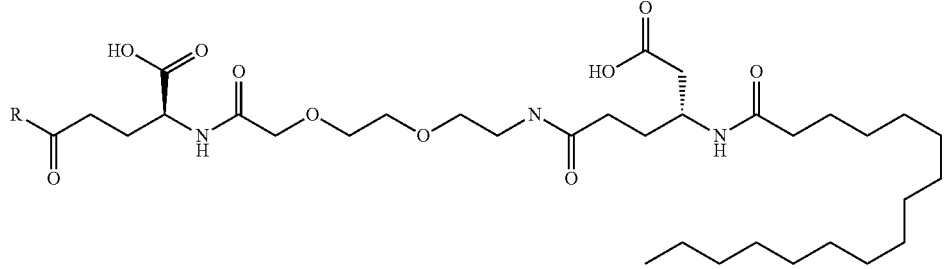<br>(4S)-Carboxy-[2-(2-{2-[(4R)-5-carboxy-4-hexadecanoylamino-pentanoylamino]-ethoxy}-ethoxy)-acetylamino]-butyryl | gGlu-AEEAc-gAAA-Palm |
| 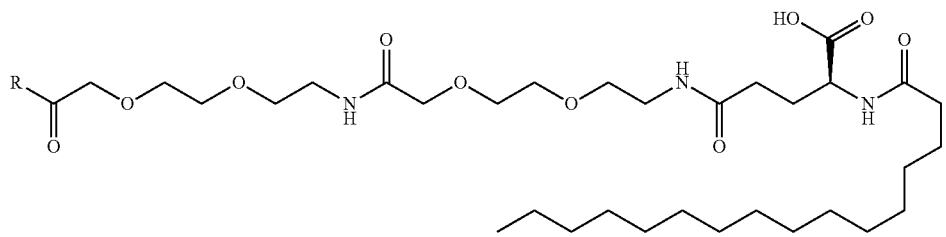<br>(2-{2-[2-(2-{2-[(4S)-4-Carboxy-4-hexadecanoylamino-butyrylamino]-ethoxy}-ethoxy)-acetylamino]-ethoxy}-ethoxy)-acetyl | AEEAc-AEEAc-gGlu-Palm |

TABLE 2-continued

| Structure/IUPAC | name |
|---|---|
| (2-{2-[2-(2-{2-[(4S)-4-Carboxy-4-octadecanoylamino-butyrylamino]-ethoxy}-ethoxy)-acetylamino]-ethoxy}-ethoxy)-acetyl | AEEAc-AEEAc-gGlu-Stea |
| [2-(2-{2{2-(2-{2-[2-(2-Octadecanoylamino-ethoxy)-ethoxy]-acetylamino}-ethoxy)-ethoxy]-acetylamino}-ethoxy)-ethoxy]-acetyl- | AEEAc-AEEAc-AEEAc-Stea |

A further embodiment relates to compounds of formula I, wherein
- X14 represents Lys wherein the —NH$_2$ side chain group is functionalized with a group —Z—C(O)R$^5$, wherein
- Z represents a group selected from gGlu, gGlu-gGlu, gGlu-AEEAc-gAAA-, gGlu-gGlu-AEEAc, AEEAc-AEEAc-gGlu and AEEAc-AEEAc-AEEAc; and
- R$^5$ represents a group selected from pentadecanyl or heptadecanyl.

A further embodiment relates to compounds of formula I, wherein
- X14 represents Lys wherein the —NH$_2$ side chain group is functionalized with a group —Z—C(O)R$^5$, wherein
- Z represents a group selected from gGlu, gGlu-gGlu, gGlu-AEEAc-gAAA- and gGlu-gGlu-AEEAc; and
- R$^5$ represents a group selected from pentadecanyl or heptadecanyl.

A further embodiment relates to compounds of formula I, wherein
- X14 represents Lys wherein the —NH$_2$ side chain group is functionalized by (S)—4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (2-{2-[2-(2-{2-[(4S)-4-Carboxy-4-hexadecanoylamino-butyrylamino]-ethoxy}-ethoxy)-acetylamino]-ethoxy}-ethoxy)-acetyl, (2-{2-[2-(2-{2-[(4S)-4-Carboxy-4-octadecanoylamino-butyrylamino]-ethoxy}-ethoxy)-acetylamino]-ethoxy}-ethoxy)-acetyl, [2-(2-{2-[2-(2-{2-[2-(2-Octadecanoylamino-ethoxy)-ethoxy]-acetylamino}-ethoxy)-ethoxy]-acetylamino}-ethoxy)-ethoxy]-acetyl-,
- R$^1$ represents NH$_2$, or a salt or solvate thereof.

A further embodiment relates to compounds of formula I, wherein
- X14 represents Lys wherein the —NH$_2$ side chain group is functionalized by (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (2-{2-[2-(2-{2-[(4S)-4-Carboxy-4-hexadecanoylamino-butyrylamino]-ethoxy}-ethoxy)-acetylamino]-ethoxy}-ethoxy)-acetyl, (2-{2-[2-(2-{2-[(4S)-4-Carboxy-4-octadecanoylamino-butyrylamino]-ethoxy}-ethoxy)-acetylamino]-ethoxy}-ethoxy)-acetyl,
- R$^1$ represents NH$_2$, or a salt or solvate thereof.

A further embodiment relates to compounds of formula I, wherein
- X14 represents Lys wherein the —NH$_2$ side chain group is functionalized by (S)-4-Carboxy-4-((S)-4-carboxy-4-hexadecanoylamino-butyrylamino)-butyryl-,
- X20 represents Lys or Aib,
- X29 represents an amino acid residue selected from D-Ala and Gly,
- X31 represents an amino acid residue selected from His and Pro,
- R$^1$ represents NH$_2$, or a salt or solvate thereof.

A further embodiment relates compounds of formula I, wherein
- X14 represents Lys wherein the —NH$_2$ side chain group is functionalized by (S)-4-Carboxy-4-((S)-4-carboxy-4-hexadecanoylamino-butyrylamino)-butyryl-, (S)-4-Carboxy-4-octadecanoylamino-butyryl-,
- X20 represents Lys,
- X29 represents an amino acid residue selected from D-Ala and Gly,
- X31 represents an amino acid residue selected from His and Pro,
- R$^1$ represents NH$_2$, or a salt or solvate thereof.

A further embodiment relates to compounds of formula I, wherein
- X14 represents Lys wherein the —NH$_2$ side chain group is functionalized by (S)-4-Carboxy-4-((S)-4-carboxy- 4-hexadecanoylamino-butyrylamino)-butyryl-, (S)-4-Carboxy-4-octadecanoylamino-butyryl-,
X20 represents Lys,
X29 represents an amino acid residue selected from D-Ala and Gly,
X31 represents His,
$R^1$ represents $NH_2$,
or a salt or solvate thereof.

A further embodiment relates to compounds of formula I, wherein
X14 represents Lys wherein the —$NH_2$ side chain group is functionalized by (S)-4-Carboxy-4-((S)-4-carboxy-4-hexadecanoylamino-butyrylamino)-butyryl-, (S)-4-Carboxy-4-octadecanoylamino-butyryl-,
X20 represents Lys,
X29 represents Gly,
X31 represents an amino acid residue selected from His and Pro,
$R^1$ represents $NH_2$,
or a salt or solvate thereof.

A further embodiment relates to compounds of formula I, wherein
X14 represents Lys wherein the —$NH_2$ side chain group is functionalized by (S)-4-Carboxy-4-((S)-4-carboxy-4-hexadecanoylamino-butyrylamino)-butyryl-, (S)-4-Carboxy-4-octadecanoylamino-butyryl-,
X20 represents Aib,
X29 represents an amino acid residue selected from D-Ala and Gly,
X31 represents an amino acid residue selected from His and Pro,
$R^1$ represents $NH_2$,
or a salt or solvate thereof.

A further embodiment relates to compounds of formula I, wherein
X14 represents Lys wherein the —$NH_2$ side chain group is functionalized by (S)-4-Carboxy-4-((S)-4-carboxy-4-hexadecanoylamino-butyrylamino)-butyryl-, (S)-4-Carboxy-4-octadecanoylamino-butyryl-,
X20 represents Aib,
X29 represents an amino acid residue selected from D-Ala and Gly,
X31 represents Pro,
$R^1$ represents $NH_2$,
or a salt or solvate thereof.

A further embodiment relates to compounds of formula I, wherein
X14 represents Lys wherein the —$NH_2$ side chain group is functionalized by (S)-4-Carboxy-4-((S)-4-carboxy-4-hexadecanoylamino-butyrylamino)-butyryl-,
X20 represents Aib,
X29 represents D-Ala,
X31 represents an amino acid residue selected from His and Pro,
$R^1$ represents $NH_2$,
or a salt or solvate thereof.

Specific examples of compounds of formula I are the compounds of SEQ ID NO: 6-27, as well as salts or solvates thereof.

Specific examples of compounds of formula I are the compounds of SEQ ID NO: 6, 9 and 11 as well as salts or solvates thereof.

A specific example of compounds of formula I is the compounds of SEQ ID NO: 6, well as salts or solvates thereof.

A specific example of compounds of formula I is the compounds of SEQ ID NO: 9, well as salts or solvates thereof.

A specific example of compounds of formula I is the compounds of SEQ ID NO: 11, well as salts or solvates thereof.

In a further aspect, the present invention relates to a composition comprising a compound of the invention in admixture with a carrier. In preferred embodiments, the composition is a pharmaceutically acceptable composition and the carrier is a pharmaceutically acceptable carrier. The compounds of the invention may be in the form of a salt, e.g. a pharmaceutically acceptable salt or a solvate, e.g. a hydrate. In still a further aspect, the present invention relates to a composition for use in a method of medical treatment, particularly in human medicine.

The compounds of formula I are suitable for human treatment without an additional therapeutically effective agent. In other embodiments, however, the compounds may be used together with at least one additional therapeutically active agent, as described in "combination therapy".

The compounds of formula I are particularly suitable for the treatment or prevention of diseases or disorders caused by, associated with and/or accompanied by disturbances in carbohydrate and/or lipid metabolism, e.g. for the treatment or prevention of hyperglycemia, type 2 diabetes, impaired glucose tolerance, type 1 diabetes, obesity and metabolic syndrome. Further, the compounds of the invention may be suitable for the treatment or prevention of degenerative diseases, particularly neurodegenerative diseases.

The compounds described find use, inter alia, in preventing weight gain or promoting weight loss. By "preventing" is meant inhibiting or reducing when compared to the absence of treatment, and is not necessarily meant to imply complete cessation of a disorder.

The compounds of the invention may cause a decrease in food intake and/or increase in energy expenditure, resulting in the observed effect on body weight.

Independently of their effect on body weight, the compounds of the invention may have a beneficial effect on circulating cholesterol levels, being capable of improving lipid levels, particularly LDL, as well as HDL levels (e.g. increasing HDL/LDL ratio).

Thus, the compounds of the invention may be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for treatment and prevention of the metabolic syndrome, diabetes, hypertension, atherogenic dyslipidemia, atherosclerosis, arteriosclerosis, coronary heart disease, or stroke. Their effects in these conditions may be as a result of or associated with their effect on body weight, or may be independent thereof.

Medical uses include delaying or preventing disease progression in type 2 diabetes, treating metabolic syndrome, treating obesity or preventing overweight, for decreasing food intake, increase energy expenditure, reducing body weight, delaying the progression from impaired glucose tolerance (IGT) to type 2 diabetes; delaying the progression from type 2 diabetes to insulin-requiring diabetes.

Also an embodiment of the invention is a method for the treatment or prevention of a disease or disorder in a patient, the method comprising administering to the patient an effective amount of a compound of formula I or a pharmaceutical composition thereof.

Also an embodiment of the invention is a method for the treatment or prevention of glucose intolerance, insulin resistance, pre-diabetes, increased fasting glucose, hyperglycemia, type 2 diabetes, hypertension, dyslipidemia, arteriosclerosis, coronary heart disease, peripheral artery disease, stroke or any combination of these individual disease components, the method comprising administering to the patient an effective amount of a compound of formula I or a pharmaceutical composition thereof.

Also an embodiment of the invention is a method for control of appetite, feeding and calory intake, increase of energy expenditure, prevention of weight gain, promotion of weight loss, reduction of excess body weight and altogether treatment of obesity, including morbid obesity, the method comprising administering to the patient an effective amount of a compound of formula I or a pharmaceutical composition thereof.

Also an embodiment of the invention is a method for the treatment or prevention of hepatosteatosis, the method comprising administering to the patient an effective amount of a compound of formula I or a pharmaceutical composition thereof.

Also an embodiment of the invention is a method for the treatment or prevention of hyperglycemia, type 2 diabetes and/or obesity, the method comprising administering to the patient an effective amount of a compound of formula I or a pharmaceutical composition thereof.

Also an embodiment of the invention is a method for the treatment or prevention of type 2 diabetes and obesity, the method comprising administering to the patient an effective amount of a compound of formula I or a pharmaceutical composition thereof.

Also an embodiment of the invention is a method for the treatment or prevention of diabetes, the method comprising administering to the patient an effective amount of a compound of formula I or a pharmaceutical composition thereof.

Also an embodiment of the invention is a method for the treatment or prevention of is obesity, the method comprising administering to the patient an effective amount of a compound of formula I or a pharmaceutical composition thereof.

Also an embodiment of the invention is a method for the treatment or prevention of atherosclerosis, the method comprising administering to the patient an effective amount of a compound of formula I or a pharmaceutical composition thereof.

Also an embodiment of the invention is a method for reducing the intestinal passage, increasing the gastric content and/or reducing the food intake of a patient, the method comprising administering to the patient an effective amount of a compound of formula I or a pharmaceutical composition thereof.

Also an embodiment of the invention is a method for reducing blood glucose levels and/or reducing HbA1c levels of a patient, the method comprising administering to the patient an effective amount of a compound of formula I or a pharmaceutical composition thereof.

Also an embodiment of the invention is a method for reducing body weight of a patient, the method comprising administering to the patient an effective amount of a compound of formula I or a pharmaceutical composition thereof.

Also an embodiment of the invention is a method for treatment or prevention of a disease or disorder in a patient, the method comprising administering to the patient an effective amount of a compound of formula I or a pharmaceutical composition thereof, wherein the effective amount of at least one compound of formula I and the additional active ingredient are administered to the patient simultaneously.

Also an embodiment of the invention is a method for the treatment or prevention of a disease or disorder in a patient, the method comprising administering to the patient an effective amount of a compound of formula I or a pharmaceutical composition thereof, wherein the effective amount of at least one compound of formula I and the additional active ingredient are administered to the patient sequentially.

Definitions

The amino acid sequences of the present invention contain the conventional one letter and three letter codes for naturally occurring amino acids, as well as generally accepted three letter codes for other amino acids, such as Aib (α-aminoisobutyric acid).

The term "native exendin-4" refers to native exendin-4 having the sequence (SEQ ID NO: 4)
HGEGTFTSDLSKQMEEEAVRLFIEWLKNGGPSSGAPPPS-NH$_2$.

The invention relates to peptidic compounds as defined in formula I.

The peptidic compounds of the present invention comprise a linear backbone of amino carboxylic acids linked by peptide, i.e. carboxamide bonds. Preferably, the amino carboxylic acids are α-amino carboxylic acids and more preferably L-α-amino carboxylic acids, unless indicated otherwise. The peptidic compounds preferably comprise a backbone sequence of 39 amino carboxylic acids.

Amino acids within the peptide moiety (formula I) can be considered to be numbered consecutively from 1 to 39 in the conventional N-terminal to C-terminal direction. Reference to a "position" within peptidic moiety I should be constructed accordingly, as should reference to positions within native exendin-4 and other molecules, e.g., in exendin-4, His is at position 1, Gly at position 2, . . . , Met at position 14, . . . and Ser at position 39.

An amino acid residue with an —NH$_2$ side chain group, e.g. Lys, Orn, Dab or Dap, is functionalized in that at least one H atom of the —NH$_2$ side chain group is replaced by —Z—C(O)—R$^5$, wherein R$^5$ comprises a lipophilic moiety, e.g. an acyclic linear or branched (C$_8$-C$_{30}$) saturated or unsaturated hydrocarbon group, which is unsubstituted or substituted e.g. by halogen (F, Cl, Br, J), —OH and/or CO$_2$H and Z comprises a linker in all stereoisomeric forms, e.g. a linker comprising one or more, e.g. 1 to 5, preferably 1, 2 or 3 amino acid linker groups selected from the group gamma-Glutamate (gGlu), gAAA and AEEAc. Preferred groups R$^5$ comprise a lipophilic moiety, e.g. an acyclic linear or branched (C$_{12}$-C$_{20}$) saturated or unsaturated hydrocarbon group, e.g. pentadecanyl, hexadecanyl or heptadecanyl, which is unsubstituted or substituted by CO$_2$H, more preferably pentadecanyl, or heptadecanyl. In one embodiment amino acid linker groups are selected from gGlu, gGlu-gGlu, gGlu-gGlu-AEEAc, gGlu-AEEAc-gAAA, AEEAc-AEEAc-gGlu and AEEAc-AEEAc-AEEAc. In another embodiment the amino acid linker group is gGlu. In another embodiment the amino acid linker group is gGlu-gGlu. In another embodiment the amino acid linker group is gGlu-gGlu-AEEAc. In another embodiment the amino acid linker group is gGlu-AEEAc-gAAA. In another embodiment the amino acid linker group is AEEAc-AEEAc-gGlu. In another embodiment the amino acid linker group is AEEAc-AEEAc-AEEAc.

In a further aspect, the present invention relates to a composition comprising a compound of the invention as described herein, or a salt or solvate thereof, in admixture with a carrier.

The invention also relates to the use of a compound of the present invention for use as a medicament, particularly for the treatment of a condition as described in the specification.

The invention also relates to a composition wherein the composition is a pharmaceutically acceptable composition, and the carrier is a pharmaceutically acceptable carrier.

Peptide Synthesis

The skilled person is aware of a variety of different methods to prepare peptides. These methods include but are not limited to synthetic approaches and recombinant gene expression. Thus, one way of preparing peptides is the synthesis in solution or on a solid support and subsequent isolation and purification. A different way of preparing the peptides is gene expression in a host cell in which a DNA sequence encoding the peptide has been introduced. Alternatively, the gene expression can be achieved without utilizing a cell system. The methods described above may also be combined in any way.

A preferred way to prepare the compounds of the present invention is solid phase synthesis on a suitable resin. Solid phase peptide synthesis is a well-established methodology (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). Solid phase synthesis is initiated by attaching an N-terminally protected amino acid with its carboxy terminus to an inert solid support carrying a cleavable linker. This solid support can be any polymer that allows coupling of the initial amino acid, e.g. a trityl resin, a chlorotrityl resin, a Wang resin or a Rink resin in which the linkage of the carboxy group (or carboxamide for Rink resin) to the resin is sensitive to acid (when Fmoc strategy is used). The polymer support must be stable under the conditions used to deprotect the α-amino group during the peptide synthesis.

After the N-terminally protected first amino acid has been coupled to the solid support, the α-amino protecting group of this amino acid is removed. The remaining protected amino acids are then coupled one after the other or with a preformed dipeptide, tripeptide or tetrapeptide in the order represented by the peptide sequence using appropriate amide coupling reagents, for example BOP, HBTU, HATU or DIC (N,N'-diisopropylcarbodiimide)/HOBt (1-hydroxybenzotriazole), wherein BOP, HBTU and HATU are used with tertiary amine bases. Alternatively, the liberated N-terminus can be functionalized with groups other than amino acids, for example carboxylic acids, etc.

Usually, reactive side-chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999).

In some cases it might be desirable to have side-chain protecting groups that can selectively be removed while other side-chain protecting groups remain intact. In this case the liberated functionality can be selectively functionalized. For example, a lysine may be protected with an ivDde ([1-(4,4-dimethyl-2,6-dioxocyclohex-1-ylidene)-3-methylbutyl) protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side-chain functionalities are protected with acid labile protecting groups, the ivDde group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids. Alternatively, the side chain (as described in table 2) can be introduced together with the lysine during peptide synthesis using a prefunctionalized building block, e.g. (2S)-6-[[(4S)-5-tert-butoxy-4-[[(4S)-5-tert-butoxy-4-(hexadecanoylamino)-5-oxo-pentanoyl]amino]-5-oxo-pentanoyl]amino]-2-(9H-fluoren-9-ylmethoxycarbonylamino)hexanoic acid, as coupling partner.

Finally the peptide is cleaved from the resin. This can be achieved by using King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Potency

As used herein, the term "potency" or "in vitro potency" is a measure for the ability of a compound to activate the receptors for GLP-1, glucagon or GIP in a cell-based assay. Numerically, it is expressed as the "EC50 value", which is the effective concentration of a compound that induces a half maximal increase of response (e.g. formation of intracellular cAMP) in a dose-response experiment.

Therapeutic Uses

Metabolic syndrome is a combination of medical disorders that, when occurring together, increase the risk of developing type 2 diabetes, as well as atherosclerotic vascular disease, e.g. heart disease and stroke. Defining medical parameters for the metabolic syndrome include diabetes mellitus, impaired glucose tolerance, raised fasting glucose, insulin resistance, urinary albumin secretion, central obesity, hypertension, elevated triglycerides, elevated LDL cholesterol and reduced HDL cholesterol.

Obesity is a medical condition in which excess body fat has accumulated to the extent that it may have an adverse effect on health and life expectancy and due to its increasing prevalence in adults and children it has become one of the leading preventable causes of death in modern world. It increases the likelihood of various other diseases, including heart disease, type 2 diabetes, obstructive sleep apnoe, certain types of cancer, as well as osteoarthritis, and it is most commonly caused by a combination of excess food intake, reduced energy expenditure, as well as genetic susceptibility.

Diabetes mellitus, often simply called diabetes, is a group of metabolic diseases in which a person has high blood sugar levels, either because the body does not produce enough insulin, or because cells do not respond to the insulin that is produced. The most common types of diabetes are: (1) type 1 diabetes, where the body fails to produce insulin; (2) type 2 diabetes (T2DM), where the body fails to use insulin properly, combined with an increase in insulin deficiency over time, and (3) gestational diabetes, where women develop diabetes due to their pregnancy. All forms of diabetes increase the risk of long-term complications, which typically develop after many years. Most of these long-term complications are based on damage to blood vessels and can be divided into the two categories "macrovascular" disease, arising from atherosclerosis of larger blood vessels and "microvascular" disease, arising from damage of small blood vessels. Examples for macrovascular disease conditions are ischemic heart disease, myocardial infarction, stroke and peripheral vascular disease. Examples for microvascular diseases are diabetic retinopathy, diabetic nephropathy, as well as diabetic neuropathy.

The receptors for GLP-1 and GIP as well as glucagon are members of the family of 7-transmembrane-spanning, heterotrimeric G-protein coupled receptors. They are structurally related to each other and share not only a significant level of sequence identity, but have also similar mechanisms of ligand recognition and intracellular signaling pathways.

Similarly, the peptides GLP-1, GIP and glucagon share regions of high sequence identity/similarity. GLP-1 and glucagon are produced from a common precursor, preproglucagon, which is differentially processed in a tissue-specific manner to yield e.g. GLP-1 in intestinal endocrine cells and glucagon in alpha cells of pancreatic islets. GIP is derived from a larger proGIP prohormone precursor and is synthesized and released from K-cells located in the small intestine.

The peptidic incretin hormones GLP-1 and GIP are secreted by intestinal endocrine cells in response to food and account for up to 70% of meal-stimulated insulin secretion. Evidence suggests that GLP-1 secretion is reduced in subjects with impaired glucose tolerance or type 2 diabetes, whereas responsiveness to GLP-1 is still preserved in these patients. Thus, targeting of the GLP-1 receptor with suitable agonists offers an attractive approach for treatment of metabolic disorders, including diabetes. The receptor for GLP-1 is distributed widely, being found mainly in pancreatic islets, brain, heart, kidney and the gastrointestinal tract. In the pancreas, GLP-1 acts in a strictly glucose-dependent manner by increasing secretion of insulin from beta cells. This glucose-dependency shows that activation of GLP-1 receptors is unlikely to cause hypoglycemia. Also the receptor for GIP is broadly expressed in peripheral tissues including pancreatic islets, adipose tissue, stomach, small intestine, heart, bone, lung, kidney, testis, adrenal cortex, pituitary, endothelial cells, trachea, spleen, thymus, thyroid and brain. Consistent with its biological function as incretin hormone, the pancreatic β-cell express the highest levels of the receptor for GIP in humans.

There is some clinical evidence that the GIP-receptor mediated signaling could be impaired in patients with T2DM but the impairment of GIP-action is shown to be reversible and could be restored with improvement of the diabetic status. Of note, the stimulation of insulin secretion by both incretin hormones, GIP and GLP-1, is strictly glucose-dependent ensuring a fail-safe mechanism associated with a low risk for hypoglycemia.

At the beta cell level, GLP-1 and GIP have been shown to promote glucose sensitivity, neogenesis, proliferation, transcription of proinsulin and hypertrophy, as well as anti-apoptosis. A peptide with both agonistic activity for the GLP-1 and the GIP receptor could be anticipated to have additive or synergistic anti-diabetic benefit. Other relevant effects of GLP-1 beyond the pancreas include delayed gastric emptying, increased satiety, decreased food intake, reduction of body weight, as well as neuroprotective and cardioprotective effects. In patients with type 2 diabetes, such extrapancreatic effects could be particularly important considering the high rates of comorbidities like obesity and cardiovascular disease. Further GIP actions in peripheral tissues beyond the pancreas comprise increased bone formation and decreased bone resorption as well as neuroprotective effects which might be beneficial for the treatment of osteoporosis and cognitive defects like Alzheimer's disease.

Glucagon is a 29 amino acid peptide hormone that is produced by pancreatic alpha cells and released into the bloodstream when circulating glucose is low. An important physiological role of glucagon is to stimulate glucose output in the liver, which is a process providing the major counterregulatory mechanism for insulin in maintaining glucose homeostasis in vivo.

Glucagon receptors are however also expressed in extra-hepatic tissues such as kidney, heart, adipocytes, lymphoblasts, brain, retina, adrenal gland and gastrointestinal tract, suggesting a broader physiological role beyond glucose homeostasis. Accordingly, recent studies have reported that glucagon has therapeutically positive effects on energy management, including stimulation of energy expenditure and thermogenesis, accompanied by reduction of food intake and body weight loss. Altogether, stimulation of glucagon receptors might be useful in the treatment of obesity and the metabolic syndrome.

Oxyntomodulin is a peptide hormone consisting of glucagon with an eight amino acids encompassing C-terminal extension. Like GLP-1 and glucagon, it is pre-formed in preproglucagon and cleaved and secreted in a tissue-specific manner by endocrinal cells of the small bowel. Oxyntomodulin is known to stimulate both, the receptors for GLP-1 and glucagon and is therefore the prototype of a dual agonist (see Pocai, Molecular Metabolism 2013; 3:241-51).

As GLP-1 and GIP are known for their anti-diabetic effects, GLP-1 and glucagon are both known for their food intake-suppressing effects and glucagon is also a mediator of additional energy expenditure, it is conceivable that a combination of the activities of the three hormones in one molecule can yield a powerful medication for treatment of the metabolic syndrome and in particular its components diabetes and obesity.

Accordingly, the compounds of the invention may be used for treatment of glucose intolerance, insulin resistance, pre-diabetes, increased fasting glucose (hyperglycemia), type 2 diabetes, hypertension, dyslipidemia, arteriosclerosis, coronary heart disease, peripheral artery disease, stroke or any combination of these individual disease components.

In addition, they may be used for control of appetite, feeding and calory intake, increase of energy expenditure, prevention of weight gain, promotion of weight loss, reduction of excess body weight and altogether treatment of obesity, including morbid obesity.

The compounds of the invention are agonists for the receptors for GLP-1, GIP and for glucagon (e.g. "trigonal agonists") and may provide therapeutic benefit to address a clinical need for targeting the metabolic syndrome by allowing simultaneous treatment of diabetes and obesity.

Further disease states and health conditions which could be treated with the compounds of the invention are obesity-linked inflammation, obesity-linked gallbladder disease and obesity-induced sleep apnea.

Although all these conditions could be associated directly or indirectly with obesity, the effects of the compounds of the invention may be mediated in whole or in part via an effect on body weight, or independent thereof.

Further, diseases to be treated may be neurodegenerative diseases such as Alzheimer's disease or Parkinson's disease, or other degenerative diseases as described above.

In one embodiment the compounds are useful in the treatment or prevention of hyperglycemia, type 2 diabetes and/or obesity.

The compounds of the invention may have the ability to reduce the intestinal passage, increase the gastric content and/or to reduce the food intake of a patient. These activities of the compounds of the invention can be assessed in animal models known to the skilled person and also described herein in the Methods.

The compounds of the invention have the ability to reduce blood glucose level, and/or to reduce HbA1c levels of a patient. These activities of the compounds of the invention can be assessed in animal models known to the skilled person and also described herein in the Methods and in examples.

The compounds of the invention may have the ability to reduce body weight of a patient. These activities of the compounds of the invention can be assessed in animal models known to the skilled person and also described herein in the Methods and in examples.

The compounds of the invention may be useful in the treatment or prevention of hepatosteatosis, preferably non-alcoholic liver-disease (NAFLD) and non-alcoholic steatohepatitis (NASH).

Pharmaceutical Compositions

The term "pharmaceutical composition" indicates a mixture containing ingredients that are compatible when mixed and which may be administered. A pharmaceutical composition may include one or more medicinal drugs. Additionally, the pharmaceutical composition may include carriers, buffers, acidifying agents, alkalizing agents, solvents, adjuvants, tonicity adjusters, emollients, expanders, preservatives, physical and chemical stabilizers e.g. surfactants, antioxidants and other components, whether these are considered active or inactive ingredients. Guidance for the skilled in preparing pharmaceutical compositions may be found, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical Excipients, PhP, May 2013 update.

The exendin-4 peptide derivatives of the present invention, or salts thereof, are administered in conjunction with an acceptable pharmaceutical carrier, diluent, or excipient as part of a pharmaceutical composition.

A "pharmaceutically acceptable carrier" is a carrier which is physiologically acceptable (e.g. physiologically acceptable pH) while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro A. R., 2000, Lippencott Williams & Wilkins and in R. C. Rowe et al (Ed), Handbook of Pharmaceutical excipients, PhP, May 2013 update. One exemplary pharmaceutically acceptable carrier is physiological saline solution.

In one embodiment carriers are selected from the group of buffers (e.g. citrate/citric acid, acetate/acetic acid), acidifying agents (e.g. hydrochloric acid), alkalizing agents (e.g. sodium hydroxide), preservatives (e.g. phenol, m-cresol), co-solvents (e.g. polyethylene glycol 400), tonicity adjusters (e.g. mannitol, glycerol), stabilizers (e.g. surfactant, antioxidants, amino acids).

Concentrations used are in a range that is physiologically acceptable.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

The term "pharmaceutically acceptable salt" means salts of the compounds of the invention which are safe and effective for use in mammals.

The term "solvate" means complexes of the compounds of the invention or salts thereof with solvent molecules, e.g. organic solvent molecules and/or water.

In the pharmaceutical composition, the exendin-4 derivative can be in monomeric or oligomeric form.

The term "therapeutically effective amount" of a compound refers to a nontoxic but sufficient amount of the compound to provide the desired effect. The amount of a compound of the formula I necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation. For example the "therapeutically effective amount" of a compound of the formula I is about 0.01 to 50 mg/dose, preferably 0.02 to 1 mg/dose.

Pharmaceutical compositions of the invention are those suitable for parenteral (for example subcutaneous, intramuscular, intradermal or intravenous), rectal, topical and peroral (for example sublingual) administration, although the most suitable mode of administration depends in each individual case on the nature and severity of the condition to be treated and on the nature of the compound of formula I used in each case. In one embodiment, application is parenteral, e.g. subcutaneous.

In case of parenteral application, it could be favorable for the corresponding formulations to include at least one antimicrobial preservative in order to inhibit the growth of microbes and bacteria between administrations. Preferred preservatives are benzylic alcohol or phenolic compounds like phenol or m-cresol. It has been described that these ingredients can induce aggregation for peptides and proteins leading to lower solubility and stability in the formulation (see R. L. Bis et al., Int. J. Pharm. 472, 356-361, 2014; T. J. Kamerzell, Adv. Drug Deliv. Rev., 63, 1118-1159, 2011).

Suitable pharmaceutical compositions may be in the form of separate units, for example capsules, tablets and powders in vials or ampoules, each of which contains a defined amount of the compound; as powders or granules; as solution or suspension in an aqueous or non-aqueous liquid; or as an oil-in-water or water-in-oil emulsion. It may be provided in single or multiple dose injectable form, for example in the form of a pen. The compositions may, as already mentioned, be prepared by any suitable pharmaceutical method which includes a step in which the active ingredient and the carrier (which may consist of one or more additional ingredients) are brought into contact.

In certain embodiments the pharmaceutical composition may be provided together with a device for application, for example together with a syringe, an injection pen or an autoinjector. Such devices may be provided separate from a pharmaceutical composition or prefilled with the pharmaceutical composition.

Administration Unit, Package, Pen Device and Administration

The compound(s) of the present invention can be prepared for use in suitable pharmaceutical compositions. The suitable pharmaceutical compositions may be in the form of one or more administration units.

The compositions may be prepared by any suitable pharmaceutical method which includes a step in which the compound(s) of the present invention and the carrier (which may consist of one or more additional ingredients) are brought into contact.

The administration units may be for example capsules, tablets, dragées, granules sachets, drops, solutions, suspensions, lyophylisates and powders, each of which contains a defined amount of the compound(s) of the present invention.

Each of the above-mentioned administration units of the compound(s) of the invention or pharmaceutical composition of the invention (administration units) may be provided in a package for easy transport and storage. The administration units are packaged in standard single or multi-dosage packaging, their form, material and shape depending on the type of units prepared.

For example, tablets and other forms of solid administration units can be packaged in single units, and the single packaged units can be packaged in multi-pack containers. Liquid formulations can be packaged in single units, such as e.g. vials, cartridges, syringes/prefilled syringes, infusion bags, collapsible plastic bags, infusion bottles, blow-filled seal bottles or infusion tubings or in single or multiple dose injectable form, for example in the form of a pen device, pump or syringe and the single packaged units can be packaged in multi-pack containers. A single package may comprise only one or a plurality of administration units. The package may for example be made of paper, cardboard, paperboard, plastic, metal, combinations or laminates of one or more of paper, plastics and metal, or glass. Exemplary embodiments are blister packages containing e.g. tablets or capsules, which in turn may be provided inside a cardboard box, aluminum barrier laminate sachets containing e.g. a powder, glass or plastic bottles containing e.g. tablets or a solution, or vials, cartridges, syringes, infusion bags, infusion bottles, infusion tubings or ampoules containing a solution or suspension.

In certain embodiments administration units may be provided together with a device for application, for example together with a syringe, an injection pen or an autoinjector. Such devices may be provided separate from a pharmaceutical composition or prefilled with the pharmaceutical composition.

A "pen-type injection device", often briefly referred to as "injection pen", is typically an injection device having an elongated shape that resembles to a fountain pen for writing. Although such pens usually have a tubular cross-section, they could easily have a different cross-section such as triangular, rectangular or square or any variation around these geometries. Generally, pen-type injection devices comprise three primary elements: a cartridge section that includes a cartridge often contained within a housing or holder; a needle assembly connected to one end of the cartridge section; and a dosing section connected to the other end of the cartridge section. The cartridge, often also referred to as "ampoule", typically includes a reservoir that is filled with a medication, a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

Combination Therapy

The compounds of the present invention, trigonal agonists for the GLP-1, GIP and glucagon receptors, can be widely combined with other pharmacologically active compounds, such as all drugs mentioned in the Rote Liste 2016, e.g. with all weight-reducing agents or appetite suppressants mentioned in the Rote Liste 2016, chapter 1, all lipid-lowering agents mentioned in the Rote Liste 2016, chapter 58, all antihypertensives and nephroprotectives, mentioned in the Rote Liste 2016, or all diuretics mentioned in the Rote Liste 2016, chapter 36.

The active ingredient combinations can be used especially for a synergistic improvement in action. They can be applied either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Other active substances which are suitable for such combinations include in particular those which for example potentiate the therapeutic effect of one or more active substances with respect to one of the indications mentioned and/or which allow the dosage of one or more active substances to be reduced.

Therapeutic agents which are suitable for combinations include, for example, antidiabetic agents such as:

Insulin and Insulin derivatives, for example: Glargine/Lantus®, 270-330 U/mL of insulin glargine (EP 2387989 A), 300 U/mL of insulin glargine (EP 2387989 A), Glulisin/Apidra®, Detemir/Levemir®, Lispro/Humalog®/Liprolog®, Degludec/DegludecPlus, Aspart, basal insulin and analogues (e.g. LY-2605541, LY2963016, NN1436), PEGylated insulin Lispro, Humulin®, Linjeta, SuliXen®, NN1045, Insulin plus Symlin, PE0139, fast-acting and short-acting insulins (e.g. Linjeta, PH20, NN1218, HinsBet), (APC-002)hydrogel, oral, inhalable, transdermal and sublingual insulins (e.g. Exubera®, Nasulin®, Afrezza, Tregopil, TPM 02, Capsulin, Oral-lyn®, Cobalamin® oral insulin, ORMD-0801, NN1953, NN1954, NN1956, VIAtab, Oshadi oral insulin). Additionally included are also those insulin derivatives which are bonded to albumin or another protein by a bifunctional linker.

GLP-1, GLP-1 analogues and GLP-1 receptor agonists, for example: Lixisenatide/AVE0010/ZP10/Lyxumia, Exenatide/Exendin-4/Byetta/Bydureon/ITCA 650/AC-2993, Liraglutide/Victoza, Semaglutide, Taspoglutide, Syncria/Albiglutide, Dulaglutide, rExendin-4, CJC-1134-PC, PB-1023, TTP-054, Efpeglenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401, MK-8521, MED10382, BHM-034, HM12525A, MOD-6030, CAM-2036, DA-15864, ARI-2651, ARI-2255, LY3298176, NN1177, Exenatide-XTEN and Glucagon-XTEN, NN9030.

DPP-4 inhibitors, for example: Alogliptin/Nesina, Trajenta/Linagliptin/BI-1356/Ondero/Trajenta/Tradjenta/Trayenta/Tradzenta, Saxagliptin/Onglyza, Sitagliptin/Januvia/Xelevia/Tesave/Janumet/Velmetia, Galvus/Vildagliptin, Anagliptin, Gemigliptin, Teneligliptin, Melogliptin, Trelagliptin, DA-1229, Omarigliptin/MK-3102, KM-223, Evogliptin, ARI-2243, PBL-1427, Pinoxacin.

SGLT2 inhibitors, for example: Invokana/Canaglifozin, Forxiga/Dapagliflozin, Remoglifozin, Sergliflozin, Empagliflozin, Ipragliflozin, Tofogliflozin, Luseogliflozin, Sotagliflozin (LX-4211), Ertuglifozin/PF-04971729, RO-4998452, Bexagliflozin (EGT-0001442), KGA-3235/DSP-3235, LIK066, SBM-TFC-039, Henagliflozin (SHR3824), Janagliflozin, Tianagliflozin, AST1935, JRP493, HEC-44616

Biguanides (e.g. Metformin, Buformin, Phenformin), Thiazolidinediones (e.g. Pioglitazone, Rivoglitazone, Rosiglitazone, Troglitazone), dual PPAR agonists (e.g. Aleglitazar, Muraglitazar, Tesaglitazar), Sulfonylureas (e.g. Tolbutamide, Glibenclamide, Glimepiride/Amaryl, Glipizide), Meglitinides (e.g. Nateglinide, Repaglinide, Mitiglinide), Alpha-glucosidase inhibitors (e.g. Acarbose, Miglitol, Voglibose), Amylin and Amylin analogues (e.g. Pramlintide, Symlin).

GPR119 agonists (e.g. GSK-263A, PSN-821, MBX-2982, APD-597, ZYG-19, DS-8500), GPR40 agonists (e.g. Fasiglifam/TAK-875, TUG-424, P-1736, JTT-851, GW9508).

Other suitable combination partners are: Cycloset, inhibitors of 11-beta-HSD (e.g. LY2523199, BMS770767, RG-4929, BMS816336, AZD-8329, HSD-016, BI-135585), activators of glucokinase (e.g. TTP-399, AMG-151, TAK-329, GKM-001), inhibitors of DGAT (e.g. LCQ-908), inhibitors of protein tyrosinephosphatase 1 (e.g. Trodusquemine), inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha 2-antagonists, CCR-2 antagonists, SGLT-1 inhibitors (e.g. LX-2761).

One or more lipid lowering agents are also suitable as combination partners, such as for example: HMG-CoA-reductase inhibitors (e.g. Simvastatin, Atorvastatin), fibrates (e.g. Bezafibrate, Fenofibrate), nicotinic acid and the derivatives thereof (e.g. Niacin), PPAR-(alpha, gamma or alpha/gamma) agonists or modulators (e.g. Aleglitazar), PPAR-delta agonists, ACAT inhibitors (e.g. Avasimibe), cholesterol absorption inhibitors (e.g. Ezetimibe), Bile acid-binding substances (e.g. Cholestyramine), ileal bile acid transport inhibitors, MTP inhibitors, or modulators of PCSK9.

HDL-raising compounds such as: CETP inhibitors (e.g. Torcetrapib, Anacetrapid, Dalcetrapid, Evacetrapid, JTT-302, DRL-17822, TA-8995) or ABC1 regulators.

Other suitable combination partners are one or more active substances for the treatment of obesity, such as for example: Sibutramine, Tesofensine, Orlistat, antagonists of the cannabinoid-1 receptor, MCH-1 receptor antagonists, MC4 receptor agonists, NPY5 or NPY2 antagonists (e.g. Velneperit), beta-3-agonists, leptin or leptin mimetics, agonists of the 5HT2c receptor (e.g. Lorcaserin), or the combinations of bupropione/naltrexone, bupropione/zonisamide, bupropione/phentermine or pramlintide/metreleptin.

Other suitable combination partners are:
Further gastrointestinal peptides such as Peptide YY 3-36 (PYY3-36) or analogues thereof, pancreatic polypeptide (PP) or analogues thereof, glucagon receptor agonists or antagonists, GIP receptor agonists or antagonists, ghrelin antagonists or inverse agonists, Xenin and analogues thereof.

Moreover, combinations with drugs for influencing high blood pressure, chronic heart failure or atherosclerosis, such as e.g.: Angiotensin II receptor antagonists (e.g. telmisartan, candesartan, valsartan, losartan, eprosartan, irbesartan, olmesartan, tasosartan, azilsartan), ACE inhibitors, ECE inhibitors, diuretics, beta-blockers, calcium antagonists, centrally acting hypertensives, antagonists of the alpha-2-adrenergic receptor, inhibitors of neutral endopeptidase, thrombocyte aggregation inhibitors and others or combinations thereof are suitable.

In another aspect, this invention relates to the use of a compound according to the invention or a physiologically acceptable salt thereof combined with at least one of the active substances described above as a combination partner, for preparing a medicament which is suitable for the treatment or prevention of diseases or conditions which can be affected by binding to the receptors for GLP-1 and glucagon and by modulating their activity. This is preferably a disease in the context of the metabolic syndrome, particularly one of the diseases or conditions listed above, most particularly diabetes or obesity or complications thereof.

The use of the compounds according to the invention, or a physiologically acceptable salt thereof, in combination with one or more active substances may take place simultaneously, separately or sequentially.

The use of the compound according to the invention, or a physiologically acceptable salt thereof, in combination with another active substance may take place simultaneously or at staggered times, but particularly within a short space of time. If they are administered simultaneously, the two active substances are given to the patient together; if they are used at staggered times, the two active substances are given to the patient within a period of less than or equal to 12 hours, but particularly less than or equal to 6 hours.

Consequently, in another aspect, this invention relates to a medicament which comprises a compound according to the invention or a physiologically acceptable salt of such a compound and at least one of the active substances described above as combination partners, optionally together with one or more inert carriers and/or diluents.

The compound according to the invention, or physiologically acceptable salt or solvate thereof, and the additional active substance to be combined therewith may both be present together in one formulation, for example a tablet or capsule, or separately in two identical or different formulations, for example as so-called kit-of-parts.

LEGENDS TO THE FIGURES

Figure 8:
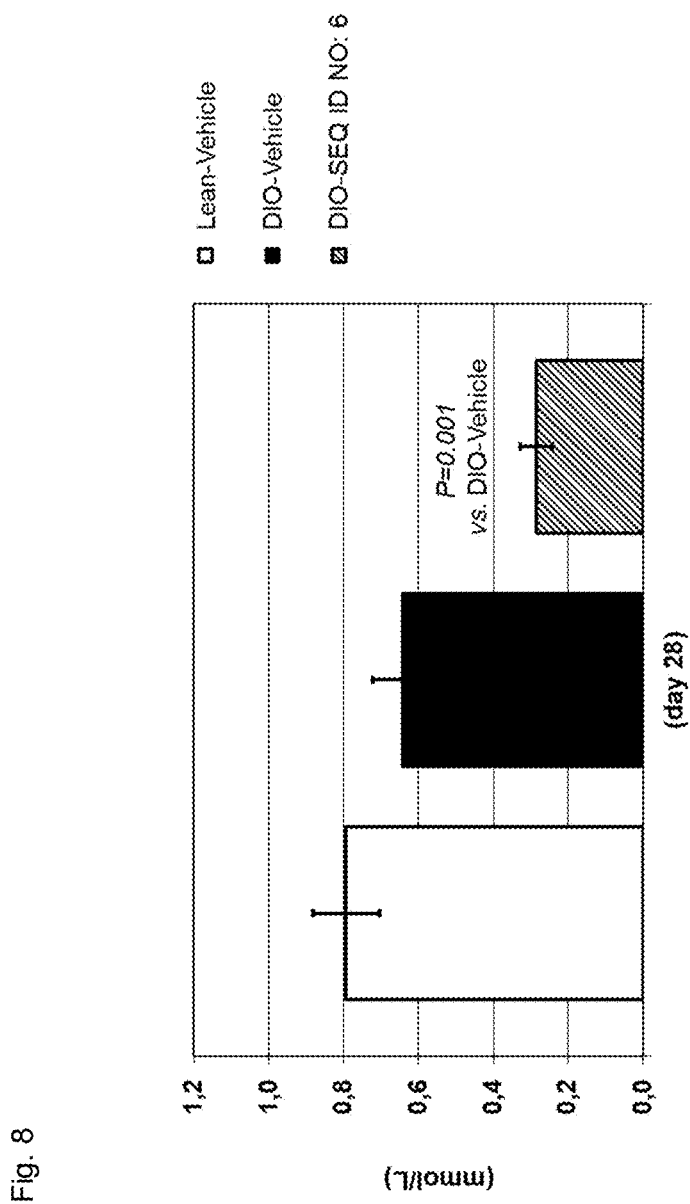
Figure 9:
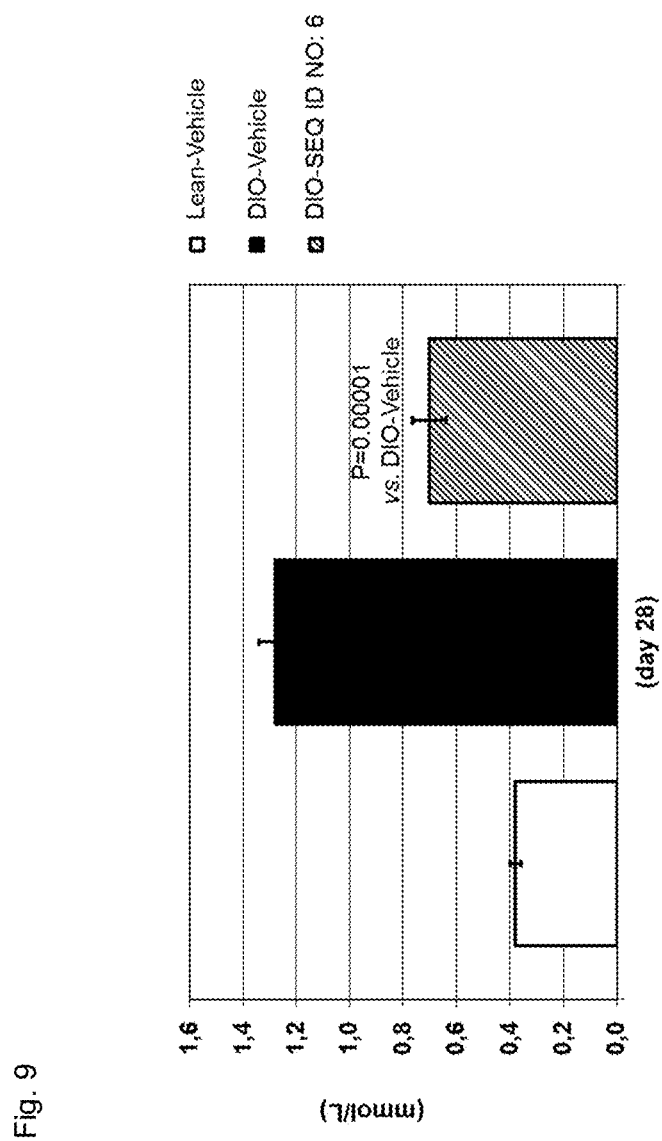
Figure 16:
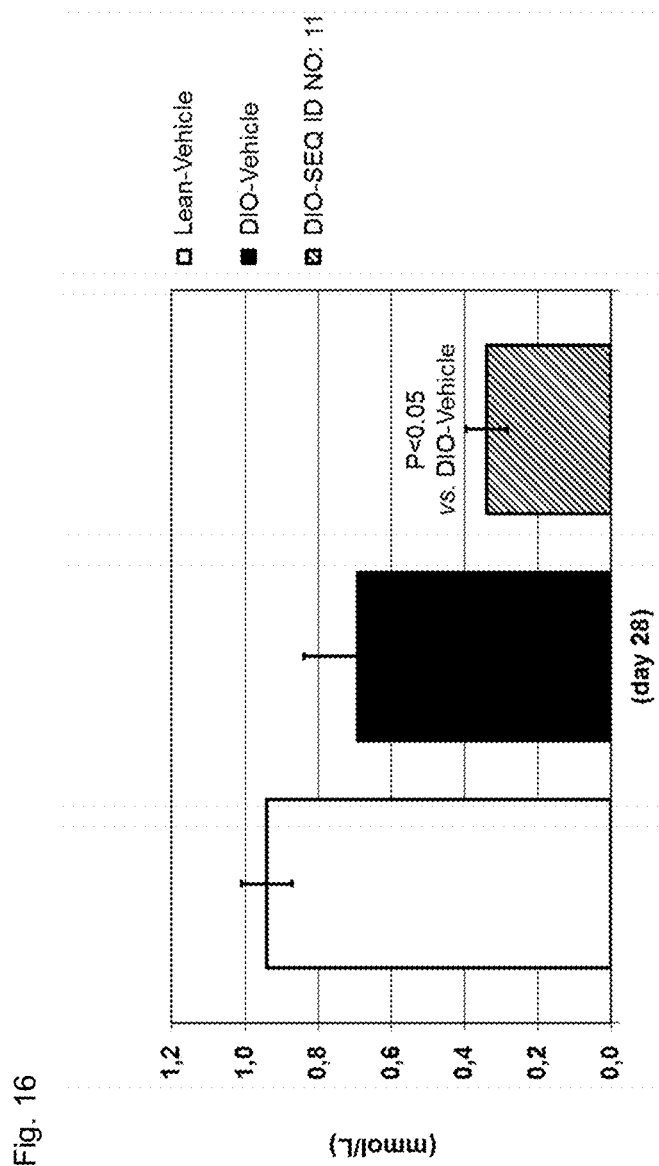
Figure 17:
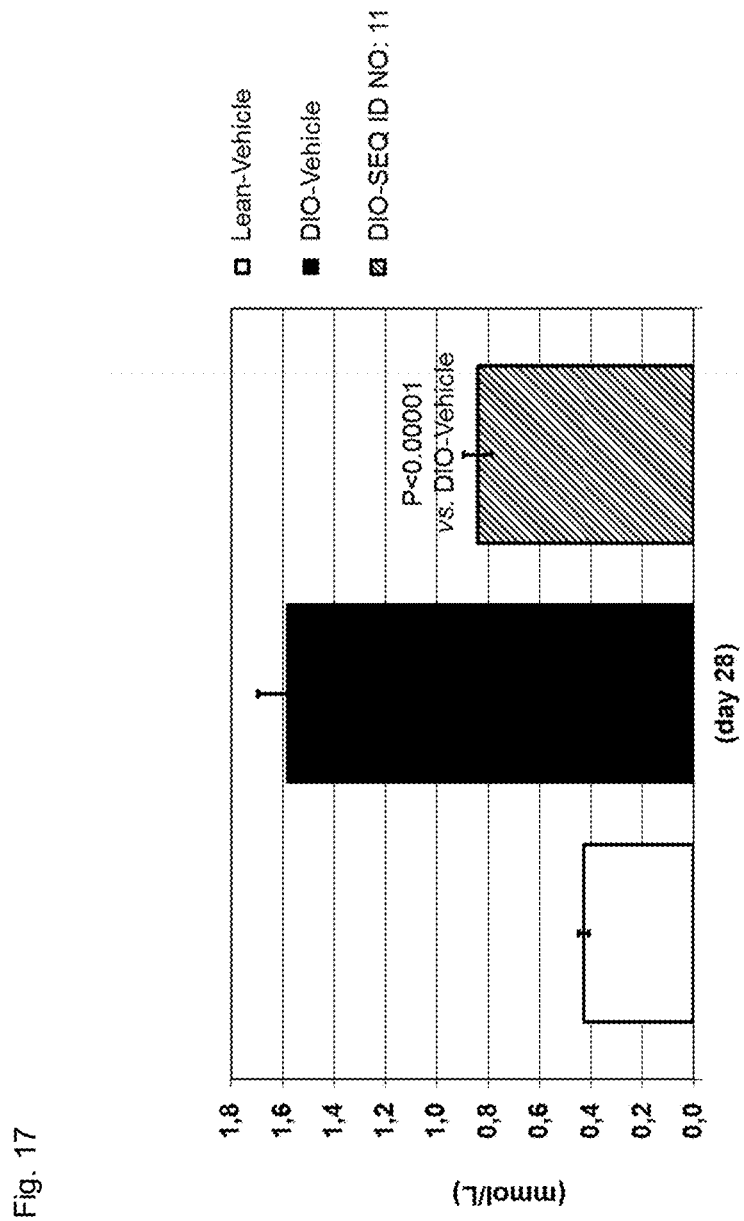
Figure 18:
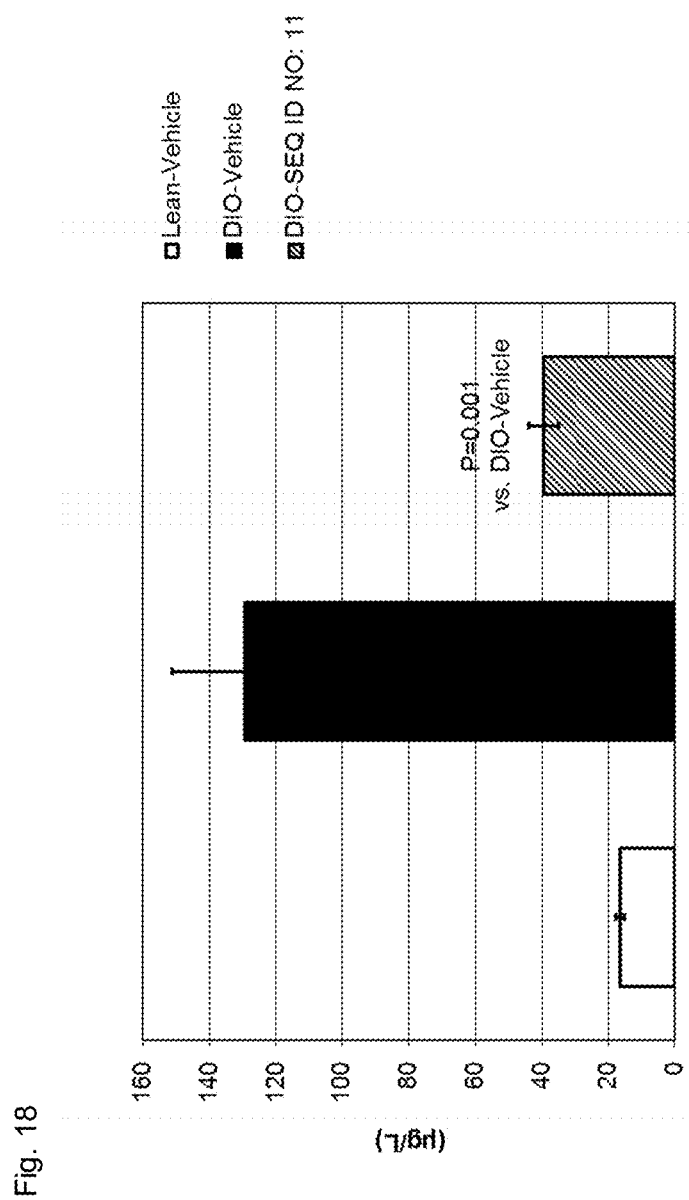
Figure 25:
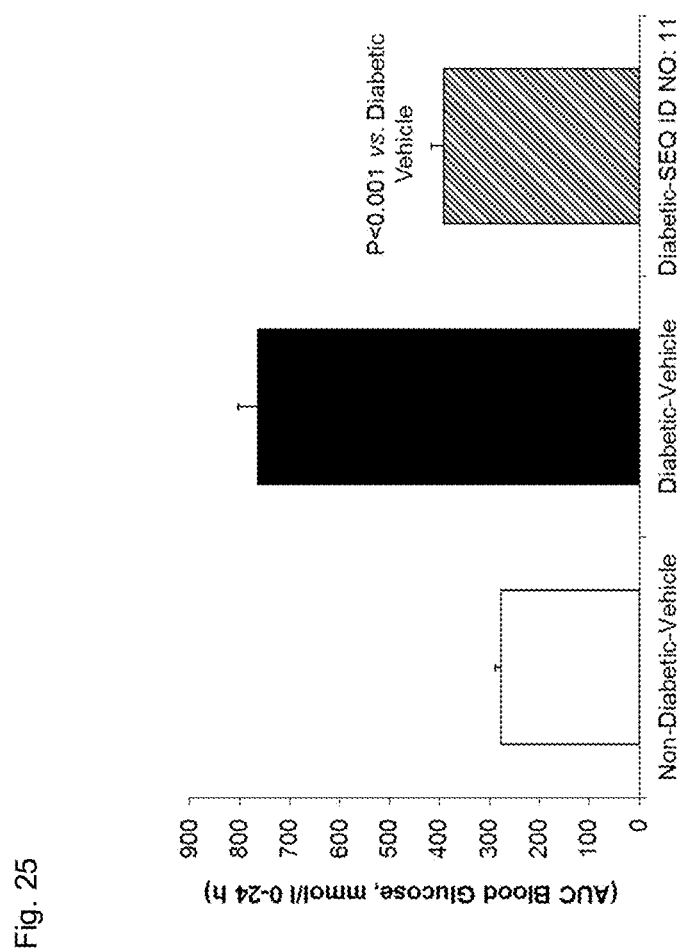
Figure 26:
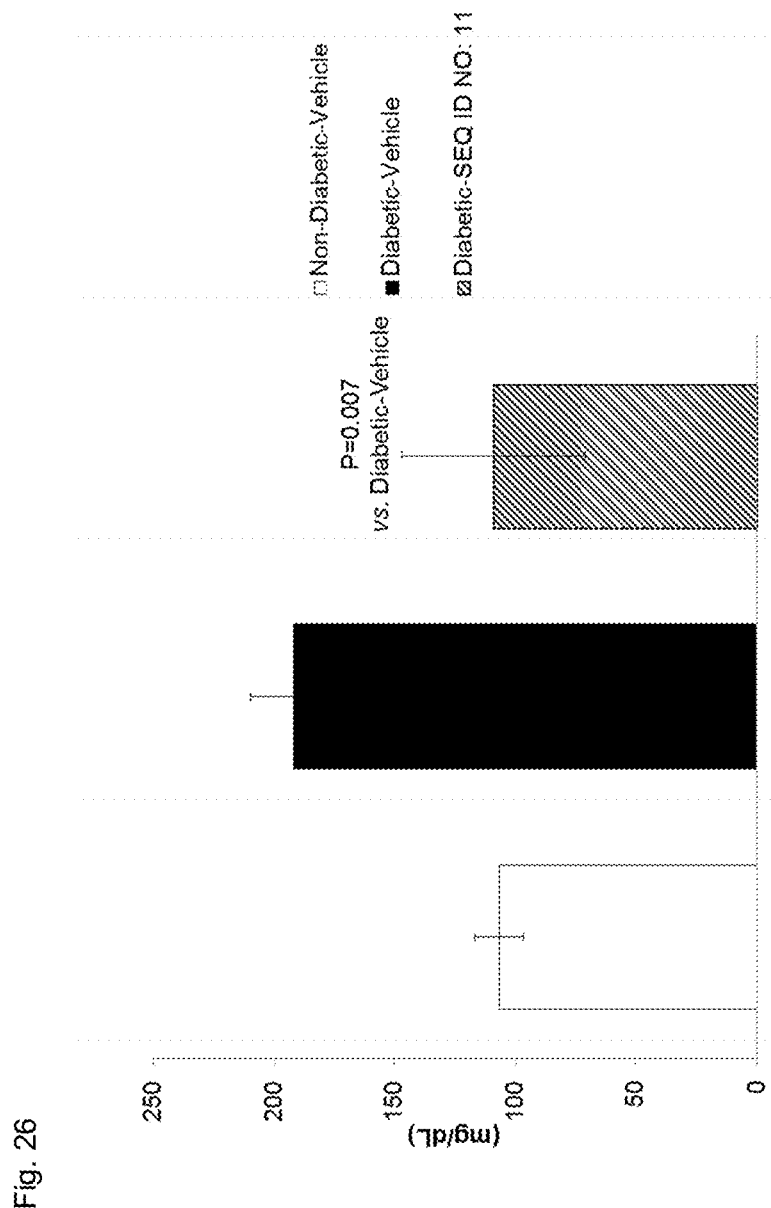

FIG. 1: Comparison of Dynamic Debye plots for peptide formulations exhibiting reversible self-association (attractive interactions) and repulsive virial interactions FIG. 2. SEQ ID NO: 6, Blood glucose profile following first treatment in fed DIO mice FIG. 3. SEQ ID NO: 6, Body mass in DIO mice FIG. 4. SEQ ID NO: 6, Body mass change in DIO mice FIG. 5. SEQ ID NO: 6, Whole body fat mass change in DIO mice FIG. 6. SEQ ID NO: 6, Feed consumption estimate in DIO mice FIG. 7. SEQ ID NO: 6, Terminal liver mass in DIO mice FIG. 8. SEQ ID NO: 6, Terminal plasma triglycerides in fed DIO mice FIG. 9. SEQ ID NO: 6, Plasma LDL in fed DIO mice FIG. 10. SEQ ID NO: 11, Blood glucose profile following first treatment in fed DIO mice FIG. 11. SEQ ID NO: 11, Body mass in DIO mice FIG. 12. SEQ ID NO: 11, Whole body mass change in DIO mice FIG. 13. SEQ ID NO: 11, Whole body fat mass change in DIO mice FIG. 14. SEQ ID NO: 11, Feed consumption estimate in DIO mice FIG. 15. SEQ ID NO: 11, Terminal liver mass in DIO mice FIG. 16. SEQ ID NO: 11, Terminal plasma triglycerides in fed DIO mice FIG. 17. SEQ ID NO: 11, Plasma LDL in fed DIO mice FIG. 18. SEQ ID NO: 11, Terminal plasma insulin in fed DIO mice FIG. 19. SEQ ID NO: 11, Terminal plasma glucose in fed DIO mice FIG. 20. SEQ ID NO: 6, SEQ ID NO: 8, SEQ ID NO: 9, Blood glucose profile in fed db/db mice FIG. 21. SEQ ID NO: 6, SEQ ID NO: 8, SEQ ID NO: 9, Blood Glucose Area Under the Curve in fed db/db mice FIG. 22. SEQ ID NO: 7, Blood glucose profile in fed db/db mice FIG. 23. SEQ ID NO: 7, Blood glucose Area Under the Curve in fed db/db mice FIG. 24. SEQ ID NO: 11, Blood glucose profile in fed db/db mice FIG. 25. SEQ ID NO: 11, Blood Glucose Area Under the Curve in fed db/db mice FIG. 26. SEQ ID NO: 11, Terminal serum triacylglycerol concentration in fed db/db mice FIG. 27. SEQ ID NO: 10, SEQ ID NO: 12, SEQ ID NO: 13, SEQ ID NO: 16, SEQ ID NO: 26, Blood glucose profile in fed db/db mice FIG. 28. SEQ ID NO: 10, SEQ ID NO: 12, SEQ ID NO: 13, SEQ ID NO: 16, SEQ ID NO: 26. Blood Glucose Area Under the Curve in fed db/db mice FIG. 29. Food intake and body weight monitoring data (SEQ ID NO: 11, SEQ ID NO: 6, Liraglutide)

Figure 30:
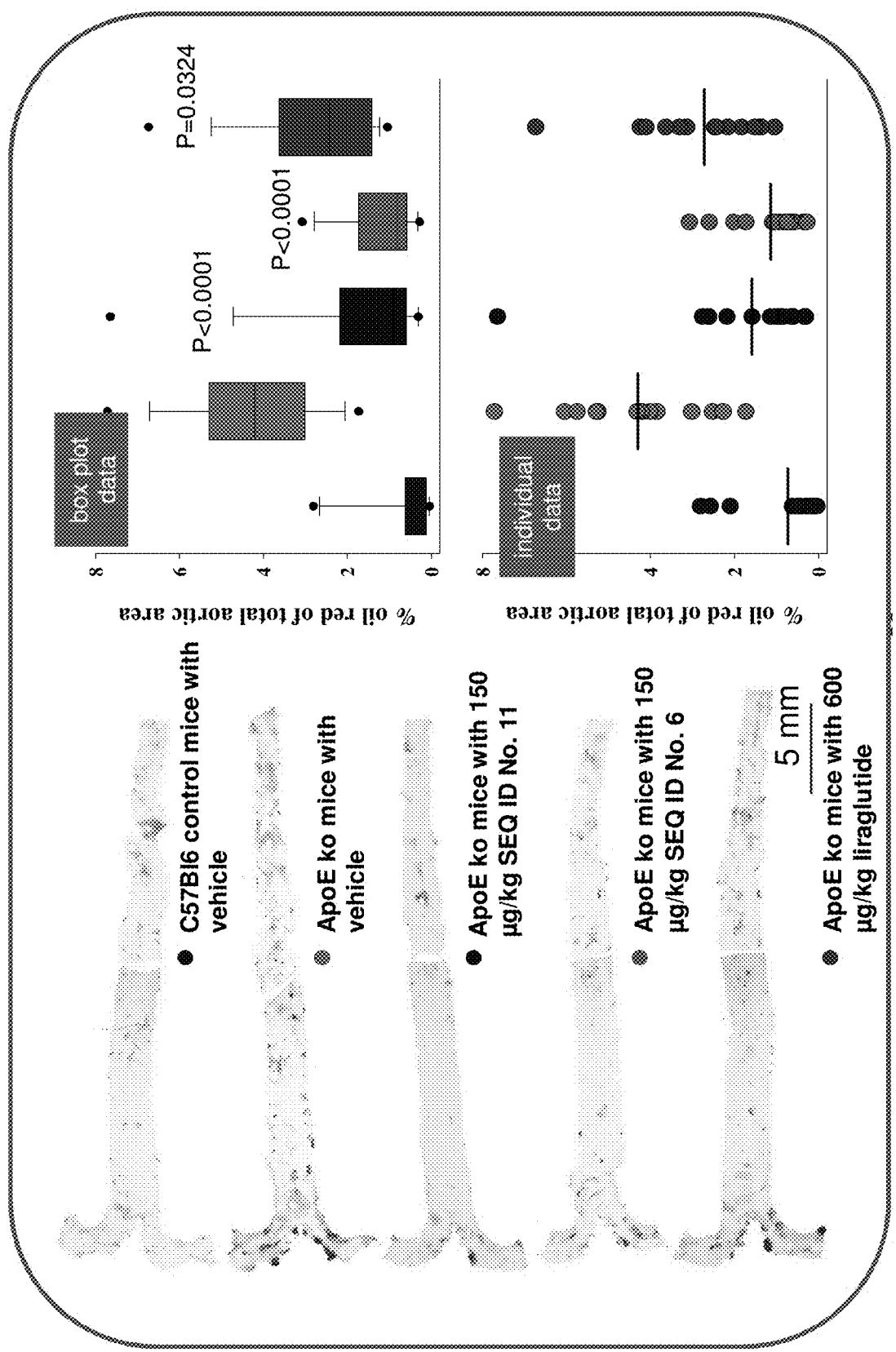

FIG. 30. Aortic plaque area data (SEQ ID NO: 11, SEQ ID NO: 6, Liraglutide)

Figure 31:
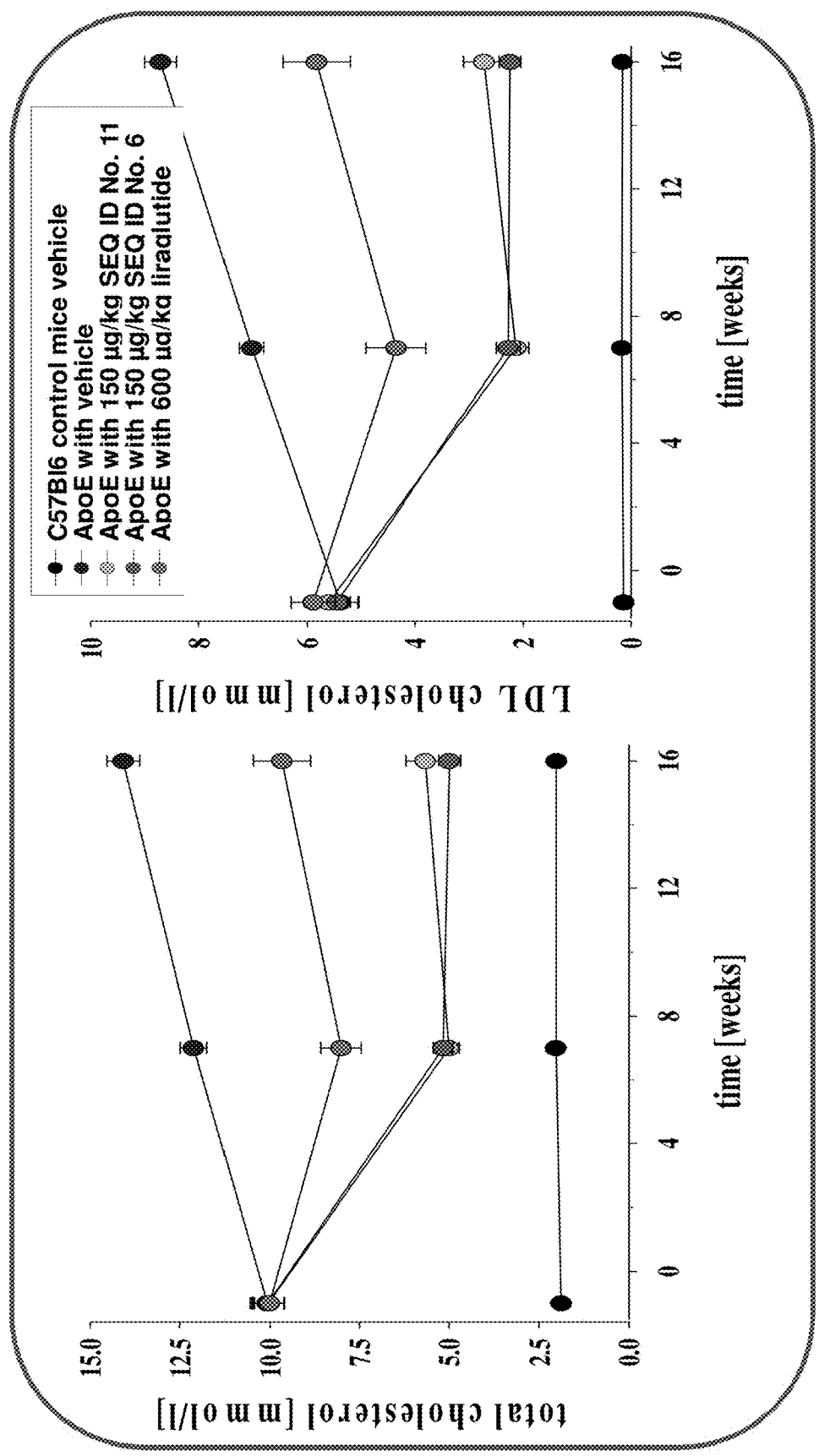

FIG. 31. Serum total cholesterol and LDL-cholesterol data (SEQ ID NO: 11, SEQ ID NO: 6, Liraglutide)

METHODS

Abbreviations employed are as follows:
AA amino acid
AEEAc (2-(2-aminoethoxy)ethoxy)acetyl
Aib alpha-amino-isobutyric acid
cAMP cyclic adenosine monophosphate
Boc tert-butyloxycarbonyl
BOP (benzotriazol-1-yloxy)tris(dimethylamino)phosphonium hexafluorophosphate
BSA bovine serum albumin
tBu tertiary butyl
dAla D-alanine
DCM dichloromethane
Dde 1-(4,4-dimethyl-2,6-dioxocyclohexylidene)-ethyl
ivDde 1-(4,4-dimethyl-2,6-dioxocyclohexylidene)-3-methyl-butyl
DIC N,N'-diisopropylcarbodiimide
DIPEA N,N-diisopropylethylamine
DMEM Dulbecco's modified Eagle's medium
DMF dimethyl formamide
DMS dimethylsulfide
EDT ethanedithiol
FA formic acid
FBS fetal bovine serum
Fmoc fluorenylmethyloxycarbonyl
gAAA gamma-amino adipic acid
gGlu gamma-glutamate (yE)
HATU O-(7-azabenzotriazol-1-yl)-N, N, N, N'-tetramethyluronium hexafluorophosphate
HBSS Hanks' Balanced Salt Solution
HBTU 2-(1H-benzotriazol-1-yl)-1,1,3,3-tetramethyl-uronium hexafluorophosphate
HEPES 2-[4-(2-hydroxyethyl)piperazin-1-yl]ethanesulfonic acid
HOBt 1-hydroxybenzotriazole
HOSu N-hydroxysuccinimide
HPLC High Performance Liquid Chromatography
HTRF Homogenous Time Resolved Fluorescence
IBMX 3-isobutyl-1-methylxanthine
LC/MS Liquid Chromatography/Mass Spectrometry
Mmt monomethoxy-trityl
Palm palmitoyl
PBS phosphate buffered saline
PEG polyethylene glycole
PK pharmacokinetic
RP-HPLC reversed-phase high performance liquid chromatography
Stea stearyl
TFA trifluoroacetic acid
Trt trityl
UV ultraviolet
General Synthesis of Peptidic Compounds
Materials Different Rink-Amide resins (4-(2',4'-Dimethoxyphenyl-Fmoc-aminomethyl)-phenoxyacetamido-norleucylaminomethyl resin, Merck Biosciences; 4-[(2,4-Dimethoxyphenyl) (Fmoc-amino)methyl]phenoxy acetamido methyl resin, Agilent Technologies) were used for the synthesis of peptide amides with loadings in the range of 0.2-0.7 mmol/g.

Fmoc protected natural amino acids were purchased from Protein Technologies Inc., Senn Chemicals, Merck Biosciences, Novabiochem, Iris Biotech, Bachem, Chem-Impex International or MATRIX Innovation. The following standard amino acids were used throughout the syntheses: Fmoc-L-Ala-OH, Fmoc-Arg(Pbf)-OH, Fmoc-L-Asn(Trt)-OH, Fmoc-L-Asp(OtBu)-OH, Fmoc-L-Cys(Trt)-OH, Fmoc-L-Gln(Trt)-OH, Fmoc-L-Glu(OtBu)-OH, Fmoc-Gly-OH, Fmoc-L-His(Trt)-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Pro-OH, Fmoc-L-Ser(tBu)-OH, Fmoc-L-Thr(tBu)-OH, Fmoc-L-Trp(Boc)-OH, Fmoc-L-Tyr(tBu)-OH, Fmoc-L-Val-OH.

In addition, the following special amino acids were purchased from the same suppliers as above: Fmoc-L-Lys (ivDde)-OH, Fmoc-L-Lys(Mmt)-OH, Fmoc-Aib-OH, Fmoc-D-Ser(tBu)-OH, Fmoc-D-Ala-OH, Boc-L-His(Boc)-OH (available as toluene solvate) and Boc-L-His(Trt)-OH.

Furthermore, the building blocks (2S)-6-[[(4S)-5-tert-butoxy-4-[[(4S)-5-tert-butoxy-4-(hexadecanoylamino)-5-oxopentanoyl]amino]-5-oxo-pentanoyl]amino]-2-(9H-fluoren-9-ylmethoxycarbonylamino)hexanoic acid and Boc-L-His (Trt)-Aib-OH can be applied. Both building blocks were synthesized separately.

The solid phase peptide syntheses were performed for example on a Prelude Peptide Synthesizer (Protein Technologies Inc) or similar automated synthesizer using standard Fmoc chemistry and HBTU/DIPEA activation. DMF was used as the solvent. Deprotection: 20% piperidine/DMF for 2×2.5 min. Washes: 7×DMF. Coupling 2:5:10 200 mM AA/500 mM HBTU/2M DIPEA in DMF 2× for 20 min. Washes: 5×DMF.

In cases where a Lys-side-chain was modified, Fmoc-L-Lys(ivDde)-OH or Fmoc-L-Lys(Mmt)-OH was used in the corresponding position. After completion of the synthesis, the ivDde group was removed according to a modified literature procedure (S. R. Chhabra et al., Tetrahedron Lett., 1998, 39, 1603), using 4% hydrazine hydrate in DMF. The Mmt group was removed by repeated treatment with AcOH/TFE/DCM (1/2/7) for 15 minutes at RT, the resin then repeatedly washed with DCM, 5% DIPEA in DCM and 5% DIPEA in DCM/DMF.

The following acylations were carried out by treating the resin with the N-hydroxy succinimide esters of the desired acid or using coupling reagents like HBTU/DIPEA or HOBt/DIC.

All the peptides that have been synthesized were cleaved from the resin with King's cleavage cocktail consisting of 82.5% TFA, 5% phenol, 5% water, 5% thioanisole, 2.5% EDT. The crude peptides were then precipitated in diethyl or diisopropyl ether, centrifuged, and lyophilized. Peptides were analyzed by analytical HPLC and checked by ESI mass spectrometry. Crude peptides were purified by a conventional preparative RP-HPLC purification procedure.

Alternatively, peptides were synthesized by a manual synthesis procedure: 0.3 g Desiccated Rink amide MBHA Resin (0.66 mmol/g) was placed in a polyethylene vessel equipped with a polypropylene filter. Resin was swollen in DCM (15 ml) for 1 h and DMF (15 ml) for 1 h. The Fmoc group on the resin was de-protected by treating it twice with 20% (v/v) piperidine/DMF solution for 5 and 15 min. The resin was washed with DMF/DCM/DMF (6:6:6 time each). A Kaiser test (quantitative method) was used for the conformation of removal of Fmoc from solid support. The C-terminal Fmoc-amino acid (5 equiv. excess corresponding to resin loading) in dry DMF was added to the de-protected resin and coupling of the next Fmoc-amino acid was initiated with 5 equivalent excess of DIC and HOBT in DMF. The concentration of each reactant in the reaction mixture was approximately 0.4 M. The mixture was rotated on a rotor at room temperature for 2 h. Resin was filtered and washed with DMF/DCM/DMF (6:6:6 time each). Kaiser test on peptide resin aliquot upon completion of coupling was negative (no colour on the resin). After the first amino acid attachment, the unreacted amino group, if any, in the resin was capped used acetic anhydride/pyridine/DCM (1:8:8) for 20 minutes to avoid any deletion of the sequence. After capping, resin was washed with DCM/DMF/DCM/DMF (6/6/6/6 time each). The Fmoc group on the C-terminal amino acid attached peptidyl resin was deprotected by treating it twice with 20% (v/v) piperidine/DMF solution for 5 and 15 min. The resin was washed with DMF/DCM/DMF (6:6:6 time each). The Kaiser test on peptide resin aliquot upon completion of Fmoc-deprotection was positive.

The remaining amino acids in target sequence on Rink amide MBHA Resin were sequentially coupled using Fmoc AA/DIC/HOBt method using 5 equivalent excess corresponding to resin loading in DMF. The concentration of each reactant in the reaction mixture was approximately 0.4 M. The mixture was rotated on a rotor at room temperature for 2 h. Resin was filtered and washed with DMF/DCM/DMF (6:6:6 time each). After each coupling step and Fmoc deprotection step, a Kaiser test was carried out to confirm the completeness of the reaction.

After the completion of the linear sequence, the ε-amino group of lysine used as branching point or modification point was deprotected by using 2.5% hydrazine hydrate in DMF for 15 min×2 and washed with DMF/DCM/DMF (6:6:6 time each). The γ-carboxyl end of glutamic acid was attached to the ε-amino group of Lys using Fmoc-Glu(OH)-OtBu with DIC/HOBt method (5 equivalent excess with respect to resin loading) in DMF. The mixture was rotated on a rotor at room temperature for 2 h. The resin was filtered and washed with DMF/DCM/DMF (6×30 ml each). The Fmoc group on the glutamic acid was de-protected by treating it twice with 20% (v/v) piperidine/DMF solution for 5 and 15 min (25 ml each). The resin was washed with DMF/DCM/DMF (6:6:6 time each). A Kaiser test on peptide resin aliquot upon completion of Fmoc-deprotection was positive.

If the side-chain branching also contains one more γ-glutamic acid, a second Fmoc-Glu(OH)-OtBu used for the attachment to the free amino group of γ-glutamic acid with DIC/HOBt method (5 equivalent excess with respect to resin loading) in DMF. The mixture was rotated on a rotor at room temperature for 2 h. Resin was filtered and washed with DMF/DCM/DMF (6×30 ml each). The Fmoc group on the γ-glutamic acid was de-protected by treating it twice with 20% (v/v) piperidine/DMF solution for 5 and 15 min (25 mL). The resin was washed with DMF/DCM/DMF (6:6:6 time each). A Kaiser test on peptide resin aliquot upon completion of Fmoc-deprotection was positive.

Palmitic acid and stearic acid attachment to side chains of glutamic acid:

To the free amino group of γ-glutamic acid, palmitic acid or stearic acid (5 equiv.) dissolved in DMF was added and coupling was initiated by the addition of DIC (5 equiv.) and HOBt (5 equiv.) in DMF. The resin was washed with DMF/DCM/DMF (6:6:6 time each).

Final cleavage of peptide from the resin:

The peptidyl resin synthesized by manual synthesis was washed with DCM (6×10 ml), MeOH (6×10 ml) and ether (6×10 ml) and dried in vacuum desiccators overnight.

The cleavage of the peptide from the solid support was achieved by treating the peptide-resin with reagent cocktail (80.0% TFA/5% thioanisole/5% phenol/2.5% EDT, 2.5% DMS and 5% DCM) at room temperature for 3 h. Cleavage mixture was collected by filtration and the resin was washed with TFA (2 ml) and DCM (2×5 ml). The excess TFA and DCM was concentrated to small volume under nitrogen and a small amount of DCM (5-10 ml) was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged and the supernatant ether was removed and fresh ether was added to the peptide and re-centrifuged. The crude sample was preparative HPLC purified and lyophilized. The identity of peptide was confirmed by LCMS.

In addition, a different route for the introduction of the lysine side chain is used, applying a prefunctionalized building block where the side chain is already attached to the lysine (e.g. (2S)-6-[[(4S)-5-tert-butoxy-4-[[(4S)-5-tert-butoxy-4-(hexadecanoylamino)-5-oxo-pentanoyl]amino]-5-oxo-pentanoyl]amino]-2-(9H-fluoren-9-ylmethoxycarbonylamino)hexanoic acid) as coupling partner in the peptide synthesis. 0.67 mmol of peptide resin bearing an amino-group is washed with 20 ml of dimethylformamide. 2.93 g of (2S)-6-[[(4S)-5-tert-butoxy-4-[[(4S)-5-tert-butoxy-4-(hexadecanoylamino)-5-oxo-pentanoyl]amino]-5-oxo-pentanoyl]amino]-2-(9H-fluoren-9-ylmethoxycarbonylamino) hexanoic acid is dissolved in 20 ml of dimethylformamide together with 310 mg of hydroxybenzotriazol hydrate and 0.32 ml of diisopropylcarbodiimide. After stirring of 5 minutes the solution is added to the resin. The resin is agitated for 20 h and then washed 3 times with 20 ml of dimethylformamide each. A small resin sample is taken and subjected to the Kaiser-test and the Chloranil-test (E. Kaiser, R. L. Colescott, C. D. Bossinger, P. I. Cook, Anal. Biochem. 1970, 34, 595-598; Chloranil-Test: T. Vojkovsky, Peptide Research 1995, 8, 236-237). This procedure avoids the need of a selective deprotection step as well as the selective attachment of the side chain building blocks on a very advanced synthesis intermediate.

Analytical HPLC/UPLC

Method A: Detection at 210-225 nm
column: Waters ACQUITY UPLC® CSH™ C18 1.7 µm (150×2.1 mm) at 50° C.
solvent: $H_2O+0.05\%$ TFA: ACN+0.035% TFA (flow 0.5 ml/min)
gradient: 80:20 (0 min) to 80:20 (3 min) to 25:75 (23 min) to 2:98 (23.5 min) to 2:98 (30.5 min) to 80:20 (31 min) to 80:20 (37 min)
optionally with mass analyzer: LCT Premier, electrospray positive ion mode Method B: Detection at 214
column: Waters ACQUITY UPLC® CSH™ C18 1.7 µm (150×2.1 mm) at 50° C.
solvent: $H_2O+0.05\%$ TFA: ACN+0.035% TFA (flow 0.5 ml/min)
gradient: 80:20 (0 min) to 80:20 (3 min) to 25:75 (23 min) to 2:98 (23.5 min) to 2:98 (30.5 min) to 80:20 (31 min) to 80:20 (37 min)
optionally with mass analyzer: Agilent 6230 Accurate-Mass TOF, Dual Agilent Jet Stream ESI Method C: Detection at 214 nm
column: Waters ACQUITY UPLC® CSH™ C18 1.7 µm (150×2.1 mm) at 50° C.
solvent: $H_2O+0.1\%$ TFA: ACN+0.1% TFA (flow 0.5 ml/min)
gradient: 80:20 (0 min) to 80:20 (3 min) to 25:75 (23 min) to 2:98 (23.5 min) to 2:98 (30.5 min) to 80:20 (31 min) to 80:20 (38 min)
optionally with mass analyzer: Agilent 6230 Accurate-Mass TOF, Agilent Jet Stream ESI Method D: Detection at 220 nm
column: Waters ACQUITY BEH C18 (2.1×100 mm×1.7 µm), Temp: 40° C. Aries peptide XB C18 (4.6×250 mm×3.6 µm), Temp: 40° C.
solvent: $H_2O+0.1\%$ formic acid (buffer A): ACN+0.1% b formic acid (flow 1 ml/min) (buffer B)
gradient: Equilibration of the column with 2% buffer B and elution by a gradient of 2% to 70% buffer B during 15 min??

Method E: Detection at 215 nm
column: Waters ACQUITY UPLC® CSH™ C18 1.7 µm (150×2.1 mm) at 50° C.
solvent: $H_2O+0.05\%$ TFA: ACN+0.035% TFA (flow 0.5 ml/min)
gradient: 80:20 (0 min) to 80:20 (3 min) to 25:75 (23 min) to 5:95 (23.5 min) to 5:95 (25.5 min) to 80:20 (26 min) to 80:20 (30 min)

General Preparative HPLC Purification Procedure

The crude peptides were purified either on an Akta Purifier System, a Jasco semiprep HPLC System or a Agilent 1100 HPLC system. Preparative RP-C18-HPLC columns of different sizes and with different flow rates were used depending on the amount of crude peptide to be purified. Acetonitrile+0.1% TFA (B) and water +0.1% TFA (A) were employed as eluents. Product-containing fractions were collected and lyophilized to obtain the purified product, typically as TFA salt.

Solubility Assessment of Exendin-4 Derivatives

Prior to the solubility measurement of a peptide batch, its purity was determined through UPLC/MS.

For solubility testing the target concentration was 10 mg pure compound/ml. Therefore solutions from solid samples were prepared in a buffer system with a concentration of 10 mg/mL compound based on the previously determined % purity:

Solubility buffer system A) Acetate Buffer pH 4.5, 100 mM sodium acetate trihydrate, 2.7 mg/ml m-Cresol Solubility buffer system B) Phosphate Buffer pH 7.4, 100 mM sodium hydrogen phosphate, 2.7 mg/ml m-Cresol Solubility buffer system C) Citrate Buffer pH 6.0, citric acid 100 mM, 2.7 mg/mL m-cresol UPLC-UV was performed after 1 hour of gentle agitation from the supernatant, which was obtained after 15 min of centrifugation at 2500 RCF (relative centrifugal acceleration).

The solubility was determined by the comparison of the UV peak area of 2 µL-injection of a buffered sample diluted 1:10 with a standard curve of a reference peptide with known concentration. The different UV extinction coefficients of sample and reference peptide were calculated based on the different amino acid sequences and considered in the concentration calculation.

Chemical Stability Assessment of Exendin-4 Derivatives

Prior to the chemical stability measurement of a peptide batch, its purity was determined through UPLC/MS. For stability testing the target concentration was 1 mg pure compound/ml. Therefore solutions from solid samples were prepared in a buffer system with a concentration of 1 mg/mL compound based on the previously determined % purity:

Chemical stability buffer system A) 25 mM acetate buffer pH 4.5, 3 mg/mL L-Methionine, 2.7 mg/mL m-cresol, 18 mg/mL Glycerol 85% Chemical stability buffer system B) 25 mM phosphate buffer pH 6.0, 3 mg/mL L-Methionine, 2.7 mg/mL m-cresol, 18 mg/mL Glycerol 85%

Peptide solutions were filtered through 0.22 µM pore size and filled into aliquots under aseptic conditions. At starting point, UPLC-UV was performed by injection of 2 µl of the undiluted sample.

For chemical stability testing, aliquots were stored for 28 days at 5 and 40° C. After this time course the samples were centrifuged for 15 min at 2500 RCF. Then 2 µl of the undiluted supernatant were analysed with UPLC-UV.

The chemical stability was rated through the relative loss of purity calculated by the equation:

$$[(\text{purity at starting point}) - (\text{purity after 28 days at X}° \text{C.})]/(\text{purity at starting point})*100\%$$

X=5 or 40° C.
The purity is calculated as
[(peak area peptide)/(total peak area)]*100%

Dynamic Light Scattering (DLS) for the Assessment of Physical Stability

A monochromatic and coherent light beam (laser) is used to illuminate the liquid sample. Dynamic Light Scattering (DLS) measures light scattered from particles (1 nm≤radius≤1 µm) that undergo Brownian motion. This motion is induced by collisions between the particles and solvent molecules that themselves are moving due to their thermal energy. The diffusional motion of the particles results in temporal fluctuations of the scattered light [Pecora, R. Dynamic Light Scattering: Applications of Photon Correlation Spectroscopy, Plenum Press, 1985].

The scattered light intensity fluctuations are recorded and transformed into an autocorrelation function. By fitting the autocorrelation curve to an exponential function, the diffusion coefficient D of the particles in solution can be derived. The diffusion coefficient is then used to calculate the hydrodynamic radius $R_h$ (or apparent Stokes radius) through the Stokes-Einstein equation assuming spherical particles. This calculation is defined in ISO 13321 and ISO 22412 [International Standard ISO13321 Methods for Determination of Particle Size Distribution Part 8: Photon Correlation Spectroscopy, International Organisation for Standardisation (ISO) 1996; International Standard ISO22412 Particle Size Analysis—Dynamic Light Scattering, International Organisation for Standardisation (ISO) 2008].

In case of polydisperse samples, the autocorrelation function is the sum of the exponential decays corresponding to each of the species. The temporal fluctuations of the scattered light can then be used to determine the size distribution profile of the particle fraction or family. The first order result is an intensity distribution of scattered light as a function of the particle size. The intensity distribution is naturally weighted according to the scattering intensity of each particle fraction or family. For biological materials or polymers the particle scattering intensity is proportional to the square of the molecular weight. Thus, small amount of aggregates/agglomerates or presence or a larger particle species can dominate the intensity distribution. However this distribution can be used as a sensitive detector for the presence of large material in the sample. The intensity distribution can be converted into a volume or mass distribution of the particle sizes using the Mie theory under certain assumptions. In contrast to the intensity distribution, the mass distribution is best used for comparative purposes and should never be considered absolute (due to the underlying assumptions).

The DLS technique produces distributions with inherent peak broadening. The polydispersity index % Pd is a measure of the width of the particle size distribution and is calculated by standard methods described in ISO13321 and ISO22412 [International Standard ISO13321 Methods for Determination of Particle Size Distribution Part 8: Photon Correlation Spectroscopy, International Organisation for Standardisation (ISO) 1996; International Standard ISO22412 Particle Size Analysis—Dynamic Light Scattering, International Organisation for Standardisation (ISO) 2008].

DLS Interaction Parameter ($k_D$)

The DLS interaction parameter ($k_D$) is a measure to describe inter-particle interactions, where the particles are folded proteins or peptides [Sandeep Yadav et al. (2009) J Pharm Sc, Vol 99(3), pp 1152-1168; Brian D. Connolly et al. (2012) Biophysical Journal Volume 103, pp 69-78].

The parameter $k_D$ is derived from the concentration dependence of the diffusion coefficient D, which is given by an expansion in powers of the concentration c:

$$D(c)=D_0(1+k_Dc+k_{iD}c^2+k_{jD}c^3+\ldots)$$

Neglecting the higher order terms, i.e. $k_{iD}=k_{jD}=\ldots=0$, the data can be fitted linearly and $k_D$ is obtained from the slope of the curve $D=D_0(1+k_Dc)$ and $D_0$. $D_0$ is the diffusion coefficient at zero concentration. The parameter $k_D$ can be used to describe interaction of protein or peptide molecules or oligomers with their-self and their environment in solution and is theoretically related to the virial coefficient $B_{22}$ as for example described by Harding and Johnson, where M is the molar mass, $k_s$ the first order concentration coefficient of sedimentation velocity and u the partial specific volume [Harding S E, Johnson P. (1985) Biochem J, 231, pp 543-547].

$$k_D=2B_{22}M-k_s-u$$

Positive $B_{22}$ values indicate samples that favor salvation over self-association, while negative $B_{22}$ values indicate samples that prefer self-association. From a pragmatic point of view, $k_D$ is analogous in its meaning to $B_{22}$ and gives information on the net-forces between the molecules. High values indicate strong net-repulsive interactions, while low values indicate net-attractive forces. Therefore, $k_D$ can be used for relative, qualitative comparison (see FIG. 1).

For every peptide solution, the hydrodynamic radius $R_h$ and the diffusion constant D (related via the Stokes-Einstein equation) were determined as an average over triplicates. Both parameters were determined at different peptide concentrations (e.g., $R_{h1}$ and $D_1$: 1 mg/ml and $R_{h5}$ and $D_5$: 5 mg/ml) in the same buffer system. The difference of these parameters between low and high peptide concentration is a surrogate for the DLS interaction parameter $k_D$. $R_{h5}<R_{h1}$ or $D_5>D_1$ correspond to $k_D>0$ and therefore to repulsive inter-particle interactions that result in improved physical (or colloidal) stability.

DLS buffer system A) 25 mM acetate buffer pH 4.5, 3 mg/mL L-Methionine, 2.7 mg/mL m-cresol, 18 mg/mL Glycerol 85%

DLS buffer system B) 25 mM phosphate buffer pH 6.0, 3 mg/mL L-Methionine, 2.7 mg/mL m-cresol, 18 mg/mL Glycerol 85%

DLS Method A: DLS measurements were performed on a W130i apparatus (Avid Nano Ltd, High Wycombe, UK) and using a low-volume disposable cuvette (UVette, Eppendorf AG, Hamburg, Germany). The data were processed with i-Size 3.0 provided by Avid Nano. Parameters of the particle size distribution were determined with non-negatively constrained least squares (NNLS) methods using DynaLS algorithms. Measurements were taken at 25° C. with a 660 nm laser light source and at an angle of 90°.

DLS Method B: DLS measurements were performed on a Nanosizer ZS (Malvern Instruments, Malvern, UK) and using disposable UV cuvettes (Brand macro, 2.5 mL and Brand semi-micro 1.5 mL, Brand GmbH+Co KG, Wertheim, Germany). The data were processed with Malvern Zetasizer software Version 7.10 or 7.01. Parameters of the particle size distribution were determined with non-negatively constrained least squares (NNLS) methods. Measurements were taken at 25° C. with a 633 nm laser light source in NIBS (Non-Invasive Back-Scatter) mode at an angle of 173°.

DLS Method C: DLS measurements were performed on a DynaPro Plate Reader II (Wyatt Technology, Santa Barbara, Calif., US) and using one of the following black, low volume, and non-treated plates: polystyrene 384 assay plate with clear bottom (Corning, N.Y., US), polystyrene 96 assay plate with clear bottom (Corning, N.Y., US), cyclo olefin polymer (COP) 384 assay plate with clear bottom (Aurora, Mont., US), or polystyrene 384 assay plate with clear bottom (Greiner Bio-One, Germany). The data were processed with the Dynamics software provided by Wyatt Technology. Parameters of the particle size distribution were determined with non-negatively constrained least squares (NNLS) methods using DynaLS algorithms. Measurements were taken at 25° C. with an 830 nm laser light source at an angle of 158°.

ThT Assay for the Assessment of Physical Stability

Low physical stability of a peptide solution may lead to amyloid fibril formation, which is observed as well-ordered, thread-like macromolecular structures in the sample, which eventually may lead to gel formation. Thioflavin T (ThT) is widely used to visualize and quantify the presence of misfolded protein aggregates. [Biancalana et al. (2010) Biochimica et Biophysica Acta. 1804 (7): 1405-1412]. When it binds to fibrils, such as those in amyloid aggregates, the dye displays a distinct fluorescence signature [Naiki et al. (1989) Anal. Biochem. 177, 244-249; LeVine (1999) Methods. Enzymol. 309, 274-284]. The time course for fibril formation often follows the characteristic shape of a sigmoidal curve and can be separated into three regions: a lag phase, a fast growth phase, and a plateau phase.

The typical fibril formation process starts with the lag phase in which the amount of partially folded peptide turned into fibrils is not significant enough to be detected. The lag-time corresponds to the time the critical mass of the nucleus is built. Afterwards, a drastic elongation phase follows and fibril concentration increases rapidly.

Investigations were carried out to determine fibrillation tendencies under stress conditions by shaking at 37° C. within Fluoroskan Ascent FL.

For the tests in Fluoroskan Ascent FL, 200 μL sample were placed into a 96 well mictrotiter plate PS, flat bottom, Greiner Fluotrac No. 655076. Plates were sealed with Scotch Tape (Quiagen). Samples were stressed by continuous cycles of 10 s shaking at 960 rpm and 50 s rest period at 37° C. The kinetic was monitored by measuring fluorescence intensity every 20 minutes.

Peptides were diluted in a buffer system to a final concentration of 3 mg/ml. 20 μL of a 10.1 mM ThT solution in H2O were added to 2 mL of peptide solution to receive a final concentration of 100 μM ThT. For each sample eight replicates were tested.

Tht buffer system A) 100 mM Acetate pH 4.5 including m-cresol (100 mM Natriumacetat trihydrat, pH adjustment using 2N CH3COOH, 2.7 mg/mL m-cresol) Tht buffer system B) 100 mM citrate buffer pH 6.0

In Vitro Cellular Assays for GLP-1, Glucagon and GIP Receptor Efficacy

Agonism of compounds for the receptors was determined by functional assays measuring cAMP response of HEK-293 cell lines stably expressing human GLP-1, GIP or glucagon receptor.

cAMP content of cells was determined using a kit from Cisbio Corp. (cat. no. 62AM4PEJ) based on HTRF (Homogenous Time Resolved Fluorescence). For preparation, cells were split into T175 culture flasks and grown overnight to near confluency in medium (DMEM/10% FBS). Medium was then removed and cells washed with PBS lacking calcium and magnesium, followed by proteinase treatment with accutase (Sigma-Aldrich cat. no. A6964). Detached cells were washed and resuspended in assay buffer (1×HBSS; 20 mM HEPES, 0.1% BSA, 2 mM IBMX) and cellular density determined. They were then diluted to 400000 cells/ml and 25 μl-aliquots dispensed into the wells of 96-well plates. For measurement, 25 μl of test compound in assay buffer was added to the wells, followed by incubation for 30 minutes at room temperature. After addition of HTRF reagents diluted in lysis buffer (kit components), the plates were incubated for 1 hr, followed by measurement of the fluorescence ratio at 665/616 nm. In vitro potency of agonists was quantified by determining the concentrations that caused 50% activation of maximal response (EC50).

Bioanalytical Screening Method for Quantification of Exendin-4 Derivatives in Mice and Pigs Mice were dosed 1 mg/kg subcutaneously (s.c.). The mice were sacrificed and blood samples were collected after 0.25, 0.5, 1, 2, 4, 8, 16 and 24 hours post application. Plasma samples were analyzed after protein precipitation via liquid chromatography mass spectrometry (LC/MS). PK parameters and half-life were calculated using WinonLin Version 5.2.1 (non-compartment model).

Female Göttinger minipigs were dosed 0.05 mg/kg, 0.075 mg/kg or 0.1 mg/kg subcutaneously (s.c.). Blood samples were collected after 0.25, 0.5, 1, 2, 4, 8, 24, 32, 48, 56 and 72 hours post application. Plasma samples were analyzed after protein precipitation via liquid chromatography mass spectrometry (LC/MS). PK parameters and half-life were calculated using WinonLin Version 5.2.1 (non-compartment model).

Acute and Chronic Effects After Subcutaneous Treatment on Blood Glucose, Body Mass, Whole Body Fat Content, and Feed Consumption in Female Diet-Induced Obese (DIO) C57BL/6 Mice Female C57BL/6NHsd mice were ordered group housed from Envigo RMS Inc., shipped group housed and remained group housed with shipped cage mates in shoebox caging with wood chip bedding until day 38 of the predose phase. At the study start mice were between 25-26 weeks old.

Mice were housed under vivarium conditions that included a 12 h light/dark cycle (light phase 04:00 AM-4:00 PM), room temperatures between 23-26° C. and a relative humidity between 30-70%. All animals had free access to water and a high fat diet (TD97366) for 16 weeks prior to pharmacological intervention (dosing phase). Feed was replaced with fresh feed weekly until and for the last time on day 38 of the predose phase. During the subsequent dosing phase, approximately 50% of the remaining feed were removed, replaced with fresh feed, and pellets were mixed evenly once per week.

On predose day 38, obese DIO mice were assigned to treatment groups (n=8) to match mean body masses between all DIO groups. An age-matched group with ad libitum access to a rodent maintenance diet (Teklad Global Diets Rodent 2014, pelleted) was included in the study as a lean control group. In the predosing phase from day 32 through 38, all study animals were treated with vehicle (Phosphate Buffered Saline, PBS, Gibco, without $CaCl_2$ and $MgCl_2$) once daily (s.c. approximately 0.2 mL/mouse).

On day 37 of the predose phase, the test article was diluted with PBS to a concentration of 100 μg/mL and aliquots of this stock solution were stored at approximately ≤−60° C. Stock aliquots were thawed for weekly use and thereafter stored in a refrigerator at approximately 4° C. The injected test article solution was prepared fresh once on each dosing day by diluting stock solution with PBS to achieve the desired concentration.

Mice were treated twice daily with a s.c. injection of PBS-vehicle or the test article for 28 days. The morning dosing was initiated and completed between 06:00 and 07:30 AM and the afternoon dosing between 2:00 and 3:30 PM. On day 28 of the dosing phase only the morning dose was administered. The applied volume was 5 ml/kg and the dose was adjusted to the most recent body mass recording of each individual.

1) Acute effect on blood glucose profiles in non-fasting, female DIO mice:

Animals had unlimited access to water and feed during the experiment. On day 1 of the dosing phase approximately 5 μL of blood were collected via tail clips at hour 0 prior to the first s.c. dose of PBS-vehicle or test article and 1, 2, 3, 4, 6, and 24 hours post-dose in non-anesthetized animals. The 24 hour blood collection was performed prior to dosing on day 2. Between the 6 and 24 hour blood sample the afternoon dose was administered. Glucose measurements were performed in whole blood and in duplicate or triplicate using Aviva glucometers.

2) Chronic effect on body mass in non-fasting, female DIO mice:

Body mass was measured daily approximately between 06:00-07:30 AM from day 32 through 38 of the predosing phase and throughout the 28 days of the dosing phase. During the dosing phase mice were treated twice daily with either a s.c. injection of PBS-vehicle or test article.

3) Chronic effect on whole body fat mass in non-fasting, female DIO mice:

To determine whole body fat mass Quantitative Nuclear Magnetic Resonance (QNMR) measurements were performed on predosing day 37 and on day 26 of the dosing phase. During the dosing phase mice were treated twice daily with either a s.c. injection of PBS-vehicle or test article.

4) Effect on feed consumption in female DIO mice:

Feed consumption was based on the daily assessment of the feeder weights of each cage between 06:00-07:30 AM. Each cage housed four mice and feed consumption was calculated throughout the 28 days of the dosing phase. During the dosing phase mice were treated twice daily with either a s.c. injection of PBS-vehicle or test article.

5) Terminal plasma parameters in non-fasting, female DIO mice:

On day 28 blood was collected prior to any other inlife activities for determination of plasma insulin concentrations. Then the morning dose was administered and necropsy was performed 4 hours post-dose. For this purpose animals were anesthetized with isoflurane and blood was collected by orbital bleeding.

5) Terminal liver mass in non-fasting, female DIO mice:

On day 28 and 4 hours after the morning dose, blood was collected from mice under isoflurane anesthesia as described above. Then mice were killed and livers were collected and weighed.

6) Quantification of liver lipids:

Liver aliquots were incubated with dichlormethane:methanol (2:1). The lipohilic and lipohobic phase were separated by adding $dH_2O$ and subsequent centrifugation. The bottom lipophilic phase was collected and the procedure repeated with the remaining lipophobic layer and liver tissue. Next the lipophilic phases were combined and the solvent evaporated. At 60° C. and continuous shaking samples were then incubated with 2-propanol. Total cholesterol, triacylglycerol and phospholipid concentrations were quantified enzymatically with a commercial kit according to the manufacturer's instructions.

7) Statistical analyses:

Statistical analyses were performed with Sigmaplot 12.5. Two-tailed T-Tests were used to compare groups of DIO-vehicle mice (in general n=8) with DIO-test article treated mice (in general n=8). When the difference in the mean values of the two groups was greater than 0.05 they were considered statistically significantly different. Lean-Vehicle group data are depicted in the Figures but were used as a reference dataset for the non-obese state.

Acute Effects After Subcutaneous Treatment on Blood Glucose Concentrations in Non-Fasting, Female, Diabetic db/db Mice Female healthy, lean BKS.Cg-(lean)/OlaHsd and diabetes-prone, obese BKS.Cg-+Lepr$^{db}$/+Lepr$^{db}$/OlaHsd mice were ordered group housed from Envigo RMS Inc., shipped group housed and remained group housed in shoebox caging with wood chip bedding until day 15 of the predose phase. At the study start mice were approximately 12 weeks old.

Mice were housed under vivarium conditions including a 12 h light/dark cycle (light phase 04:00 AM-4:00 PM), room temperatures between 23-26° C. and a relative humidity between 30-70%. All animals had free access to water and Purina Fomulab Diet 5008.

On predose day 9 blood glucose and body mass (approximately between 08:00-10:00 AM) as well as HbA1c measurements were performed. On day 15 of the predose phase animals were assigned to treatment groups (n=8) and to new cages to match mean HbA1c and body masses between all db/db groups. An age-matched lean group was included in the study as a healthy, lean reference.

Prior to day 1 of the dosing phase, the test article was diluted with Phosphate Buffered Saline (PBS, Gibco, without $CaCl_2$ and $MgCl_2$) to a concentration of 1 mg/mL and aliquots of this stock solution were stored at approximately ≤−60° C. On day 1 of the dosing phase the stock aliquot was thawed and the injected test article solution was prepared fresh by diluting it with PBS to achieve the desired concentration.

On Day 1 of the dosing phase db/db mice were either treated once with a s.c. injection of PBS-vehicle or 30 μg/kg test article. The lean reference group was treated once with a s.c. injection of PBS-vehicle. The dosing was initiated and completed between 08:00 and 10:00 AM. The applied volume was 5 ml/kg and the dose was adjusted to the most recent body mass recording of each individual.

1) Acute effect on blood glucose profiles in non-fasting animals:

Animals had unlimited access to water and feed during the experiment. On day 1 of the dosing phase approximately 5 μL of blood were collected via tail clips at minute −30 and 0 prior to any other inlife activities. At minute 0 mice received a s.c. dose of either PBS-vehicle or 30 μg/kg test article. Further blood samples were harvested at hour 0.25, 0.5, 1, 1.5, 2, 3, 4, 6, 8, and 24 post-dose. Glucose measurements were performed in whole blood using Alpha-TRAK glucometers. If the glucose concentrations of two measurements differed by more than 20 mg/dL a third value was recorded. The Area Under the Curve (AUC) for blood glucose was calculated via the trapezoid method and for the duration of the 24 post-dose hours.

2) Statistical analyses:

In the Figures data are depicted as means±SEM. Statistical analyses were performed with Sigmaplot 12.5. A One Way Analysis of Variance and multiple comparisons (Dunnett's Method) were performed comparing the group of diabetic, obese db/db vehicle mice (n=8) with each diabetic, obese db/db test article treated mice (n=8). When the difference in the mean values of the two groups was greater than 0.05 they were considered statistically significantly different. Non-diabetic, lean-vehicle group data are depicted in the Figures serving as a reference dataset for the non-obese, non-diabetic state.

EXAMPLES

The invention is further illustrated by the following examples.

Example 1

Synthesis of SEQ ID NO: 6

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.43 mmol/g. The Fmoc-synthesis strategy was applied with HBTU/DIPEA-activation. In position 14 Fmoc-Lys(Mmt)-OH and in position 1 Boc-His(Trt)-OH were used in the solid phase synthesis protocol. The Mmt-group was cleaved from the peptide on resin as described in the methods. Hereafter Palm-gGlu-gGlu-OSu was coupled to the liberated amino-group employing DIPEA as base. The peptide was cleaved from the resin with King's cocktail (D. S. King, C. G. Fields, G. B. Fields, Int. J. Peptide Protein Res. 1990, 36, 255-266). The crude product was purified via preparative HPLC on a Waters column (RP18 XSelectCSH-5 μm 50×150 mm) using an acetonitrile/water gradient (both buffers with 0.1% TFA). The purified peptide was analysed by LCMS (Method B).

Deconvolution of the mass signals found under the peak with retention time 8.737 min revealed the peptide mass 4932.68 which is in line with the expected value of 4932.67.

Example 2

Synthesis of SEQ ID NO: 11

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.43 mmol/g. The Fmoc-synthesis strategy was applied with HBTU/DIPEA-activation. In position 14 Fmoc-Lys(Mmt)-OH and in position 1 Boc-His(Trt)-OH were used in the solid phase synthesis protocol. The Mmt-group was cleaved from the peptide on resin as described in the Methods. Hereafter Palm-gGlu-gGlu-OSu was coupled to the liberated amino-group employing DIPEA as base. The peptide was cleaved from the resin with King's cocktail (D. S. King, C. G. Fields, G. B. Fields, Int. J. Peptide Protein Res. 1990, 36, 255-266). The crude product was purified via preparative HPLC on a Waters column (Sunfire Prep C18 ODB 5 μm 30×250 mm) using an acetonitrile/water gradient (both buffers with 0.1% TFA). The purified peptide was analysed by LCMS (Method B).

Deconvolution of the mass signals found under the peak with retention time 9.995 min revealed the peptide mass 4863.67 which is in line with the expected value of 4863.63.

Example 3

Synthesis of SEQ ID NO: 20

The solid phase synthesis as described in Methods was carried out on Novabiochem Rink-Amide resin (4-(2',4'-Dimethoxyphenyl-Fmoc-aminomethyl)-phenoxyacetamido-norleucylaminomethyl resin), 100-200 mesh, loading of 0.43 mmol/g. The Fmoc-synthesis strategy was applied with HBTU/DIPEA-activation. In position 14 Fmoc-Lys(Mmt)-OH and in position 1 Boc-His(Trt)-OH were used in the solid phase synthesis protocol. The Mmt-group was cleaved from the peptide on resin as described in the Methods. Hereafter Palm-gGlu(OSu)-OtBu (CAS 204521-63-1) was coupled to the liberated amino-group employing DIPEA as base. The peptide was cleaved from the resin with King's cocktail (D. S. King, C. G. Fields, G. B. Fields, Int. J. Peptide Protein Res. 1990, 36, 255-266). The crude product was purified via preparative HPLC on a Waters column (Sunfire Prep C18 ODB 5 μm 30×250 mm) using an acetonitrile/water gradient (both buffers with 0.1% TFA). The purified peptide was analysed by LCMS (Method B).

Deconvolution of the mass signals found under the peak with retention time 8.837 min revealed the peptide mass 4763.670 which is in line with the expected value of 4763.617.

In an analogous way, the other peptides listed in Table 3 were synthesized and characterized.

TABLE 3 list of synthesized peptides and comparison of calculated vs. found molecular weight

| SEQ ID NO | calc. Mass | found mass | Monoisotopic or average mass | Retention time (min) |
|---|---|---|---|---|
| 6 | 4932.7 | 4932.7 | monoisotopic | 8.737 |
| 7 | 4946.7 | 4946.7 | monoisotopic | 8.699 |
| 8 | 4892.7 | 4892.7 | monoisotopic | 9.376 |
| 9 | 4906.7 | 4906.7 | monoisotopic | 9.505 |
| 10 | 4849.6 | 4849.7 | monoisotopic | 9.758 |
| 11 | 4863.6 | 4863.7 | monoisotopic | 9.995 |
| 12 | 4889.6 | 4889.7 | monoisotopic | 8.971 |
| 13 | 4903.6 | 4903.6 | monoisotopic | 9.184 |
| 14 | 5077.8 | 5077.8 | monoisotopic | 8.599 |
| 15 | 5091.8 | 5091.8 | monoisotopic | 8.839 |
| 16 | 4734.6 | 4734.7 | monoisotopic | 9.589 |
| 17 | 4762.6 | 4762.7 | monoisotopic | 10.278 |
| 18 | 4720.6 | 4720.6 | monoisotopic | 9.992 |
| 19 | 4748.6 | 4748.3 | monoisotopic | 10.822 |
| 20 | 4763.6 | 4763.7 | monoisotopic | 8.837 |
| 21 | 4791.6 | 4791.7 | monoisotopic | 9.674 |
| 22 | 5094.8 | 5094.8 | average | n.a. |
| 23 | 5108.9 | 5107.2 | average | n.a. |
| 24 | 5011.8 | n.a. | n.a. | n.a. |
| 25 | 5025.8 | n.a. | n.a. | n.a. |
| 26 | 4997.8 | n.a. | n.a. | n.a. |
| 27 | 5011.8 | n.a. | n.a. | n.a. |

Example 4

Stability

Peptide samples were prepared in Chemical stability buffer system A and the stability was assessed as described in Methods. The results are given in Table 4.

TABLE 4

| | stability |
|---|---|
| SEQ ID NO | Chemical stability [relative purity loss 28 days 40° C.] (%) at pH 4.5 |
| 6 | 7.1 |
| 7 | 8.1 |
| 8 | 10.3 |
| 9 | 6.9 |
| 10 | 10.6 |
| 11 | 8.8 |
| 12 | 11.9 |
| 13 | 10.5 |
| 14 | 8.1 |
| 15 | 7.2 |
| 22 | 9.5 |
| 23 | 8.6 |

Example 5

Solubility

Peptide samples were prepared in solubility buffer system A and solubility was assessed as described in Methods. The results are given in Table 5.

TABLE 5

Solubility

| SEQ ID NO | Solubility [mg/ml] at pH 4.5 |
|---|---|
| 6 | >9.7 |
| 8 | 9.5 |
| 9 | >9.3 |
| 10 | >9.8 |
| 11 | >9.8 |

Example 6

Stability as Assessed by DLS Interaction Parameter

The hydrodynamic radius $R_h$ of peptide samples was determined at different peptide concentrations (1 mg/ml and 5 mg/ml) in DLS buffer system A using DLS method C as described in Methods as surrogate for the DLS interaction parameter $k_D$. The results are given in Table 6.

TABLE 6 hydrodynamic radius $R_h$ at peptide concentrations of 1 mg/ml and 5 mg/ml. A decrease of $R_h$ at the higher peptide concentration indicates higher physical stability due to repulsive inter-particle interactions.

| SEQ. ID | $R_{h1}$ [nm] c = 1 mg/ml | $R_{h5}$ [nm] c = 5 mg/ml | Delta $R_h$ [nm] = $R_{h5} - R_{h1}$ |
|---|---|---|---|
| 6 | 2.5 | 1.7 | −0.9 |
| 8 | 3.0 | 2.6 | −0.4 |
| 9 | 2.8 | 2.6 | −0.2 |
| 12 | 2.9 | 2.6 | −0.3 |
| 13 | 2.8 | 2.5 | −0.3 |
| 14 | 3.0 | 2.9 | −0.1 |
| 15 | 3.0 | 2.6 | −0.4 |

Example 7

Stability was Assessed in the ThT Assay

Lag time in hours in Thioflavin T (ThT) assay of peptide samples was determined in ThT buffer system A as described in Methods. The results are given in Table 7.

TABLE 7

Lag time in hours in Thioflavin T (ThT) assay

| SEQ ID NO | Increase in Fl at pH 4.5 | Lag time before increase [h] |
|---|---|---|
| 6 | NO | >45 |
| 7 | NO | >45 |
| 8 | NO | >45 |
| 9 | NO | >45 |
| 10 | NO | >45 |
| 11 | NO | >45 |
| 12 | NO | >45 |
| 13 | NO | >45 |
| 14 | NO | >45 |
| 15 | NO | >45 |
| 16 | NO | >45 |
| 17 | NO | >45 |
| 18 | NO | >45 |
| 19 | NO | >45 |
| 20 | NO | >45 |
| 21 | NO | >45 |

TABLE 7-continued

Lag time in hours in Thioflavin T (ThT) assay

| SEQ ID NO | Increase in Fl at pH 4.5 | Lag time before increase [h] |
|---|---|---|
| 22 | NO | >45 |
| 23 | NO | >45 |

Example 8

In Vitro Data on GLP-1, Glucagon and GIP Receptor

Potencies of peptidic compounds at the GLP-1, glucagon and GIP receptors were determined by exposing cells expressing human glucagon receptor (hGlucagon R), human GIP receptor (hGIP-R) or human GLP-1 receptor (hGLP-1 R) to the listed compounds at increasing concentrations and measuring the formed cAMP as described in Methods.

The results are shown in Table 8:

TABLE 8

EC50 values of exendin-4 derivatives at human GLP-1, Glucagon and GIP receptors (indicated in pM)

| SEQ ID NO | EC50 hGLP-1R | EC50 hGlucagon R | EC50 hGIP R |
|---|---|---|---|
| 6 | 1.4 | 2.3 | 2.1 |
| 7 | 1.7 | 3.2 | 2.6 |
| 8 | 1.3 | 2.0 | 1.6 |
| 9 | 1.6 | 2.9 | 2.6 |
| 10 | 2.3 | 1.6 | 1.1 |
| 11 | 2.9 | 2.1 | 1.5 |
| 12 | 1.8 | 2.0 | 1.9 |
| 13 | 2.8 | 2.1 | 2.7 |
| 14 | 0.9 | 3.4 | 1.2 |
| 15 | 1.1 | 4.5 | 1.8 |
| 16 | 7.1 | 4.3 | 3.7 |
| 17 | 6.4 | 5.3 | 7.3 |
| 18 | 5.3 | 2.8 | 2.0 |
| 19 | 6.1 | 3.1 | 4.0 |
| 20 | 4.8 | 4.2 | 1.9 |
| 21 | 3.4 | 1.9 | 2.6 |
| 22 | 1.0 | 5.9 | 1.1 |
| 23 | 1.4 | 6.8 | 1.5 |

Example 9

Comparison Testing

A selection exendin-4 derivatives carrying (among others) a His in position 1, Leu in position 13, Glu in position 15, Gln in position 19, an Aib amino acid in position 34, Pro at position 32 and Lys at position 35 and 39 has been tested versus corresponding compounds having in these positions the amino acid residues of native exendin-4 or other amino acids. The reference pair compounds and the corresponding EC50 values at human GLP-1, Glucagon and GIP receptors (indicated in pM) are given in Table 9. As shown, the inventive exendin-4 derivatives show an improved activity on the GIP receptor compared to the corresponding derivatives carrying the amino acids as in native exendin-4 or other amino acids, keeping their GLP-1 receptor and glucagon receptor activity.

TABLE 9

Comparison of exendin-4 derivatives carrying a His in position 1, Leu in position 13, Glu in position 15, Gln in position 19, an Aib amino acid in position 34, Pro at position 32 and Lys at position 35 and 39 vs. exendin-4 derivatives comprising at these positions the amino acid residues of native exendin-4 (Lys27, Ser32, Gly34, Ala35, Ser39) or other amino acids. EC50 values at human GLP-1, Glucagon and GIP receptors are indicated in pM.

| SEQ ID NO | EC50 hGLP-1R | EC50 hGlucagon-R | EC50 hGIP-1 | residue differences |
|---|---|---|---|---|
| 28 | 2.5 | 1.9 | 39.7 | Gln3, Gln13, Asp15, Ala19, Ser32, Gly34, Ala35, Ser39 |
| 21 | 3.4 | 1.9 | 2.6 | His3, Leu13, Glu15, Gln19, Pro32, Aib34, Lys35, Lys39 |
| 29 | 15.1 | 1.2 | 23.0 | Tyr1, Gln3, Gln13, Asp15, Ala19, Ser28, Ser32, Gly34, Ala35, Ser39 |
| 21 | 3.4 | 1.9 | 2.6 | His1, His3, Leu13, Glu15, Gln19, Ala28, Pro32, Aib34, Lys35, Lys39 |

Example 10

Acute and Chronic Effects of SEQ ID NO: 6 After Subcutaneous Treatment on Blood Glucose, Body Mass, Whole Body Fat Content, Feed Consumption, Terminal Liver Weight and Terminal Plasma Parameters in Fed, Female Diet-Induced Obese (DIO) C57BL/6 Mice Animals, Study Design (Predosing Phase, Dosing Phase), Pharmacological Intervention:

1) Blood glucose profile in morning-fed animals

Animals had unlimited access to water and feed during the experiment. Blood glucose concentrations were determined on day 1 of the dosing phase at hour 0 prior to the first s.c. injection of PBS-vehicle or 30 µg/kg SEQ ID NO: 6 and then 1, 2, 3, 4, 6, and 24 hours post-dose. Between the 6 and 24 hour blood sample the afternoon dose was administered.

Figure 2:
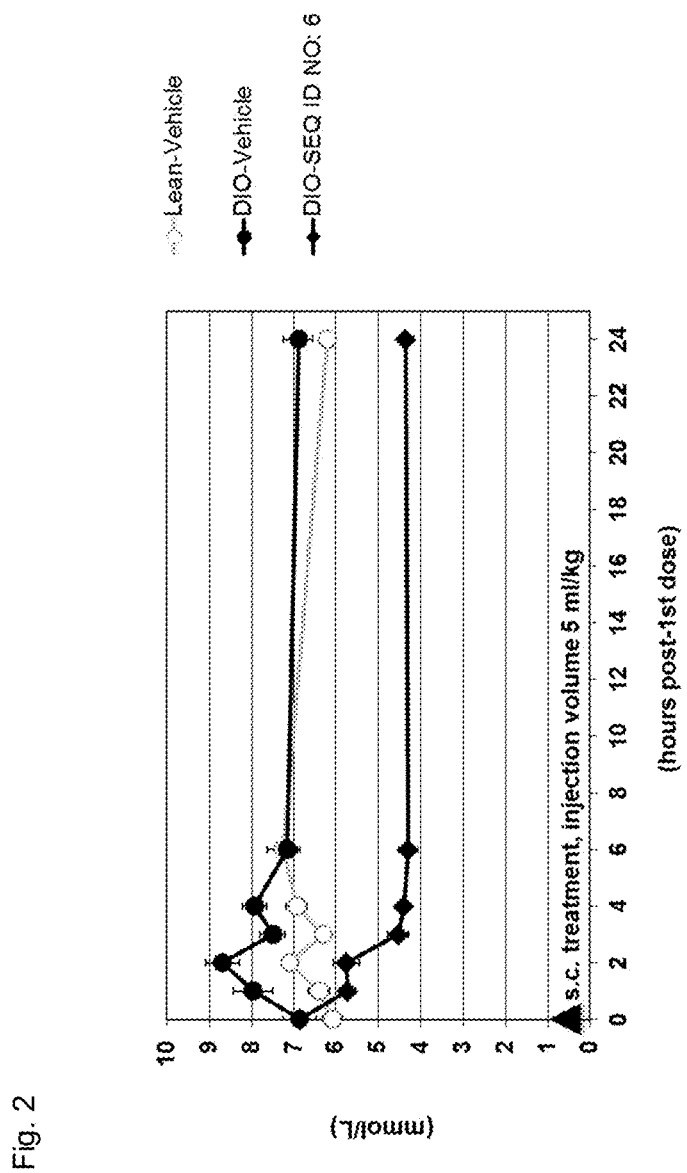

SEQ ID NO: 6 treated animals demonstrated a pronounced decrease in blood glucose concentrations over 24 hours. In contrast, no such change in blood glucose concentrations was observed in DIO control mice (FIG. 2).

2) Body mass

Figure 3:
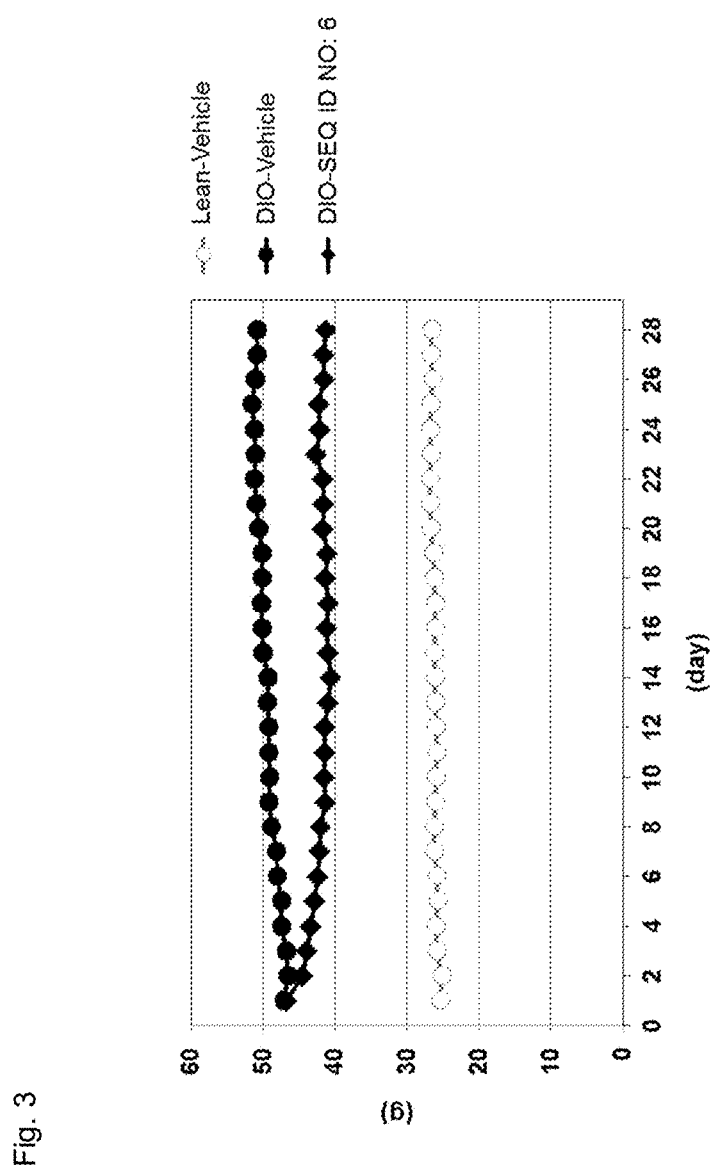
Figure 4:
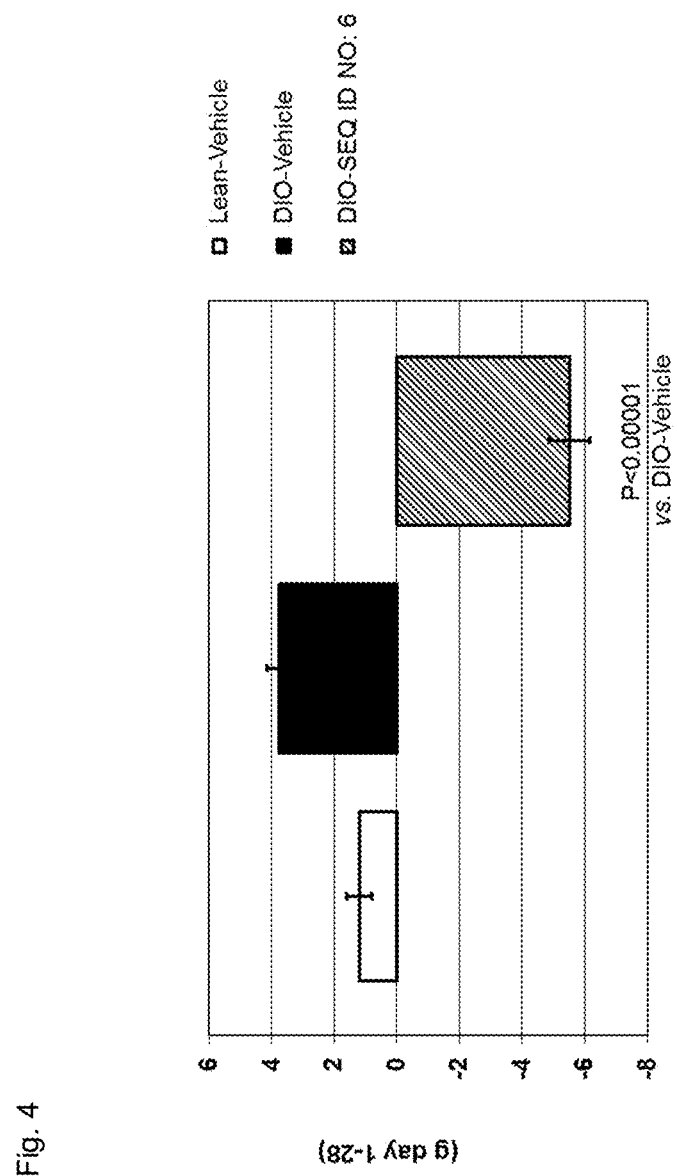

Twice-daily, chronic treatment of DIO animals with 30 µg/kg SEQ ID NO: 6 induced a consistent decrease in body mass over the 28 days of the treatment phase compared to the vehicle DIO group (FIG. 3). Chronic, twice daily treatment with SEQ ID NO: 6 resulted in a statistically significantly more pronounced body mass reduction within the 28 days of the dosing phase compared to DIO animals treated with vehicle (FIG. 4, Table 10).

3) Whole Body Fat Mass

Whole body fat mass measurements were performed on predosing day 37 and on day 26 of the dosing phase.

Figure 5:
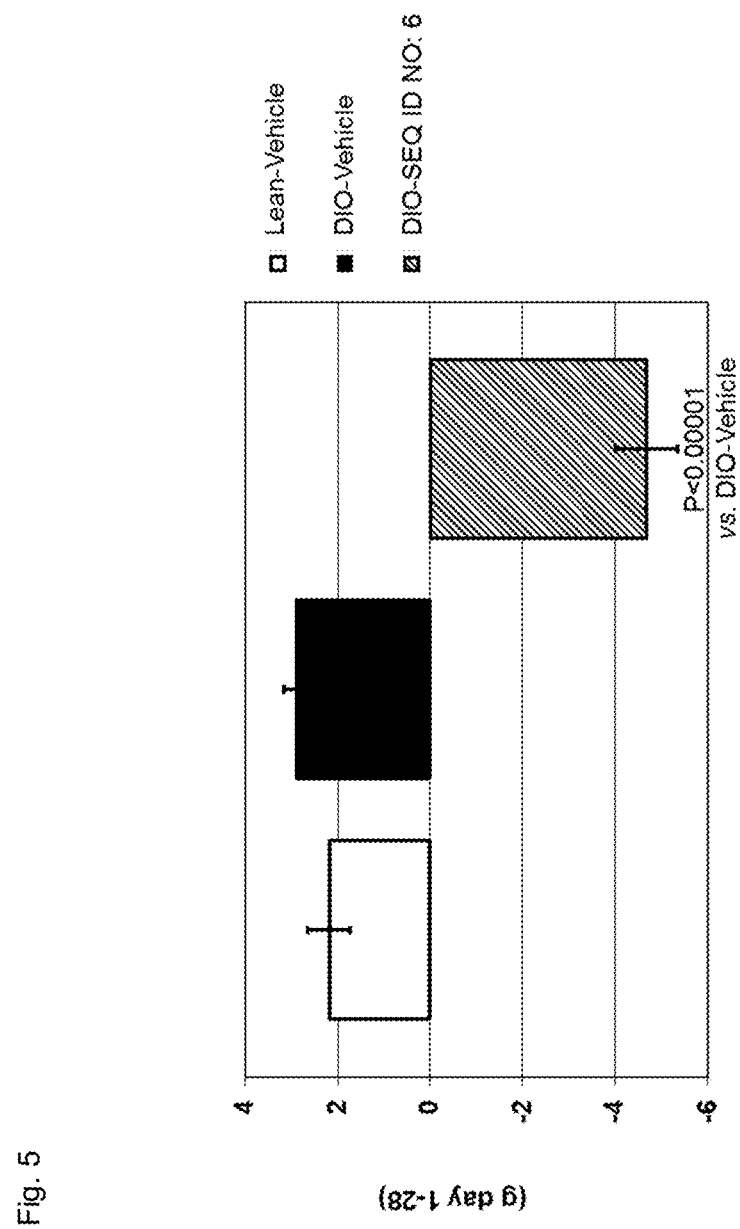

In parallel to the pronounced body mass loss, twice-daily, chronic treatment of DIO animals with 30 µg/kg SEQ ID NO: 6 resulted in a statistically significantly more pronounced whole body fat mass reduction during the 28 days of the dosing phase compared to DIO-Vehicle animals (FIG. 5, Table 10).

4) Feed Consumption

Each cage housed four mice and feed consumption was estimated throughout the 28 days of the dosing phase.

Figure 6:
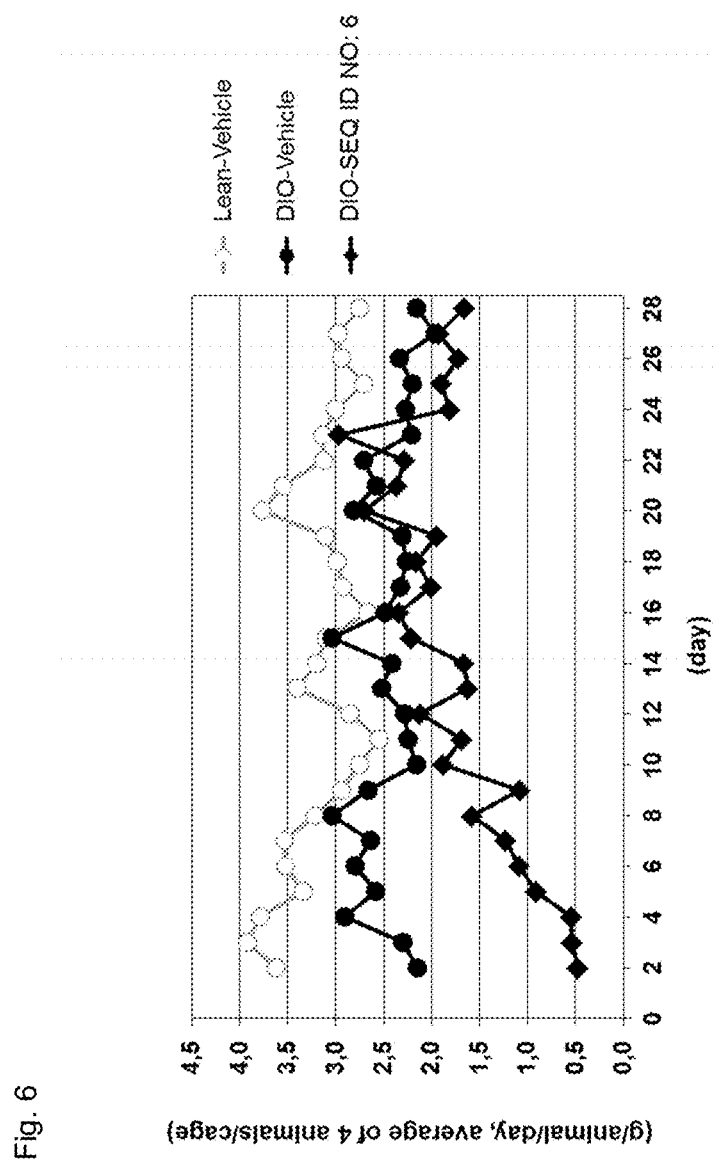

After dosing start, twice-daily, chronic treatment with 30 µg/kg SEQ ID NO: 6 suppressed feed intake, however mice habituated to the pharmacological effects within approximately ten days. Thereafter, the estimated feed consumption was comparable between the SEQ ID NO: 6 and DIO-Vehicle group (FIG. 6).

5) Terminal Liver Mass

On day 28 mice were euthanized 4 hours after the morning dose and livers were collected.

Figure 7:
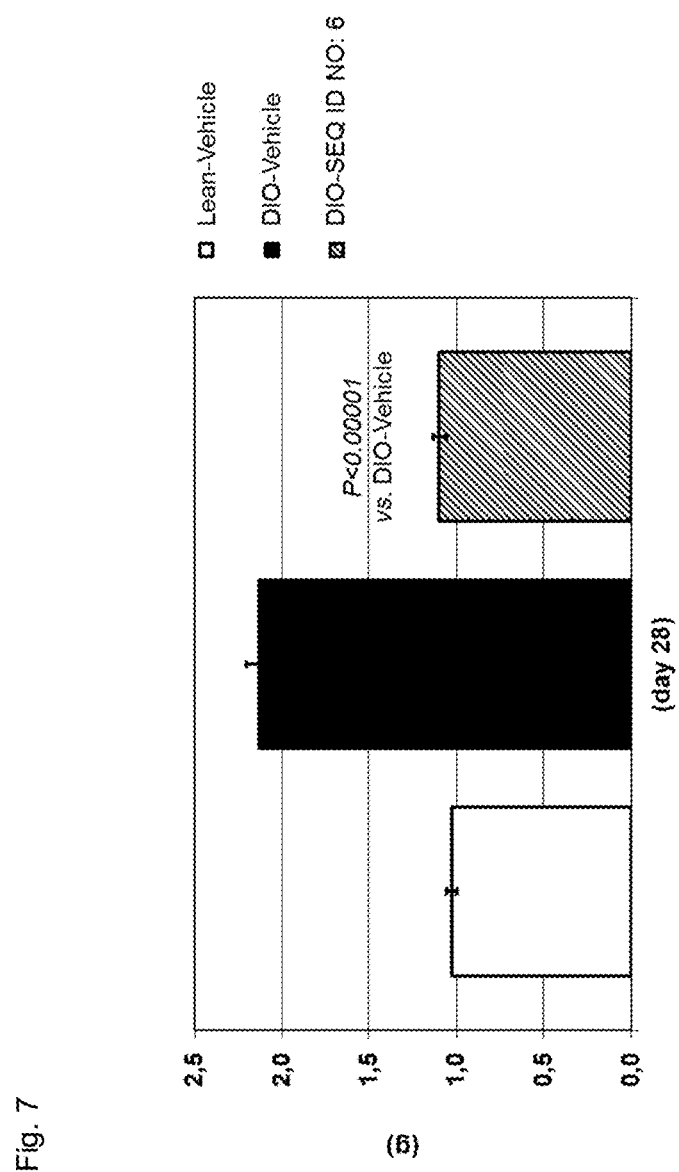

Twice-daily, chronic treatment of DIO animals with 30 µg/kg SEQ ID NO: 6 resulted in a statistically significant reduction in liver mass on day 28 of the dosing phase compared to DIO animals treated with vehicle (FIG. 7, Table 10).

6) Terminal plasma triglycerides and LDL

On day 28 and 4 hours after the morning dose, blood was collected from anesthetized, non-fasting mice by orbital bleeding. Twice-daily, chronic treatment of DIO animals with 30 µg/kg SEQ ID NO: 6 resulted in a statistically significant reduction in non-fasting plasma triglycerides (FIG. 8, Table 10) and plasma LDL concentrations (FIG. 9, Table 10) compared to DIO animals treated with vehicle.

7) Statistical Analyses

In the Figures data are depicted as means±SEM. Statistical analyses were performed with Sigmaplot 12.5. Two-tailed T-Tests were used to compare groups of DIO-vehicle mice (n=8) with DIO-test article treated mice (n=8). When the difference in the mean values of the two groups was greater than 0.05 they were considered statistically significantly different. Lean-Vehicle group data are depicted in the Figures serving as a reference dataset for the non-obese state.

TABLE 10

Effects resulting from 28 days subcutaneous treatment with SEQ ID NO: 6 in fed, female diet-induced obese (DIO) C57BL/6 mice.

| Parameter | DIO-Vehicle twice-daily PBS | DIO-SEQ ID NO: 6 twice-daily 30 µg/kg |
|---|---|---|
| Body mass change (g) | +3.76 ± 0.40 | −5.51 ± 0.64 $P < 0.00001$ |
| Whole body fat mass change (g) | +2.89 ± 0.27 | −4.68 ± 0.67 $P < 0.00001$ |
| Terminal liver mass (g) | 2.13 ± 0.08 | 1.10 ± 0.04 $P < 0.00001$ |
| Terminal plasma triglyceride (mmol/L) | 0.64 ± 0.08 | 0.28 ± 0.04 $P < 0.001$ |
| Terminal plasma LDL (mmol/L) | 1.28 ± 0.06 | 0.70 ± 0.06 $P < 0.00001$ |

Data are means ± SEM.
n = 8/group.

Example 11

Acute and Chronic Effects of SEQ ID NO: 11 After Subcutaneous Treatment on Blood Glucose, Body Mass, Whole Body Fat Content, Feed Consumption, Terminal Liver Weight and Terminal Plasma Parameters in Fed, Female Diet-Induced Obese (D1O) C57BL/6 Mice Animals, Study Design (Predosing Phase, Dosing Phase), Pharmacological Intervention:

Mice were treated twice daily with a s.c. injection of PBS-vehicle or 30 µg/kg SEQ ID NO: 11 for 28 days, except on day 1 and 28 when mice received a single dose. The morning dosing was initiated and completed between 06:00 and 07:30 AM and the afternoon dosing between 2:00 and 3:30 PM. On day 1 and day 28 of the dosing phase only the morning dose was administered. The applied volume was 5 ml/kg and the dose was adjusted to the most recent body mass recording of each individual.

1) Blood Glucose Profile in Morning-Fed Animals

Figure 10:
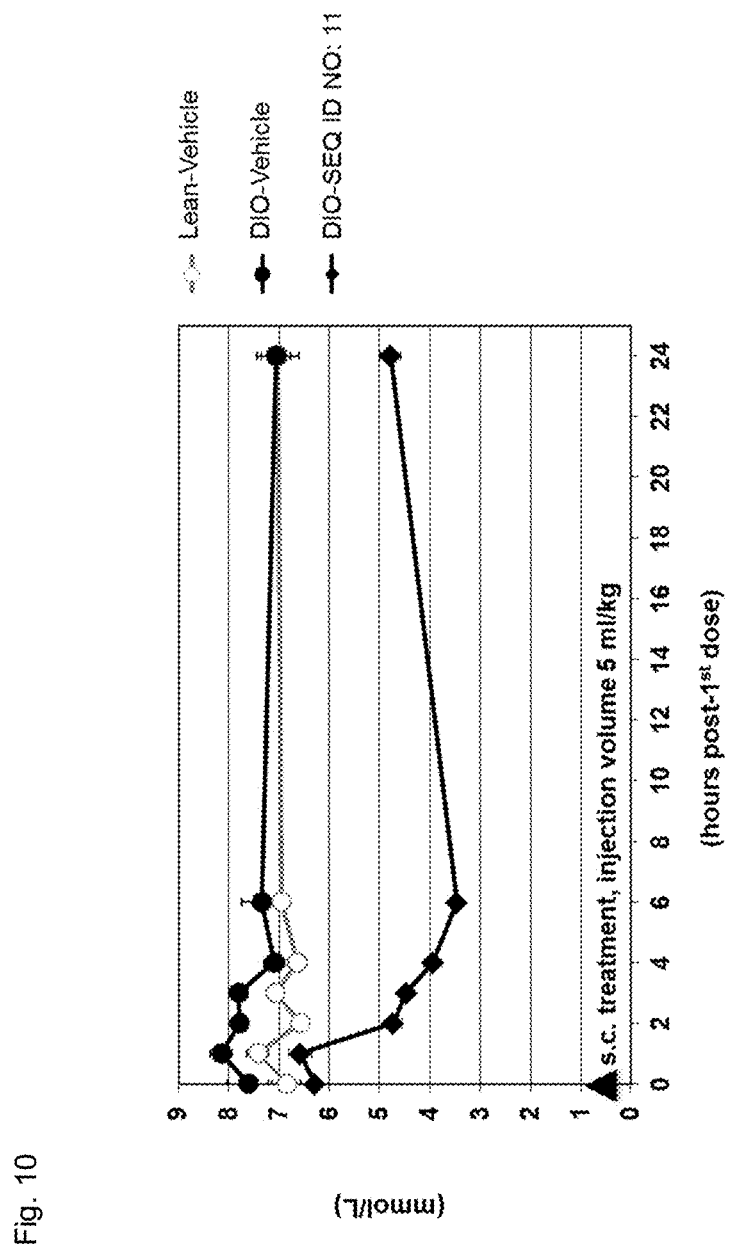

Animals had unlimited access to water and feed during the experiment. On day 1 of the dosing phase approximately 5 µL of blood were collected via tail clips at hour 0 prior to the first s.c. dose of PBS-vehicle or 30 µg/kg SEQ ID NO: 11 and 1, 2, 3, 4, 6, and 24 hours post-dose in non-anesthetized animals. The 24 hour blood collection was performed prior to dosing on day 2. Glucose measurements were performed in whole blood and in duplicate or triplicate using Aviva glucometers SEQ ID NO: 11 treated animals demonstrated a pronounced decrease in blood glucose concentrations that persisted over 24 hours. In contrast, no such change in blood glucose concentrations was observed in DIO control mice (FIG. 10).

2) Body Mass

Figure 11:
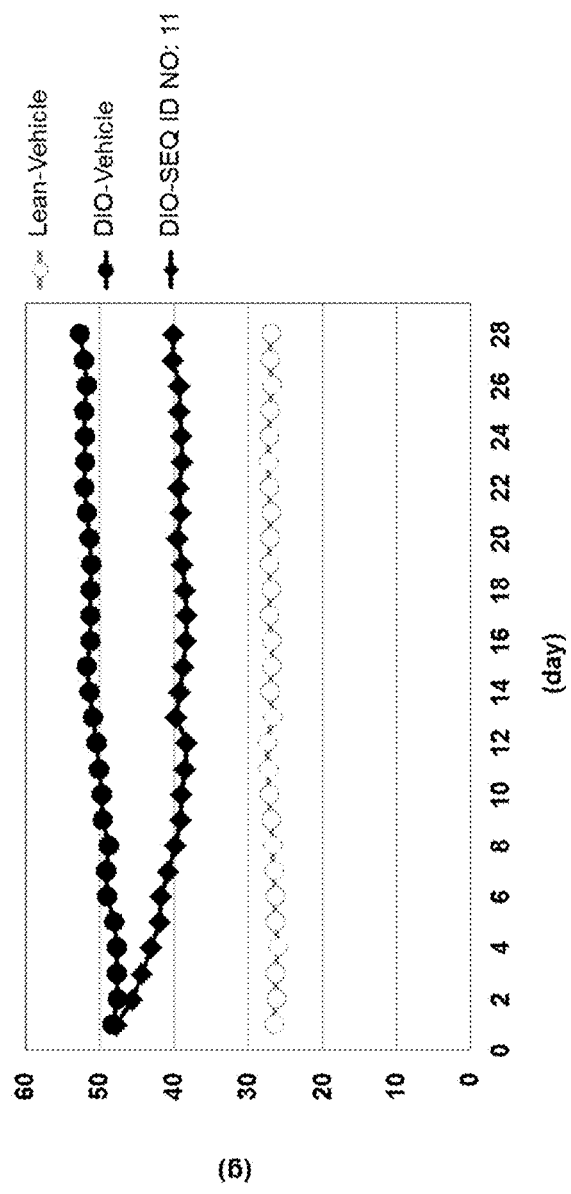
Figure 12:
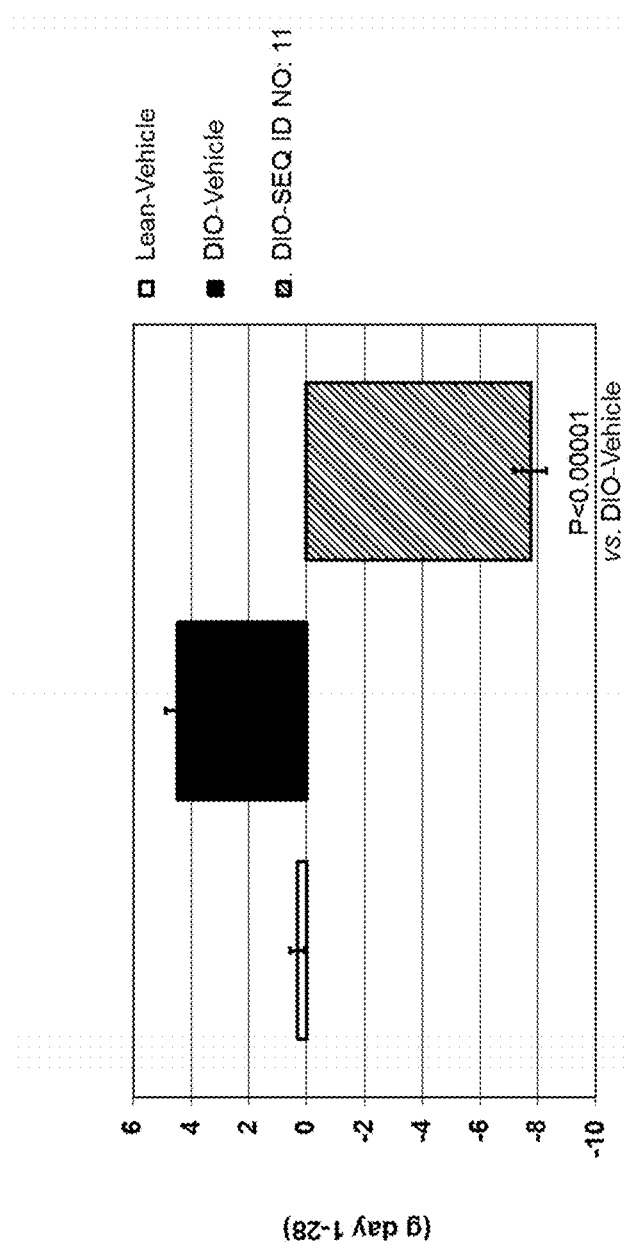

Body mass was measured daily approximately between 06:00-07:30 AM from day 32 through 38 of the predosing phase and throughout the 28 days of the dosing phase. During the dosing phase, except on day 1 and 28, animals were treated twice daily with either a s.c. injection of PBS-vehicle or 30 µg/kg SEQ ID NO: 11. Chronic treatment of DIO animals with 30 µg/kg SEQ ID NO: 11 induced a consistent decrease in body mass over the 28 days of the treatment phase compared to the vehicle DIO group (FIG. 11). Chronic, twice daily treatment with SEQ ID NO: 11 resulted in a statistically significantly more pronounced body mass reduction within the 28 days of the dosing phase compared to DIO animals treated with vehicle (T-Test, Two-Tailed P<0.001, FIG. 12, Table 11).

3) Whole Body Fat Mass

To determine whole body fat mass Quantitative Nuclear Magnetic Resonance (QNMR) measurements were performed on predosing day 37 and on day 26 of the dosing phase. During the dosing phase mice were treated twice daily with either a s.c. injection of PBS-vehicle or 30 µg/kg SEQ ID NO: 11.

Figure 13:
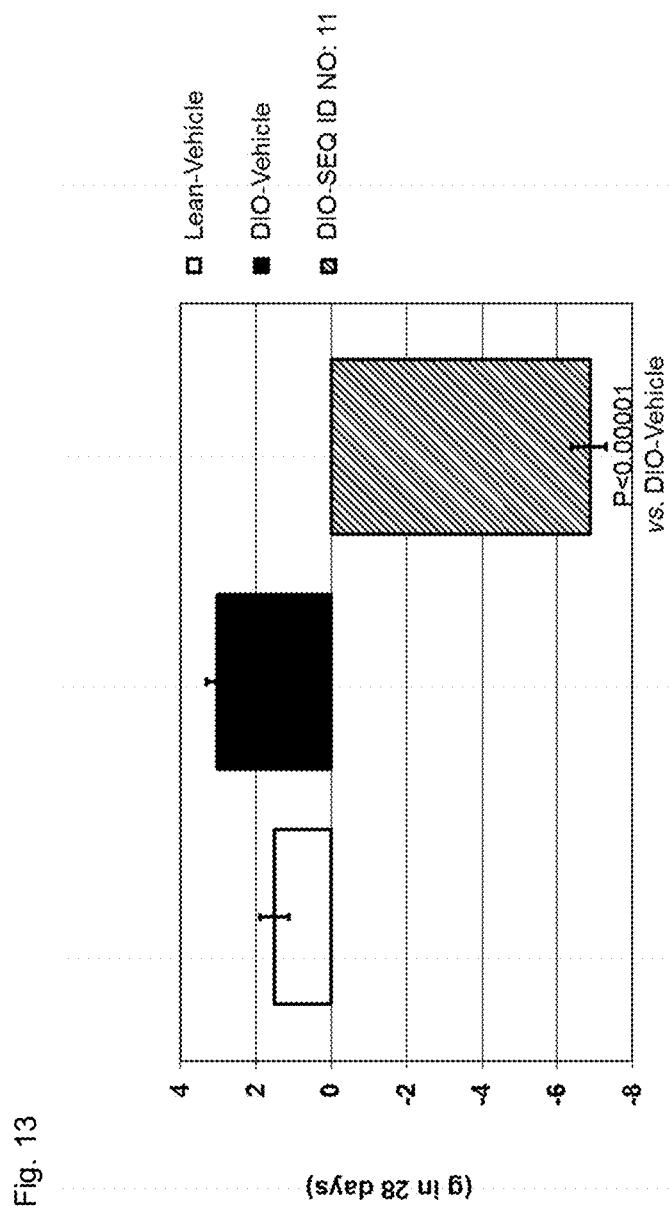

In parallel to the pronounced body mass loss, twice-daily, chronic treatment of DIO animals with 30 µg/kg SEQ ID NO: 11 resulted in a statistically significantly more pronounced whole body fat mass reduction during the 28 days of the dosing phase compared to DIO animals treated with vehicle (T-Test, Two-Tailed P<0.001, FIG. 13, Table 11).

3) Feed Consumption

Feed consumption was estimated based on the daily assessment of the feeder weights between 06:00-07:30 AM. Each cage housed four mice and feed consumption was determined throughout the 28 days of the dosing phase. During the dosing phase mice were treated twice daily with either a s.c. injection of PBS-vehicle or 30 µg/kg SEQ ID NO: 11.

Figure 14:
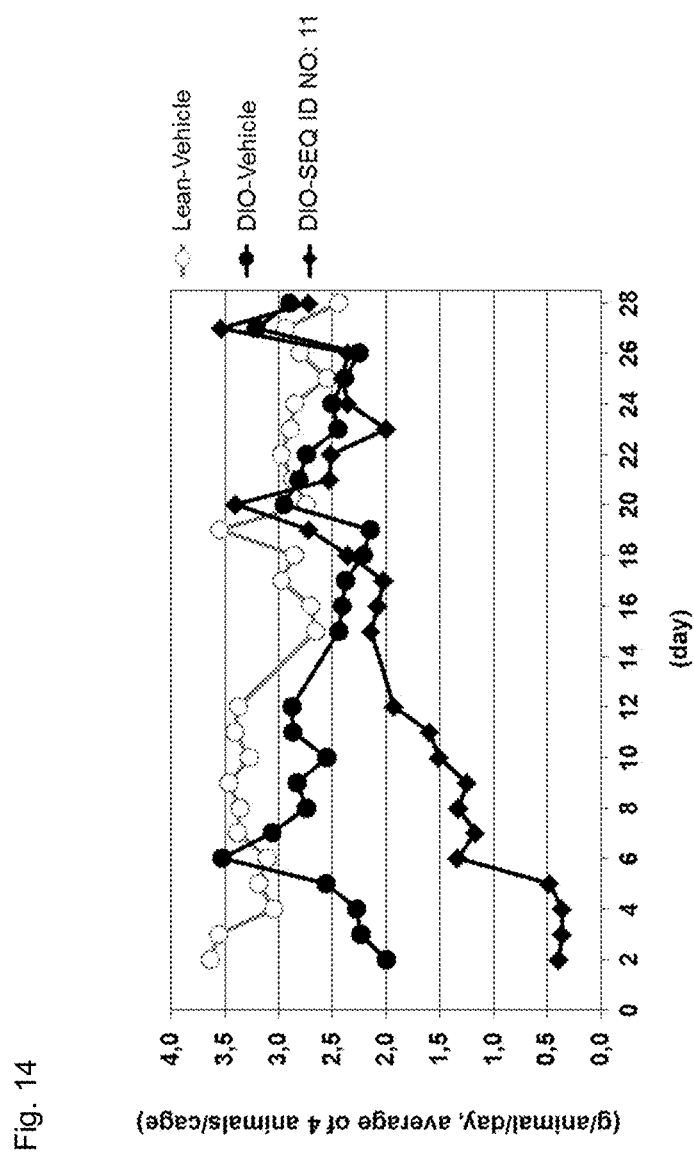

After dosing start, treatment with 30 µg/kg SEQ ID NO: 11 suppressed feed intake, however mice habituated to the pharmacological effects within approximately 15 days. After day 15 in the dosing phase, the estimated feed consumption was similar between SEQ ID NO: 11 and vehicle treated DIO mice (FIG. 14).

4) Terminal Liver Mass

On day 28 blood was collected, then the morning dose was administered and necropsy was performed 4 hours post-dose. For this purpose animals were euthanized by isoflurane anesthesia, blood was collected by orbital bleeding followed by cervical dislocation, decapitation, bilateral thoracotomy, exsanguination, or vital organ removal to ensure death following last blood collection. Then the liver was collected and liver mass was recorded.

Figure 15:
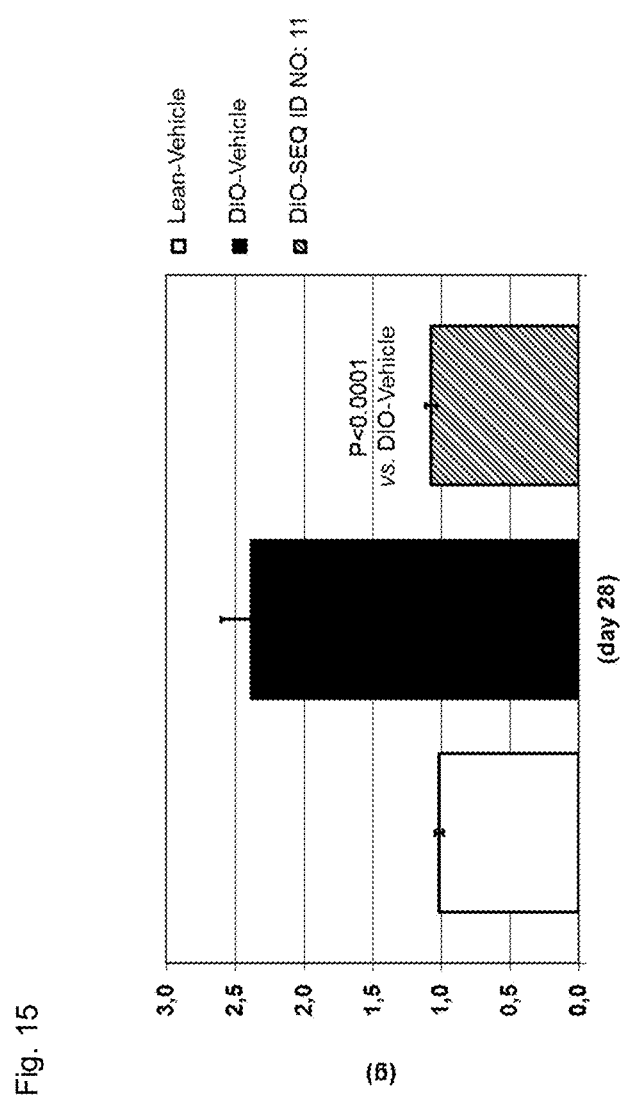

Twice-daily, chronic treatment of DIO animals with 30 µg/kg SEQ ID NO: 11 resulted in a statistically significant reduction in liver mass on day 28 of the dosing phase compared to DIO animals treated with vehicle (T-Test, Two-Tailed P<0.001, FIG. 15, Table 11).

5) Terminal Plasma Triglycerides, LDL, Insulin and Glucose

On day 28 blood was collected, then the morning dose was administered and necropsy was performed four hours post-dose. For this purpose non-fasting animals were euthanized by isoflurane anesthesia and blood was collected by orbital bleeding for measurement of plasma parameters.

Figure 19:
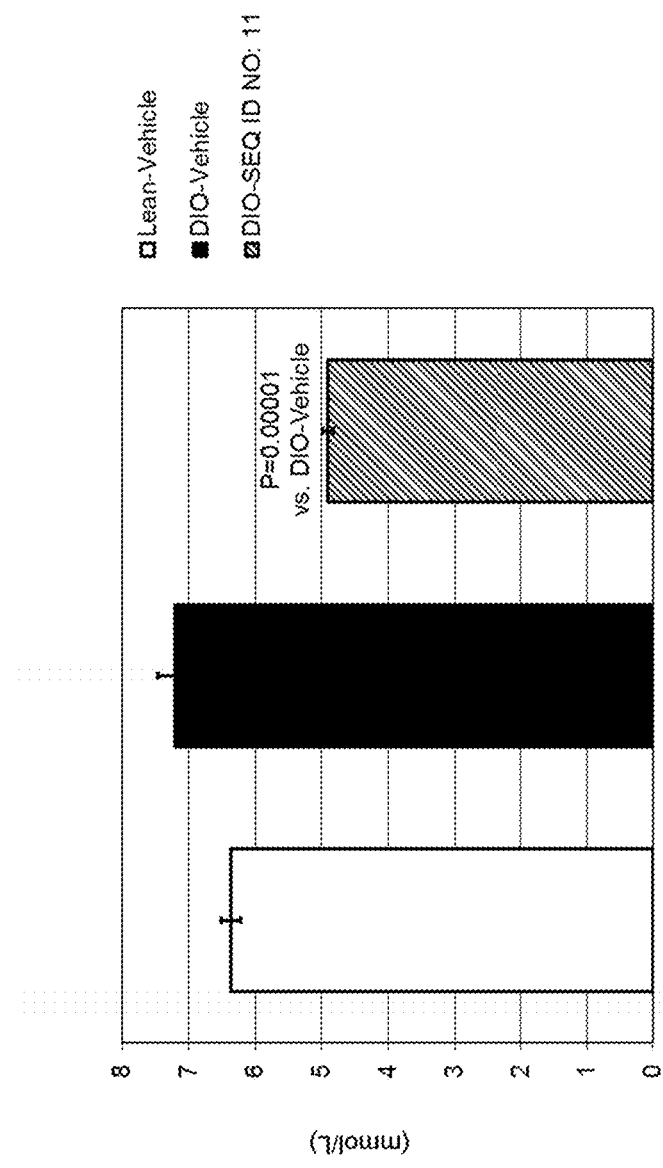

Four hours after the last dose on day 28 day of the dosing phase compared to DIO animals treated with vehicle chronic treatment of DIO animals with 30 µg/kg SEQ ID NO: 11 resulted in a statistically significant reduction in non-fasting plasma triglyceride (T-Test, Two-Tailed P<0.05, FIG. 16, Table 11), LDL (T-Test, Two-Tailed P<0.0001, FIG. 17, Table 11), insulin (T-Test, Two-Tailed P=0.001, FIG. 18, Table 11) and glucose concentrations (T-Test, Two-Tailed P<0.00001, FIG. 19, Table 11).

6) Statistical Analyses

In the Figures data are depicted as means±SEM. Statistical analyses were performed with Sigmaplot 12.5. Two-tailed T-Tests were used to compare groups of DIO-vehicle mice (n=8) with DIO-compound treated mice (n=8). When the difference in the mean values of the two groups was greater than 0.05 they were considered statistically significantly different. Lean-Vehicle group data are depicted in the Figures but served as a reference dataset for the non-obese state.

TABLE 11

Effects resulting from a single dose with SEQ ID NO: 11 in fed, female diet-induced obese (DIO) C57BL/6 mice.

| | Example | |
|---|---|---|
| | DIO-Vehicle | DIO-SEQ ID NO: 11 Dose |
| | twice-daily PBS | twice-daily 30 µg/kg |
| Body mass change (g) | +4.49 ± 0.40 | −7.74 ± 0.56 P < 0.00001 |
| Whole body fat mass change (g) | +3.03 ± 0.28 | −6.84 ± 0.46 P < 0.00001 |
| Terminal liver mass (g) | +2.39 ± 0.21 | +1.07 ± 0.04 P < 0.0001 |
| Terminal plasma triglyceride (mmol/L) | +0.70 ± 0.15 | +0.34 ± 0.06 P < 0.05 |
| Terminal plasma LDL (mmol/L) | +1.58 ± 0.12 | +0.84 ± 0.05 P < 0.0001 |
| Terminal plasma insulin (µg/L) | +129.35 ± 21.81 | +39.59 ± 4.74 P = 0.001 |
| Terminal plasma glucose (mmol/L) | +7.21 ± 0.26 | +4.91 ± 0.08 P = 0.00001 |

Data are means ± SEM.
n = 8/group.

Example 12

Acute and Chronic Effects of SEQ ID NO: 6, SEQ ID NO: 8, SEQ ID NO: 9 After Subcutaneous Treatment on Blood Glucose in Fed, Female Diabetic db/db Mice Animals, Study Design (Predosing Phase, Dosing Phase), Pharmacological Intervention:

Female healthy, lean BKS.Cg-(lean)/OlaHsd and diabetes-prone, obese BKS.Cg-+Lepr$^{db}$/+Lepr$^{db}$/OlaHsd mice were ordered group housed from Envigo RMS Inc., shipped group housed and remained group housed in disposable shoebox caging with wood chip bedding until day 15 of the predose phase. At the study start mice were approximately 12 weeks old.

Mice were housed under vivarium conditions including a 12 h light/dark cycle (light phase 04:00 AM-4:00 PM), room temperatures between 23-26° C. and a relative humidity between 30-70%. All animals had free access to water and Purina Fomulab Diet 5008.

On predose day 9 blood glucose and body mass (approximately between 08:00-10:00 AM) as well as HbA1c measurements were performed. On day 15 of the predose phase animals were assigned to treatment groups (n=8) and to new cages to match mean HbA1c and body masses between all db/db groups. An age-matched lean group was included in the study as a healthy, lean reference.

Prior to day 1 of the dosing phase, the test article was diluted with Phosphate Buffered Saline (PBS, Gibco, without CaCl$_2$ and MgCl$_2$) to a concentration of 1 mg/mL and aliquots of this stock solution were stored at approximately ≤−60° C. On day 1 of the dosing phase the stock aliquot was thawed and the injected test article solution was prepared fresh by diluting it with PBS to achieve the desired concentration.

On Day 1 of the dosing phase db/db mice were either treated once with a s.c. injection of PBS-vehicle or 30 μg/kg test article. The lean reference group was treated once with a s.c. injection of PBS-vehicle. The dosing was initiated and completed between 08:00 and 10:00 AM. The applied volume was 5 ml/kg and the dose was adjusted to the most recent body mass recording of each individual.

3) Blood Glucose Profile in Morning-Fed Animals

Animals had unlimited access to water and feed during the experiment. On day 1 of the dosing phase approximately 5 μL of blood were collected via tail clips at minute −30 and 0 prior to any other inlife activities. At minute 0 mice received a s.c. dose of either PBS-vehicle or 30 μg/kg SEQ ID NO: 6, SEQ ID NO: 8, or SEQ ID NO: 9. Further blood samples were harvested at hour 0.25, 0.5, 1, 1.5, 2, 3, 4, 6, 8, and 24 post-dose. Glucose measurements were performed in whole blood using AlphaTRAK glucometers. If the glucose concentrations of two measurements differed by more than 20 mg/dL a third value was recorded. The Area Under the Curve (AUC) for blood glucose was calculated via the trapezoid method and for the duration of the 24 post-dose hours.

Figure 20:
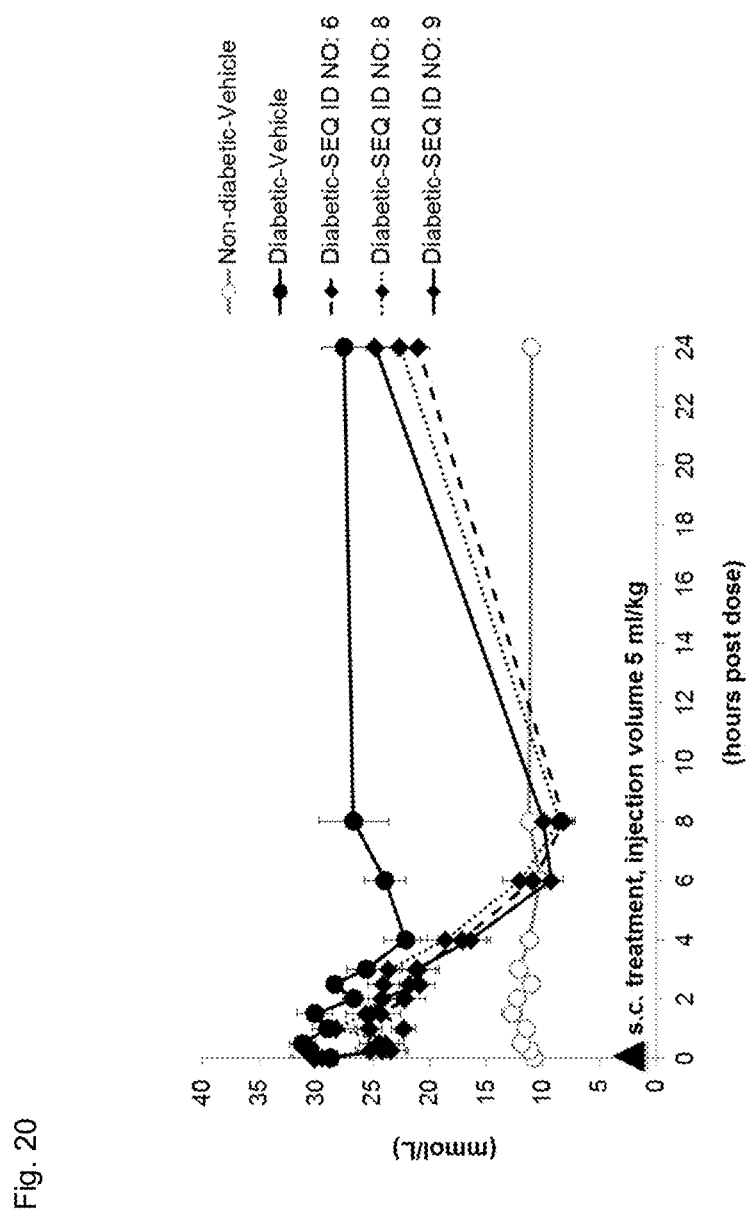
Figure 21:
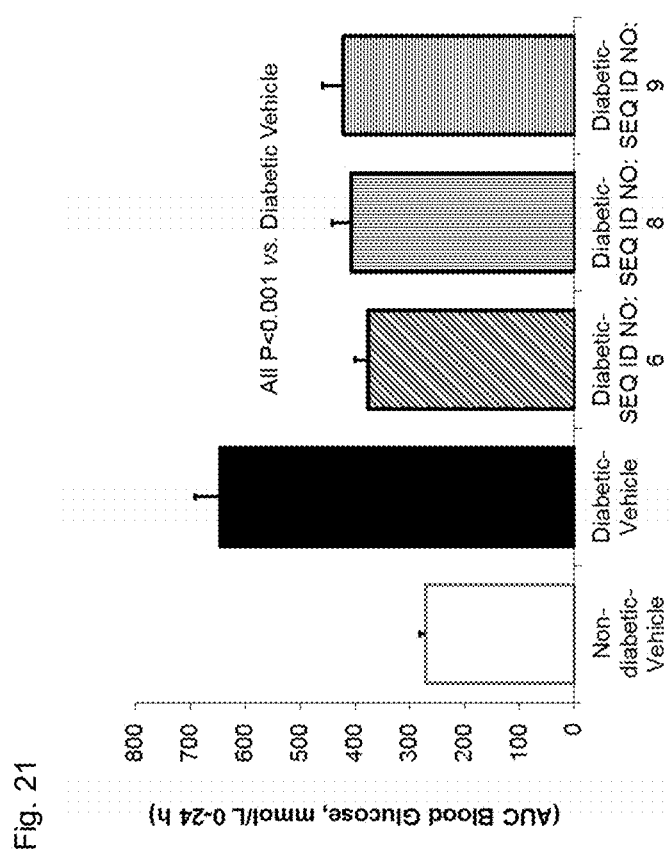

Single treatment of diabetic, non-fasting db/db mice with 30 μg/kg SEQ ID NO: 6, SEQ ID NO: 8, or SEQ ID NO: 9 within 6 hours normalised hyperglycemia to the non-fasting blood glucose concentrations observed in non-obese, lean reference mice. Twenty four hours post-dose mean blood glucose concentrations of all treated animals were at or close to baseline (FIG. 20). Single treatment of diabetic db/db mice with 30 μg/kg SEQ ID NO: 6, SEQ ID NO: 8, or SEQ ID NO: 9 resulted in a statistically significant reduction in the blood glucose AUC compared to the Diabetic-Vehicle group (One-Way ANOVA, Dunnet's Method, P<0.001 all treatment groups versus Diabetic-Vehicle group, FIG. 21, Table 12).

4) Statistical Analyses

In the Figures data are depicted as means±SEM. Statistical analyses were performed with Sigmaplot 12.5. A One Way Analysis of Variance and multiple comparisons (Dunnett's Method) were performed comparing the group of diabetic, obese db/db vehicle mice (n=8) with each diabetic, obese db/db compound treated mice (n=8). When the difference in the mean values of the two groups was greater than 0.05 they were considered statistically significantly different. Non-diabetic, lean-vehicle group data are depicted in the Figures serving as a reference dataset for the non-obese, non-diabetic state.

TABLE 12

Effects resulting from 28 days subcutaneous treatment with SEQ ID NO: 6, SEQ ID NO: 8, SEQ ID NO: 9 in fed, female diabetic db/db mice.

| | Example | | | |
|---|---|---|---|---|
| | db/db-Vehicle | db/db-SEQ ID NO: 6 | db/db-SEQ ID NO: 8 | db/db-SEQ ID NO: 9 |
| | | Dose | | |
| | PBS | once 30 μg/kg | once 30 μg/kg | once 30 μg/kg |
| Blood Glucose AUC (mmol/L for 24 hours) | 646.38 ± 45.04 | 376.58 ± 23.20 P < 0.001 | 406.72 ± 34.41 P < 0.001 | 422.08 ± 37.43 P < 0.001 |

Data are means ± SEM.
n = 8/group.

Example 13

Acute Effects of SEQ ID NO: 7 After Subcutaneous Treatment on Blood Glucose in Fed, Female Diabetic db/db Mice Animals, Study Design (Predosing Phase, Dosing Phase), Pharmacological Intervention:

Female healthy, lean BKS.Cg-(lean)/OlaHsd and diabetes-prone, obese BKS.Cg-+Lepr$^{db}$/+Lepr$^{db}$/OlaHsd mice were ordered group housed from Envigo RMS Inc., shipped group housed and remained group housed in disposable shoebox caging with wood chip bedding until day 15 of the predose phase. At the study start mice were approximately 12 weeks old.

Mice were housed under vivarium conditions including a 12 h light/dark cycle (light phase 04:00 AM-4:00 PM), room temperatures between 23-26° C. and a relative humidity between 30-70%. All animals had free access to water and Purina Fomulab Diet 5008.

On predose day 9 blood glucose and body mass (approximately between 08:00-10:00 AM) as well as HbA1c measurements were performed. On day 15 of the predose phase animals were assigned to treatment groups (n=8) and to new cages to match mean HbA1c and body masses between all db/db groups. An age-matched lean group was included in the study as a healthy, lean reference.

Prior to day 1 of the dosing phase, the test article was diluted with Phosphate Buffered Saline (PBS, Gibco, without CaCl$_2$ and MgCl$_2$) to a concentration of 1 mg/mL and aliquots of this stock solution were stored at approximately ≤−60° C. On day 1 of the dosing phase the stock aliquot was thawed and the injected test article solution was prepared fresh by diluting it with PBS to achieve the desired concentration.

On Day 1 of the dosing phase db/db mice were either treated once with a s.c. injection of PBS-vehicle or 30 µg/kg test article. The lean reference group was treated once with a s.c. injection of PBS-vehicle. The dosing was initiated and completed between 08:00 and 10:00 AM. The applied volume was 5 ml/kg and the dose was adjusted to the most recent body mass recording of each individual.

5) Blood Glucose Profile in Morning-Fed Animals

Animals had unlimited access to water and feed during the experiment. On day 1 of the dosing phase approximately 5 µL of blood were collected via tail clips at minute −30 and 0 prior to any other inlife activities. At minute 0 mice received a s.c. dose of either PBS-vehicle or 30 µg/kg SEQ ID NO: 7. Further blood samples were harvested at hour 0.25, 0.5, 1, 1.5, 2, 3, 4, 6, 8, and 24 post-dose. Glucose measurements were performed in whole blood using Alpha-TRAK glucometers. If the glucose concentrations of two measurements differed by more than 20 mg/dL a third value was recorded. The Area Under the Curve (AUC) for blood glucose was calculated via the trapezoid method and for the duration of the 24 post-dose hours.

Figure 22:
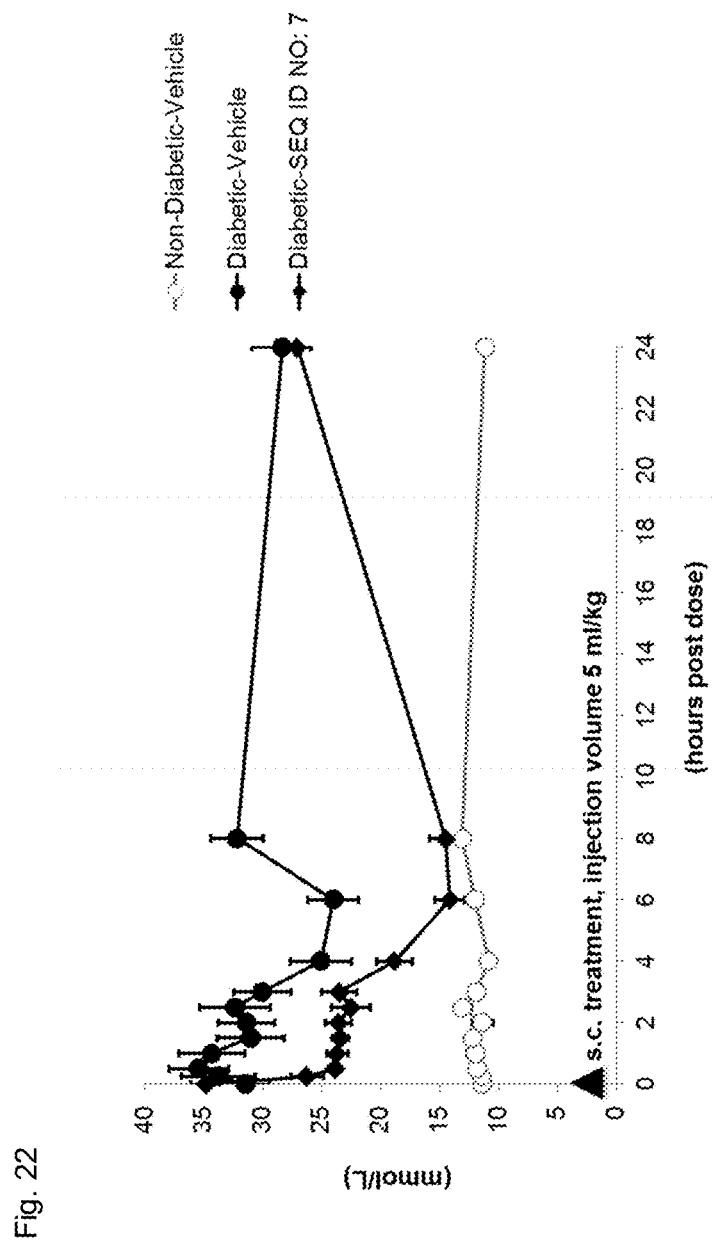
Figure 23:
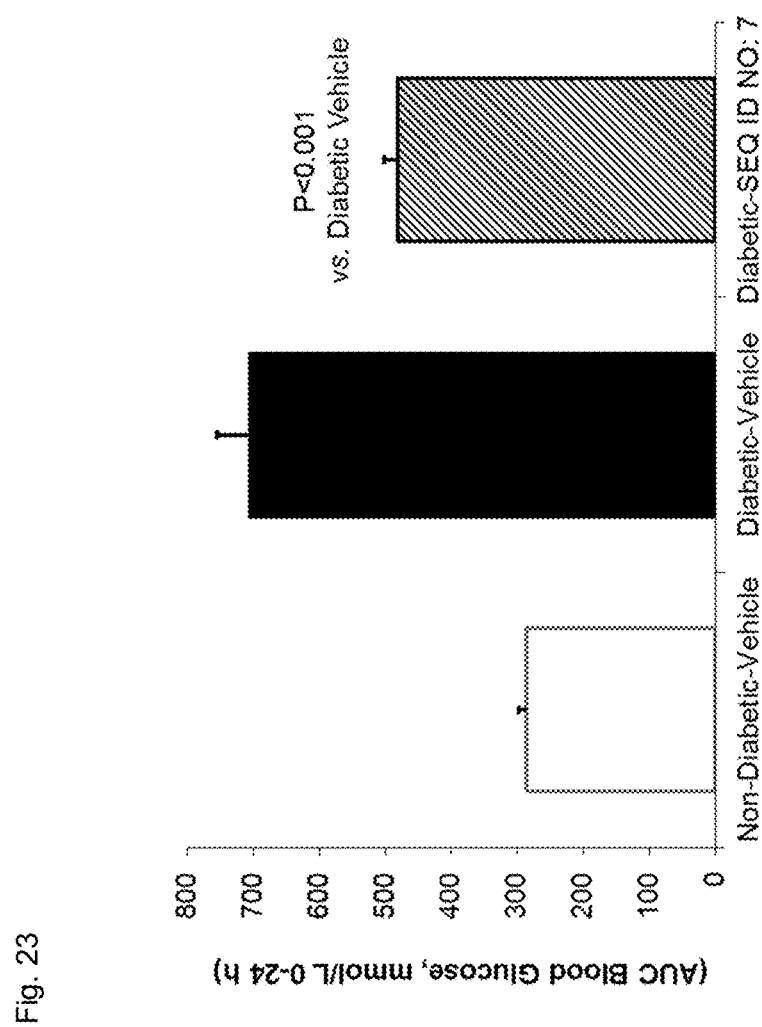

Single treatment of diabetic, non-fasting db/db mice with 30 µg/kg SEQ ID NO: 7 within 6 hours normalised hyperglycemia to the non-fasting blood glucose concentrations observed in non-obese, lean reference mice. Twentyfour hours post-dose the mean blood glucose concentration of SEQ ID NO: 7 treated animals was at baseline (FIG. 22). Single treatment of diabetic db/db mice with 30 µg/kg SEQ ID NO: 7 resulted in a statistically significant reduction in the blood glucose AUC compared to the Diabetic-Vehicle group (One-Way ANOVA, Dunnet's Method, P<0.001 SEQ ID NO: 7 versus Diabetic-Vehicle group, FIG. 23, Table 13).

6) Statistical Analyses

In the Figures data are depicted as means±SEM. Statistical analyses were performed with Sigmaplot 12.5. A One Way Analysis of Variance and multiple comparisons (Dunnett's Method) were performed comparing the group of diabetic, obese db/db vehicle mice (n=8) with diabetic, obese db/db compound treated mice (n=8). When the difference in the mean values of the two groups was greater than 0.05 they were considered statistically significantly different. Non-diabetic, lean-vehicle group data are depicted in the Figures serving as a reference dataset for the non-obese, non-diabetic state.

TABLE 13

Effects resulting from 28 days subcutaneous treatment with SEQ ID NO: 7 in fed, female diabetic db/db mice.

| | Example | |
|---|---|---|
| | db/db-Vehicle | db/db-SEQ ID NO: 7 |
| | Dose | |
| | PBS | once 30 µg/kg |
| Blood Glucose AUC (mmol/L for 24 hours) | 705.52 ± 49.31 | 480.59 ± 21.92 P < 0.001 |

Data are means ± SEM.
n = 8/group.

Example 14

Acute Effects of SEQ ID NO: 11 After Subcutaneous Treatment on Blood Glucose in Fed, Female Diabetic db/db Mice Animals, Study Design (Predosing Phase, Dosing Phase), Pharmacological Intervention:

Female healthy, lean BKS.Cg-(lean)/OlaHsd and diabetes-prone, obese BKS.Cg-+Lepr$^{db}$/+Lepr$^{db}$/OlaHsd mice were ordered group housed from Envigo RMS Inc., shipped group housed and remained group housed in disposable shoebox caging with wood chip bedding until day 15 of the predose phase. At the study start mice were approximately 12 weeks old.

On day 15 of the predose phase animals were assigned to treatment groups (n=8) and to new cages to match mean HbA1c and body masses between all db/db groups. An age-matched lean group was included in the study as a healthy, lean reference.

Prior to day 1 of the dosing phase, the test article was diluted with Phosphate Buffered Saline (PBS, Gibco, without CaCl$_2$ and MgCl$_2$) to a concentration of 1 mg/mL and aliquots of this stock solution were stored at approximately ≤−60° C. On day 1 of the dosing phase the stock aliquot was thawed and the injected test article solution was prepared fresh by diluting it with PBS to achieve the desired concentration.

On Day 1 of the dosing phase db/db mice were either treated once with a s.c. injection of PBS-vehicle or 30 µg/kg test article. The lean reference group was treated once with a s.c. injection of PBS-vehicle. The dosing was initiated and completed between 08:00 and 10:00 AM. The applied volume was 5 ml/kg and the dose was adjusted to the most recent body mass recording of each individual.

Blood Glucose Profile in Morning-Fed Animals

Animals had unlimited access to water and feed during the experiment. On day 1 of the dosing phase approximately 5 µL of blood were collected via tail clips at minute −30 and 0 prior to any other inlife activities. At minute 0 mice received a s.c. dose of either PBS-vehicle or 30 µg/kg SEQ ID NO: 11. Further blood samples were harvested at hour 0.25, 0.5, 1, 1.5, 2, 3, 4, 6, 8, and 24 post-dose. Glucose measurements were performed in whole blood using Alpha-TRAK glucometers. If the glucose concentrations of two measurements differed by more than 20 mg/dL a third value was recorded. The Area Under the Curve (AUC) for blood glucose was calculated via the trapezoid method and for the duration of the 24 post-dose hours.

Figure 24:
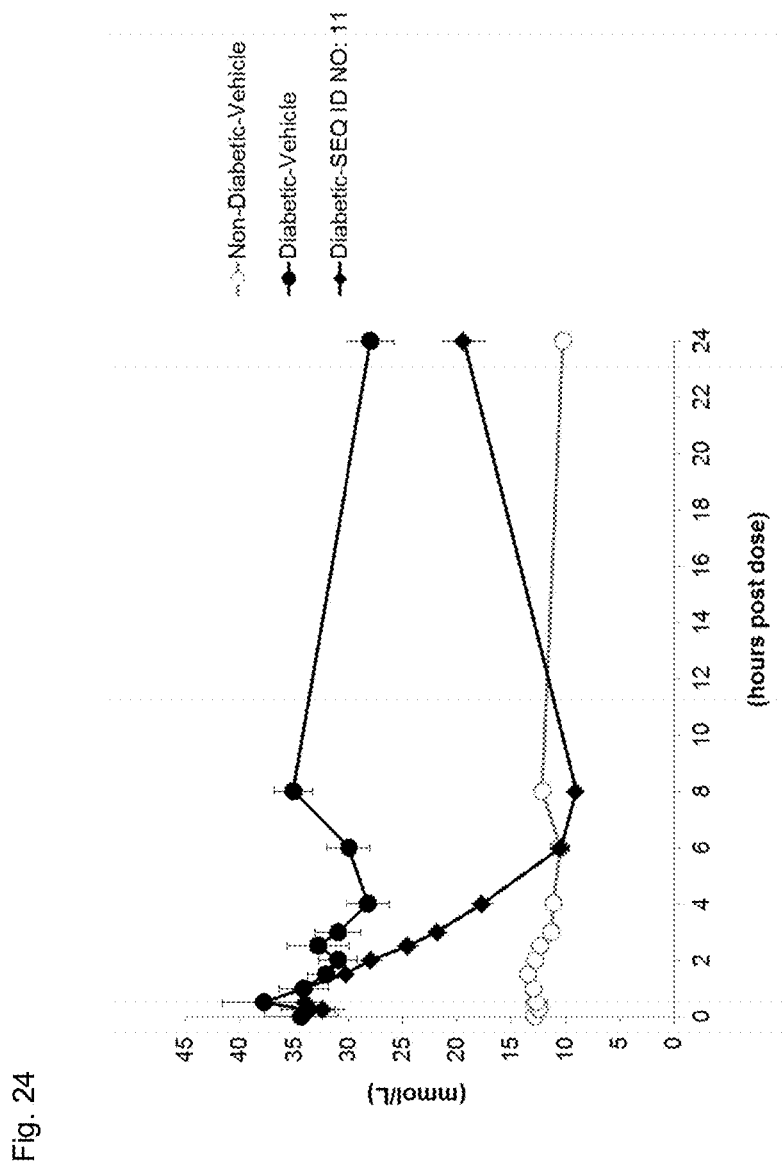

Single treatment of diabetic, non-fasting db/db mice with 30 μg/kg SEQ ID NO: 11 within 6 hours normalised hyperglycemia to the non-fasting blood glucose concentrations observed in non-obese, lean reference mice. Twenty-four hours post-dose mean blood glucose concentrations of SEQ ID NO: 11-treated animals were still below baseline concentrations (FIG. 24). Single treatment of diabetic db/db mice with 30 μg/kg SEQ ID NO: 11 resulted in a statistically significant reduction in the blood glucose AUC compared to the Diabetic-Vehicle group (One-Way ANOVA, Dunnet's Method, P<0.001 SEQ ID NO: 11 Versus Diabetic-Vehicle group, FIG. 25, Table 12).

Terminal Serum Triacylglycerol Concentrations in Morning-Fed Animals

Animals had unlimited access to water and feed during the experiment. At the terminal study endpoint animals were deeply anesthetized with isoflurane, an orbital blood sample was harvested, and serum prepared for triacylglycerol determination. Twenty-four hours post-dose, mean serum triacylglycerol concentrations of SEQ ID NO: 11-treated animals were statistically significantly below those displayed by animals of the Diabetic-Vehicle group (One-Way ANOVA, Dunnet's Method, P=0.007 SEQ ID NO: 11 versus Diabetic-Vehicle group, FIG. 26).

Statistical Analyses

In the Figures data are depicted as means±SEM. Statistical analyses were performed with Sigmaplot 12.5. A One Way Analysis of Variance and multiple comparisons (Dunnett's Method) were performed comparing the group of diabetic, obese db/db vehicle mice (n=8, except n=7 for the tracylglycerol analysis) with the group of diabetic, obese db/db compound treated mice (n=8). When the difference in the mean values of the two groups was greater than 0.05 they were considered statistically significantly different. Non-diabetic, lean-vehicle group data are depicted in the Figures serving as a reference dataset for the non-obese, non-diabetic state.

TABLE 14

Effects resulting from 28 days subcutaneous treatment with SEQ ID NO: 11 in fed, female diabetic db/db mice.

| | Example | |
|---|---|---|
| | db/db-Vehicle | db/db-SEQ ID NO: 11 |
| | Dose | |
| | PBS | once 30 μg/kg |
| Blood Glucose AUC (mmol/L for 24 hours) | 763.59 ± 39.53 | 391.06 ± 24.25<br>P < 0.001 |
| Terminal serum triacylglycerol concentration (mg/dL) | 192.13 ± 23.32 | 108.88 ± 9.89<br>P = 0.007 |

Data are means ± SEM.
n = 7-8/group.

Example 15

Acute Effects of SEQ ID NO: 10, SEQ ID NO: 12, SEQ ID NO: 13, SEQ ID NO: 16, SEQ ID NO: 26 After Subcutaneous Treatment on Blood Glucose in Fed, Female Diabetic db/db Mice Animals, Study Design (Predosing Phase, Dosing Phase), Pharmacological Intervention:

Female healthy, lean BKS.Cg-(lean)/OlaHsd and diabetes-prone, obese BKS.Cg-+Lepr$^{db}$/+Lepr$^{db}$/OlaHsd mice were ordered group housed from Envigo RMS Inc., shipped group housed and remained group housed in disposable shoebox caging with wood chip bedding until day 15 of the predose phase. At the study start mice were approximately 12 weeks old.

Mice were housed under vivarium conditions including a 12 h light/dark cycle (light phase 04:00 AM-4:00 PM), room temperatures between 23-26° C. and a relative humidity between 30-70%. All animals had free access to water and Purina Fomulab Diet 5008.

On predose day 9 blood glucose and body mass (approximately between 08:00-10:00 AM) as well as HbA1c measurements were performed. On day 15 of the predose phase animals were assigned to treatment groups (n=8) and to new cages to match mean HbA1c and body masses between all db/db groups. An age-matched lean group was included in the study as a healthy, lean reference.

Prior to day 1 of the dosing phase, the test article was diluted with Phosphate Buffered Saline (PBS, Gibco, without CaCl$_2$ and MgCl$_2$) to a concentration of 1 mg/mL and aliquots of this stock solution were stored at approximately ≤−60° C. On day 1 of the dosing phase the stock aliquot was thawed and the injected test article solution was prepared fresh by diluting it with PBS to achieve the desired concentration.

On Day 1 of the dosing phase db/db mice were either treated once with a s.c. injection of PBS-vehicle or 30 μg/kg test article. The lean reference group was treated once with a s.c. injection of PBS-vehicle. The dosing was initiated and completed between 08:00 and 10:00 AM. The applied volume was 5 ml/kg and the dose was adjusted to the most recent body mass recording of each individual.

1) Blood Glucose Profile in Morning-Fed Animals

Animals had unlimited access to water and feed during the experiment. On day 1 of the dosing phase approximately 5 μL of blood were collected via tail clips at minute −30 and 0 prior to any other inlife activities. At minute 0 mice received a s.c. dose of either PBS-vehicle or 30 μg/kg SEQ ID NO: 10, SEQ ID NO: 12, SEQ ID NO: 13, SEQ ID NO: 16, or SEQ ID NO: 26. Further blood samples were harvested at hour 0.25, 0.5, 1, 1.5, 2, 3, 4, 6, 8, and 24 post-dose. Glucose measurements were performed in whole blood using AlphaTRAK glucometers. If the glucose concentrations of two measurements differed by more than 20 mg/dL a third value was recorded. The Area Under the Curve (AUC) for blood glucose was calculated via the trapezoid method and for the duration of the 24 post-dose hours.

Figure 27:
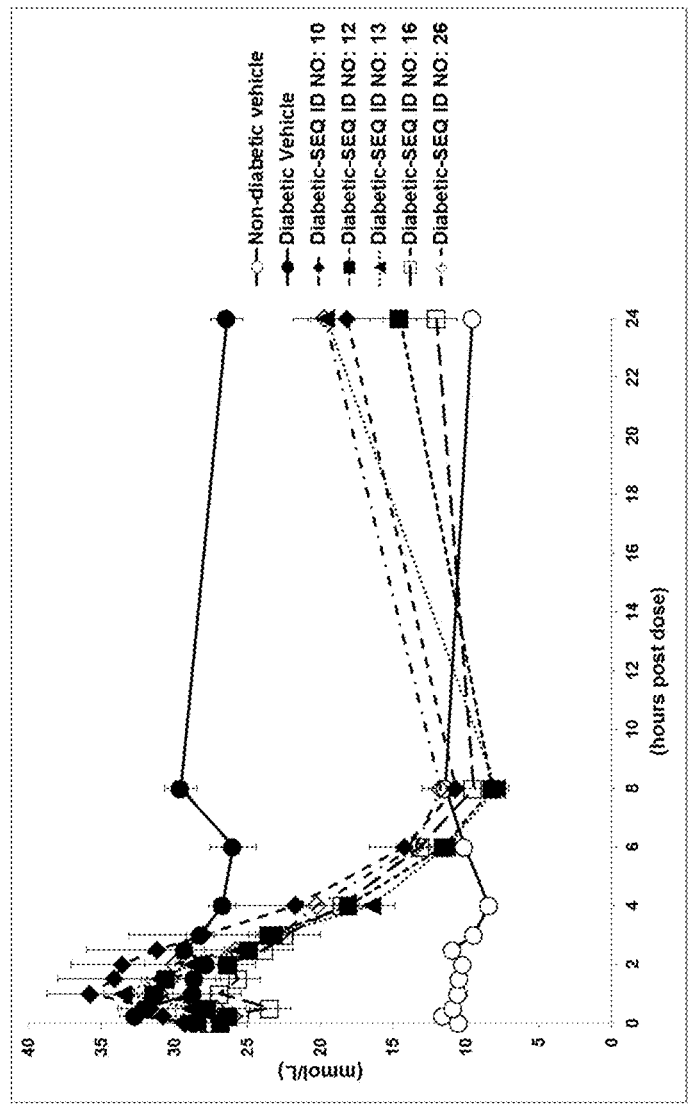
Figure 28:
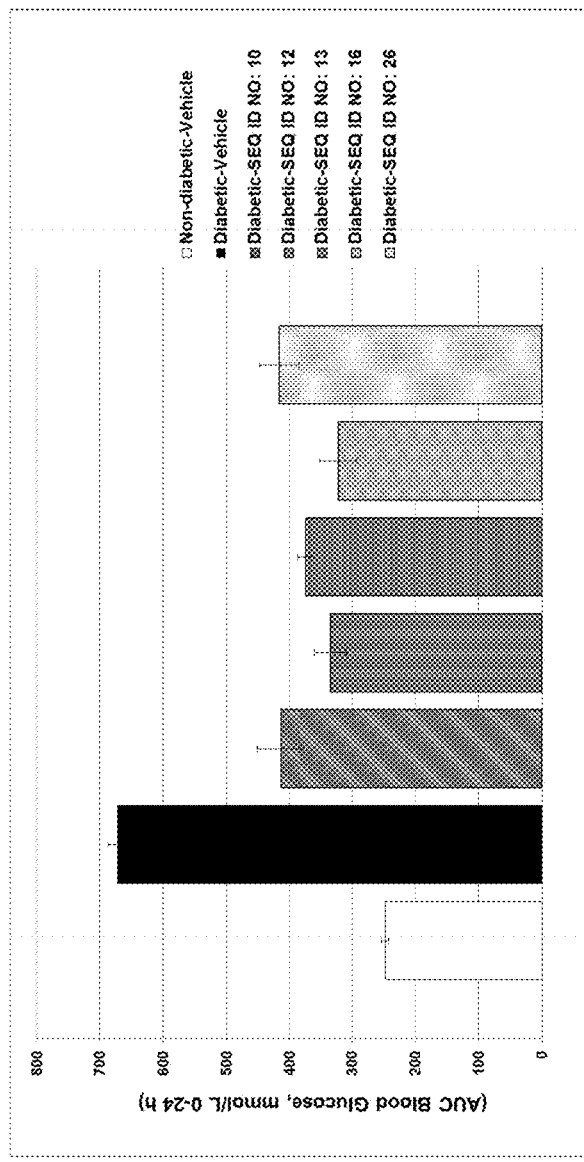

Single treatment of diabetic, non-fasting db/db mice with 30 μg/kg SEQ ID NO: 10, SEQ ID NO: 12, SEQ ID NO: 13, SEQ ID NO: 16, or SEQ ID NO: 26 within 6 hours normalised hyperglycemia to the non-fasting blood glucose concentrations observed in non-obese, lean reference mice. Twentyfour hours post-dose mean blood glucose concentrations of all treated animals were at or close to baseline (FIG. 27). Single treatment of diabetic db/db mice with 30 μg/kg SEQ ID NO: 10, SEQ ID NO: 12, SEQ ID NO: 13, SEQ ID NO: 16, or SEQ ID NO: 26 resulted in a statistically significant reduction in the blood glucose AUC compared to the Diabetic-Vehicle group (One-Way ANOVA, Dunnet's Method, P<0.001 all treatment groups versus Diabetic-Vehicle group, FIG. 28, Table 15).

2) Statistical Analyses

In the Figures data are depicted as means±SEM. Statistical analyses were performed with Everst@t 6.0.12. A One Way Analysis of Variance and multiple comparisons (Dunnett's Method) were performed comparing the group of diabetic, obese db/db vehicle mice (n=8) with each diabetic, obese db/db compound treated mice (n=8). When the difference in the mean values of the two groups was greater than 0.05 they were considered statistically significantly different. Non-diabetic, lean-vehicle group data are depicted in the Figures serving as a reference dataset for the non-obese, non-diabetic state.

TABLE 15

Effects resulting from subcutaneous treatment with SEQ ID NO: 10, SEQ ID NO: 12, SEQ ID NO: 13, SEQ ID NO: 16, or SEQ ID NO: 26 in fed, female diabetic db/db mice.

| Example Dose | Blood Glucose AUC (mmol/L for 24 hours) |
|---|---|
| db/db-Vehicle PBS | 671.39 ± 15.42 |
| db/db-SEQ ID NO: 10 once 30 µg/kg | 413.77 ± 37.33 P < 0.001 |
| db/db-SEQ ID NO: 12 once 30 µg/kg | 334.37 ± 25.07 P < 0.001 |
| db/db-SEQ ID NO: 13 once 30 µg/kg | 373.42 ± 13.99 P < 0.001 |
| db/db-SEQ ID NO: 16 once 30 µg/kg | 321.96 ± 29.27 P < 0.001 |
| db/db-SEQ ID NO: 26 once 30 µg/kg | 416.25 ± 30.62 P < 0.001 |

Data are means ± SEM.
n = 8/group.

Example 16

Anti-Atherosclerotic Activity of the Trigonal GLP-1R/GCGR/GIPR Agonists in ApoE KO Mice The apolipoprotein E (ApoE) knockout (KO) mouse model is widely used to investigate atherosclerosis. These mice spontaneously develop atherosclerotic lesions that are morphologically similar to those observed in humans (Meir & Leitersdorf 2004, Arterioscler Thromb Vasc Biol 24: 1006-1014, Rosenfeld et al. 2000, Arterioscler Thromb Vasc Biol 20: 2587-2592).

Animals

Male ApoE KO mice (B.129P2-apoetm1Unc/J) were randomly allocated to control or treatment groups (N=15 per group); wild-type mice (C57BL6/J) received vehicle treatment and acted as a second, healthy control.

Study Procedure

ApoE KO and wild-type mice received constant 16 weeks infusion using subcutaneous osmotic minipumps (ALZET™) filled with either vehicle (sterile acetate buffer, pH 4.5), Peptides SEQ ID NO. 6 & SEQ ID NO. 11 (150 µg/kg/day) or with Liraglutide (600 µg/kg/day). Body weight and food intake was monitored throughout the study on a weekly basis.

Blood Lipid Parameters

Blood samples for blood lipid analysis were drawn before treatment and at weeks 7 and 16 to analyze total cholesterol, low density lipoprotein (LDL) cholesterol and high density lipoprotein (HDL) cholesterol (not shown).

Quantification of Atherosclerotic Plaque Formation

The aorta was dissected and aortic atherosclerotic plaque formation was measured as absolute and relative plaque area (% oilred stained area of total aortic surface area) using quantitative and automated image analysis.

Figure 29:
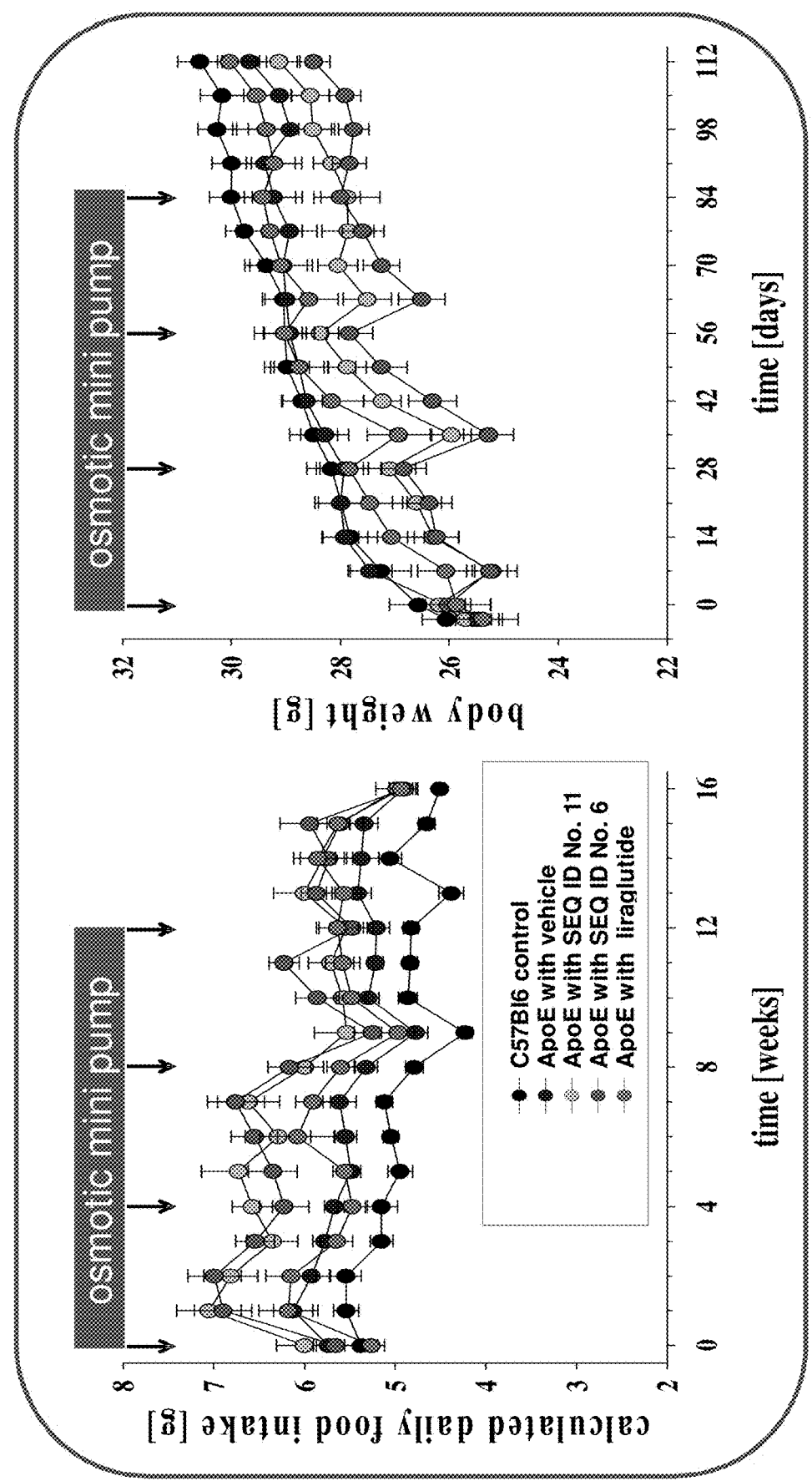

The results are shown in the figures:

FIG. 29: Food intake and body weight monitoring data

FIG. 30: Aortic plaque area data

FIG. 31: Serum total cholesterol and LDL-cholesterol data

In male ApoE KO mice chronic 4 months treatment with the peptides SEQ ID NO. 6 & SEQ ID NO. 11 at a dose of 150 µg/kg/day led to a significant reduction of atherosclerotic plaques by 63% and 73% relative to vehicle control. Anti-atherosclerotic efficacy was accompanied by a marked reduction in LDL-cholesterol.

In contrast, a 4-fold higher dose of the pure GLP-1 receptor agonist liraglutide reduced aortic plaques formation significantly but only by 37% with LDL-cholesterol lowering being far less pronounced.

TABLE 8

Sequences

| SEQ. ID | Sequence |
|---|---|
| 1 | H-A-E-G-T-F-T-S-D-V-S-S-Y-L-E-G-Q-A-A-K-E-F-I-A-W-L-V-K-G-R-NH2 |
| 2 | H-A-E-G-T-F-T-S-D-V-S-S-Y-L-E-G-Q-A-A-K(gGlu-Palm)-E-F-I-A-W-L-V-R-G-R-G-OH |
| 3 | H-S-Q-G-T-F-T-S-D-Y-S-K-Y-L-D-S-R-R-A-Q-D-F-V-Q-W-L-M-N-T-OH |
| 4 | H-G-E-G-T-F-T-S-D-L-S-K-Q-M-E-E-E-A-V-R-L-F-I-E-W-L-K-N-G-G-P-S-S-G-A-P-P-P-S-NH2 |
| 5 | Y-A-E-G-T-F-I-S-D-Y-S-1-A-M-D-K-1-H-Q-Q-D-F-V-N-W-L-L-A-Q-K-G-K-K-N-D-W-K-H-N-I-T-Q-OH |
| 6 | H-Aib-H-G-T-F-T-S-D-L-S-K-L-K[gGlu-gGlu-Palm]-E-E-Q-R-Q-K-E-F-I-E-W-L-K-A-G-G-H-P-S-Aib-K-P-P-P-K-NH2 |
| 7 | H-Aib-H-G-T-F-T-S-D-L-S-K-L-K[gGlu-gGlu-Palm]-E-E-Q-R-Q-K-E-F-I-E-W-L-K-A-dAla-G-H-P-S-Aib-K-P-P-P-K-NH2 |
| 8 | H-Aib-H-G-T-F-T-S-D-L-S-K-L-K[gGlu-gGlu-Palm]-E-E-Q-R-Q-K-E-F-I-E-W-L-K-A-G-G-P-P-S-Aib-K-P-P-P-K-NH2 |

TABLE 8-continued

Sequences

| SEQ. ID | Sequence |
|---|---|
| 9 | H-Aib-H-G-T-F-T-S-D-L-S-K-L-K[gGlu-gGlu-Palm]-E-E-Q-R-Q-K-E-F-I-E-W-L-K-A-dAla-G-P-P-S-Aib-K-P-P-P-K-NH2 |
| 10 | H-Aib-H-G-T-F-T-S-D-L-S-K-L-K[gGlu-gGlu-Palm]-E-E-Q-R-Q-Aib-E-F-I-E-W-L-K-A-G-G-P-P-S-Aib-K-P-P-P-K-NH2 |
| 11 | H-Aib-H-G-T-F-T-S-D-L-S-K-L-K[gGlu-gGlu-Palm]-E-E-Q-R-Q-Aib-E-F-I-E-W-L-K-A-dAla-G-P-P-S-Aib-K-P-P-P-K-NH2 |
| 12 | H-Aib-H-G-T-F-T-S-D-L-S-K-L-K[gGlu-gGlu-Palm]-E-E-Q-R-Q-Aib-E-F-I-E-W-L-K-A-G-G-H-P-S-Aib-K-P-P-P-K-NH2 |
| 13 | H-Aib-H-G-T-F-T-S-D-L-S-K-L-K[gGlu-gGlu-Palm]-E-E-Q-R-Q-Aib-E-F-I-E-W-L-K-A-dAla-G-H-P-S-Aib-K-P-P-P-K-NH2 |
| 14 | H-Aib-H-G-T-F-T-S-D-L-S-K-L-K[gGlu-gGlu-AEEA-Palm]-E-E-Q-R-Q-K-E-F-I-E-W-L-K-A-G-G-H-P-S-Aib-K-P-P-P-K-NH2 |
| 15 | H-Aib-H-G-T-F-T-S-D-L-S-K-L-K[gGlu-gGlu-AEEA-Palm]-E-E-Q-R-Q-K-E-F-1-E-W-L-K-A-dAla-G-H-P-S-Aib-K-P-P-P-K-NH2 |
| 16 | H-Aib-H-G-T-F-T-S-D-L-S-K-L-K[gGlu-Palm]-E-E-Q-R-Q-Aib-E-F-I-E-W-L-K-A-dAla-G-P-P-S-Aib-K-P-P-P-K-NH2 |
| 17 | H-Aib-H-G-T-F-T-S-D-L-S-K-L-K[gGlu-Stea]-E-E-Q-R-Q-Aib-E-F-I-E-W-L-K-A-dAla-G-P-P-S-Aib-K-P-P-P-K-NH2 |
| 18 | H-Aib-H-G-T-F-T-S-D-L-S-K-L-K[gGlu-Palm]-E-E-Q-R-Q-Aib-E-F-I-E-W-L-K-A-G-G-P-P-S-Aib-K-P-P-P-K-NH2 |
| 19 | H-Aib-H-G-T-F-T-S-D-L-S-K-L-K[gGlu-Stea]-E-E-Q-R-Q-Aib-E-F-I-E-W-L-K-A-G-G-P-P-S-Aib-K-P-P-P-K-NH2 |
| 20 | H-Aib-H-G-T-F-T-S-D-L-S-K-L-K[gGlu-Palm]-E-E-Q-R-Q-K-E-F-I-E-W-L-K-A-G-G-P-P-S-Aib-K-P-P-P-K-NH2 |
| 21 | H-Aib-H-G-T-F-T-S-D-L-S-K-L-K[gGlu-Stea]-E-E-Q-R-Q-K-E-F-I-E-W-L-K-A-G-G-P-P-S-Aib-K-P-P-P-K-NH2 |
| 22 | H-Aib-H-G-T-F-T-S-D-L-S-K-L-K[gGlu-AEEA-gAAA-Palm]-E-E-Q-R-Q-K-E-F-I-E-W-L-K-A-G-G-H-P-S-Aib-K-P-P-P-K-NH2 |
| 23 | H-Aib-H-G-T-F-T-S-D-L-S-K-L-K[gGlu-AEEA-gAAA-Palm]-E-E-Q-R-Q-K-E-F-I-E-W-L-K-A-dAla-G-H-P-S-Aib-K-P-P-P-K-NH2 |
| 24 | H-Aib-H-G-T-F-T-S-D-L-S-K-L-K[gGlu-gGlu-AEEA-Palm]-E-E-Q-R-Q-Aib-E-F-I-E-W-L-K-A-dAla-G-P-P-S-Aib-K-P-P-P-K-NH2 |
| 25 | H-Aib-H-G-T-F-T-S-D-L-S-K-L-K[gGlu-AEEA-gAAA-Palm]-E-E-Q-R-Q-Aib-E-F-I-E-W-L-K-A-dAla-G-P-P-S-Aib-K-P-P-P-K-NH2 |
| 26 | H-Aib-H-G-T-F-T-S-D-L-S-K-L-K[gGlu-gGlu-AEEA-Palm]-E-E-Q-R-Q-Aib-E-F-I-E-W-L-K-A-G-G-P-P-S-Aib-K-P-P-P-K-NH2 |
| 27 | H-Aib-H-G-T-F-T-S-D-L-S-K-L-K[gGlu-AEEA-gAAA-Palm]-E-E-Q-R-Q-Aib-E-F-I-E-W-L-K-A-G-G-P-P-S-Aib-K-P-P-P-K-NH2 |
| 28 | H-Aib-Q-G-T-F-T-S-D-L-S-K-Q-K[gGlu-Stea]-D-E-Q-R-A-K-E-F-I-E-W-L-K-A-G-G-P-S-S-G-A-P-P-P-S-NH2 |
| 29 | Y-Aib-Q-G-T-F-T-S-D-L-S-K-Q-K[gGlu-Stea]-D-E-Q-R-A-K-E-F-I-E-W-L-K-S-G-G-P-S-S-G-A-P-P-P-S-NH2 |

The invention claimed is:

1. A compound of the formula I:

H$_2$N-His-Aib-His-Gly-Thr-Phe-Thr-Ser-Asp-Leu-Ser-Lys-Leu-X14-Glu-Glu-Gln-Arg-X20-Glu-Phe-Ile-Glu-Trp-Leu-Lys-Ala-X29-Gly-X31-Pro-Ser-Aib-Lys-Pro-Pro-Pro-Lys-R$^1$   I wherein:

X14 is an amino acid residue with a functionalized —NH$_2$ side chain group, selected from the group consisting of Lys, Orn, Dab, and Dap, wherein the —NH$_2$ side chain group is functionalized by —Z—C(O)—R$^5$, wherein Z is a linker in all stereoisomeric forms and R$^5$ is a moiety comprising up to 50 carbon atoms and heteroatoms selected from N and O, X20 is an amino acid residue selected from Aib and Lys, X29 is an amino acid residue selected from D-Ala and Gly, X31 is an amino acid residue selected from His and Pro, R$^1$ is NH$_2$ or OH, or a salt or solvate thereof.

2. The compound of claim 1, wherein R$^1$ is NH$_2$, or a salt or solvate thereof.

3. The compound of claim 1, or the salt or solvate thereof, which has a relative activity of at least 5% compared to that of natural glucagon at the glucagon receptor.

4. The compound of claim 1, or the salt or solvate thereof, which exhibits a relative activity of at least 7% compared to that of GLP-1(7-36)-amide at the GLP-1 receptor.

5. The compound of claim 1, or the salt or solvate thereof, which exhibits a relative activity of at least 4% compared to that of GIP at the GIP receptor.

6. The compound of claim 1, wherein X14 is Lys, wherein the —NH$_2$ side chain group is functionalized with the group —Z—C(O)R$^5$, wherein:

Z is a group selected from gGlu, gGlu-gGlu, gGlu-AEEAc-gAAA-, gGlu-gGlu-AEEAc, AEEAc-AEEAc-gGlu and AEEAc-AEEAc-AEEAc; and R$^5$ is a group selected from pentadecanyl and heptadecanyl;

or a salt or solvate thereof.

7. The compound of claim 1, wherein X14 is Lys, wherein the —NH$_2$ side chain group is functionalized with a group —Z—C(O)R$^5$, wherein:

Z is a group selected from gGlu, gGlu-gGlu, gGlu-AEEAc-gAAA- and gGlu-gGlu-AEEAc; and R$^5$ is a group selected from pentadecanyl and heptadecanyl:

or a salt or solvate thereof.

8. The compound of claim 1, wherein:

X14 is Lys, wherein the —NH$_2$ side chain group is functionalized by (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (2-{2-[2-(2-{2-[(4 S)-4-Carboxy-4-hexadecanoylamino-butyrylamino]-ethoxy}-ethoxy)-acetylamino]-ethoxy}-ethoxy)-acetyl, (2-{2-[2-(2-{2-[(4 S)-4-Carboxy-4-octadecanoyl amino-butyrylamino]-ethoxy}-ethoxy)-acetylamino]-ethoxy}-ethoxy)-acetyl, and [2-(2-{2-[2-(2-{2-[2-(2-Octadecanoylamino-ethoxy)-ethoxy]-acetylamino}-ethoxy)-ethoxy]-acetylamino}-ethoxy)-ethoxy]-acetyl-; and R$^1$ is NH$_2$;

or a salt or solvate thereof.

9. The compound of claim 1, wherein:

X14 is Lys, wherein the —NH$_2$ side chain group is functionalized by a group selected from (S)-4-Carboxy-4-hexadecanoylamino-butyryl-, (S)-4-Carboxy-4-octadecanoylamino-butyryl-, (S)-4-Carboxy-4-((S)-4-carboxy-4-hexadecanoylamino-butyrylamino)-butyryl-, (2-{2-[2-(2-{2-[(4S)-4-Carboxy-4-hexadecanoylamino-butyrylamino]-ethoxy}-ethoxy)-acetylamino]-ethoxy}-ethoxy)-acetyl, and (2-{2-[2-(2-{2-[(4S)-4-Carboxy-4-octadecanoylamino-butyrylamino]-ethoxy}-ethoxy)-acetylamino]-ethoxy}-ethoxy)-acetyl; and R$^1$ is NH$_2$;

or a salt or solvate thereof.

10. The compound of claim 1, wherein:
X14 is Lys, wherein the —NH$_2$ side chain group is functionalized by (S)-4-Carboxy-4-((S)-4-carboxy-4-hexadecanoylamino-butyrylamino)-butyryl-;
X20 is selected from Lys and Aib;
X29 is an amino acid residue selected from D-Ala and Gly;
X31 is an amino acid residue selected from His and Pro; and
R$^1$ is NH$_2$;
or a salt or solvate thereof.

11. The compound of claim 1, wherein:
X14 is Lys, wherein the —NH$_2$ side chain group is functionalized by a group selected from (S)-4-Carboxy-4-((S)-4-carboxy-4-hexadecanoylamino-butyrylamino)-butyryl- and (S)-4-Carboxy-4-octadecanoylamino-butyryl-;
X20 is Lys;
X29 is an amino acid residue selected from D-Ala and Gly;
X31 is an amino acid residue selected from His and Pro; and
R$^1$ is NH$_2$;
or a salt or solvate thereof.

12. The compound of claim 1, wherein:
X14 is Lys, wherein the —NH$_2$ side chain group is functionalized by a group selected from (S)-4-Carboxy-4-((S)-4-carboxy-4-hexadecanoylamino-butyrylamino)-butyryl- and (S)-4-Carboxy-4-octadecanoylamino-butyryl-;
X20 is Lys;
X29 is an amino acid residue selected from D-Ala and Gly;
X31 is His; and
R$^1$ is NH$_2$;
or a salt or solvate thereof.

13. The compound of claim 1, wherein:
X14 is Lys, wherein the —NH$_2$ side chain group is functionalized by a group selected from (S)-4-Carboxy-4-((S)-4-carboxy-4-hexadecanoylamino-butyrylamino)-butyryl- and (S)-4-Carboxy-4-octadecanoylamino-butyryl-;
X20 is Lys;
X29 is Gly;
X31 is an amino acid residue selected from His and Pro; and
R$^1$ is NH$_2$;
or a salt or solvate thereof.

14. The compound of claim 1, wherein:
X14 is Lys, wherein the —NH$_2$ side chain group is functionalized by a group selected from (S)-4-Carboxy-4-((S)-4-carboxy-4-hexadecanoylamino-butyrylamino)-butyryl- and (S)-4-Carboxy-4-octadecanoylamino-butyryl-;
X20 is Aib;
X29 is an amino acid residue selected from D-Ala and Gly;
X31 is an amino acid residue selected from His and Pro; and
R$^1$ is NH$_2$;
or a salt or solvate thereof.

15. The compound of claim 1, wherein:
X14 is Lys, wherein the —NH$_2$ side chain group is functionalized by a group selected from (S)-4-Carboxy-4-((S)-4-carboxy-4-hexadecanoylamino-butyrylamino)-butyryl- and (S)-4-Carboxy-4-octadecanoylamino-butyryl-;
X20 is Aib;
X29 is an amino acid residue selected from D-Ala and Gly;
X31 is Pro; and
R$^1$ is NH$_2$;
or a salt or solvate thereof.

16. The compound of claim 1, wherein:
X14 is Lys, wherein the —NH$_2$ side chain group is functionalized by (S)-4-Carboxy-4-((S)-4-carboxy-4-hexadecanoylamino-butyrylamino)-butyryl-;
X20 is Aib;
X29 is D-Ala;
X31 is an amino acid residue selected from His and Pro; and
R$^1$ is NH$_2$;
or a salt or solvate thereof.

17. The compound of claim 1, selected from the compounds of SEQ ID NOs: 6-27, or salts or solvates thereof.

18. The compound of claim 1, wherein the compound is the compound of SEQ ID NO: 6, or a salt or solvate thereof.

19. The compound of claim 1, wherein the compound is the compound of SEQ ID NO: 9, or a salt or solvate thereof.

20. The compound of claim 1, wherein the compound is the compound of SEQ ID NO: 11, or a salt or solvate thereof.

21. A pharmaceutical composition comprising the compound of claim 1, or a salt or solvate thereof.

22. A pharmaceutical composition comprising the compound of claim 1, or a pharmaceutically acceptable salt or solvate thereof, which is present as an active agent together with at least one pharmaceutically acceptable carrier.

23. The pharmaceutical composition of claim 21, further comprising at least one additional therapeutically active agent.

24. The pharmaceutical composition of claim 23, wherein the at least one additional therapeutically active agent is selected from the group consisting of:
insulin and insulin derivatives; GLP-1, GLP-1 analogues and GLP-1 receptor agonists;
DPP-4 inhibitors; SGLT2 inhibitors; dual SGLT2/SGLT1 inhibitors;
biguanides, thiazolidinediones, dual PPAR agonists, sulfonylureas, meglitinides, alpha-glucosidase inhibitors, amylin and amylin analogues; GPR119 agonists, GPR40 agonists, GPR120 agonists, GPR142 agonists, systemic or low-absorbable TGR5 agonists;
bromocriptine mesylate, inhibitors of 11-beta-HSD, activators of glucokinase, inhibitors of DGAT, inhibitors of protein tyrosine-phosphatase 1, inhibitors of glucose-6-phosphatase, inhibitors of fructose-1,6-bisphosphatase, inhibitors of glycogen phosphorylase, inhibitors of phosphoenol pyruvate carboxykinase, inhibitors of glycogen synthase kinase, inhibitors of pyruvate dehydrokinase, alpha 2-antagonists, CCR-2 antagonists, SGLT-1 inhibitors, modulators of glucose transporter-4, somatostatin receptor 3 agonists;
lipid lowering agents; active substances for the treatment of obesity; gastrointestinal peptides; lipase inhibitors, angiogenesis inhibitors, H3 antagonists, AgRP inhibitors, triple monoamine uptake inhibitors, MetAP2 inhibitors, nasal formulation of the calcium channel blocker diltiazem, antisense molecules against production of fibroblast growth factor receptor 4, prohibitin targeting peptide-1; and drugs for influencing high blood pressure, chronic heart failure or atherosclerosis.

25. A method for the treatment of a disease or disorder in a patient, the method comprising administering to the patient an effective amount of the compound of claim 1, or a salt or solvate thereof, wherein the disease or disorder is glucose intolerance, insulin resistance, pre-diabetes, increased fasting glucose, hyperglycemia, type 2 diabetes, hypertension, dyslipidemia, arteriosclerosis, coronary heart disease, peripheral artery disease, stroke, or any combination of these individual disease components.

26. The method of claim 25, wherein the disease or disorder is control of appetite, feeding and calorie intake, increase of energy expenditure, prevention of weight gain, promotion of weight loss, reduction of excess body weight, obesity, or morbid obesity.

27. The method of claim 25, wherein the disease or disorder is hepatosteatosis.

28. The method of claim 25, wherein the disease or disorder is selected from hyperglycemia, type 2 diabetes, obesity, and combinations thereof.

29. The method of claim 25, wherein the disease or disorder is both type 2 diabetes and obesity.

30. The method of claim 25, wherein the disease or disorder is diabetes.

31. The method of claim 25, wherein the disease or disorder is obesity.

32. The method of claim 25, wherein the disease or disorder is atherosclerosis.

33. A method for reducing the intestinal passage, increasing the gastric content and/or reducing the food intake of a patient, the method comprising administering to the patient an effective amount of the compound of claim 1, or a salt or solvate thereof.

34. A method for reducing blood glucose levels and/or reducing HbA1c levels of a patient, the method comprising administering to the patient an effective amount of the compound of claim 1, or a salt or solvate thereof.

35. A method for reducing body weight of a patient, the method comprising administering to the patient an effective amount of the compound of claim 1, or a salt or solvate thereof.

36. A method for the treatment of a disease or disorder in a patient, the method comprising administering to the patient the pharmaceutical composition of claim 23, wherein the compound, or the salt or solvate thereof, and the additional active ingredient are administered to the patient simultaneously, wherein the disease or disorder is glucose intolerance, insulin resistance, pre-diabetes, increased fasting glucose, hyperglycemia, type 2 diabetes, hypertension, dyslipidemia, arteriosclerosis, coronary heart disease, peripheral artery disease, stroke, or any combination of these individual disease components.

37. A method for the treatment of a disease or disorder in a patient, the method comprising administering to the patient the pharmaceutical composition of claim 23, wherein the compound, or the salt or solvate thereof, and the additional active ingredient are administered to the patient sequentially, wherein the disease or disorder is glucose intolerance, insulin resistance, pre-diabetes, increased fasting glucose, hyperglycemia, type 2 diabetes, hypertension, dyslipidemia, arteriosclerosis, coronary heart disease, peripheral artery disease, stroke, or any combination of these individual disease components.

38. A method for the treatment of non-alcoholic liver-disease (NAFLD) or non-alcoholic steatohepatitis (NASH), the method comprising administering to the patient an effective amount of the compound of claim 1, or a salt or solvate thereof.

* * * * *